US008435562B2

(12) United States Patent
Mao et al.

(10) Patent No.: US 8,435,562 B2
(45) Date of Patent: May 7, 2013

(54) PHARMACEUTICAL COMPOSITIONS AND ORAL DOSAGE FORMS OF A LEVODOPA PRODRUG AND METHODS OF USE

(75) Inventors: Chen Mao, Redwood City, CA (US); Nikhil Pargaonkar, Sunnyvale, CA (US); Laura E. Maurer, Sunnyvale, CA (US); Sarina Grace Harris Ma, Santa Clara, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

(21) Appl. No.: 12/941,971

(22) Filed: Nov. 8, 2010

(65) Prior Publication Data

US 2011/0111024 A1 May 12, 2011

Related U.S. Application Data

(60) Provisional application No. 61/259,567, filed on Nov. 9, 2009.

(51) Int. Cl.
*A61K 9/02* (2006.01)
*A61K 9/24* (2006.01)

(52) U.S. Cl.
USPC ............. 424/464; 424/451; 424/472; 560/39; 560/40

(58) Field of Classification Search .................. None
See application file for complete search history.

(56) References Cited

U.S. PATENT DOCUMENTS

| | | |
|---|---|---|
| 3,811,444 A | 5/1974 | Heller et al. |
| 3,845,770 A | 11/1974 | Theeuwes et al. |
| 3,916,899 A | 11/1975 | Theeuwes et al. |
| 3,962,414 A | 6/1976 | Michaels |
| 3,992,518 A | 11/1976 | Chien et al. |
| 4,038,411 A | 7/1977 | Saari |
| 4,066,747 A | 1/1978 | Capozza |
| 4,070,347 A | 1/1978 | Schmitt |
| 4,079,038 A | 3/1978 | Choi et al. |
| 4,083,949 A | 4/1978 | Benedikt |
| 4,093,709 A | 6/1978 | Choi et al. |
| 4,134,991 A | 1/1979 | Wermuth |
| 4,180,509 A | 12/1979 | Metcalf et al. |
| 4,311,706 A | 1/1982 | Bodor et al. |
| 4,663,349 A | 5/1987 | Repta |
| 4,771,073 A | 9/1988 | Repta |
| 4,826,875 A | 5/1989 | Chiesi |

(Continued)

FOREIGN PATENT DOCUMENTS

| | | |
|---|---|---|
| CA | 2607198 | 11/2006 |
| DE | 102005022276 A1 | 11/2006 |

(Continued)

OTHER PUBLICATIONS

Airaksinen et al., Excipient selection can significantly affect sold-state phase transformation in formulation during we granulation. *AAPS PharmSciTech* 2005, 6(2), E311-E322.

(Continued)

*Primary Examiner* — Lakshmi Channavajjala
(74) *Attorney, Agent, or Firm* — Kilpatrick Townsend & Stockton LLP

(57) ABSTRACT

Pharmaceutical compositions and oral dosage forms of (2R)-2-phenylcarbonyloxypropyl (2S)-2-amino-3-(3,4-dihydroxyphenyl)propanoate mesylate and methods of treating diseases comprising orally administering such pharmaceutical compositions and dosage forms are disclosed.

21 Claims, 9 Drawing Sheets

U.S. PATENT DOCUMENTS

| | | | |
|---|---|---|---|
| 4,873,263 A | 10/1989 | Repta | |
| 4,879,303 A | 11/1989 | Davison et al. | |
| 4,914,222 A | 4/1990 | Budavari et al. | |
| 4,966,915 A | 10/1990 | Tsuchiya et al. | |
| 4,983,400 A | 1/1991 | Dempski et al. | |
| 5,017,607 A | 5/1991 | Chiesi | |
| 5,057,321 A | 10/1991 | Edgren et al. | |
| 5,073,641 A | 12/1991 | Bundgaard et al. | |
| 5,128,145 A | 7/1992 | Edgren et al. | |
| 5,133,974 A | 7/1992 | Paradissis et al. | |
| 5,190,763 A | 3/1993 | Edgren et al. | |
| 5,283,352 A | 2/1994 | Backstrom et al. | |
| 5,332,576 A | 7/1994 | Mantelle | |
| 5,462,933 A | 10/1995 | Kramer et al. | |
| 5,607,969 A | 3/1997 | Milman et al. | |
| 5,637,780 A | 6/1997 | Jadhav et al. | |
| 5,698,155 A | 12/1997 | Grosswald et al. | |
| 5,725,883 A * | 3/1998 | Staniforth et al. | 424/489 |
| 5,827,819 A | 10/1998 | Yatvin et al. | |
| 5,840,756 A | 11/1998 | Cohen et al. | |
| 6,696,600 B2 | 2/2004 | Frenkel et al. | |
| 7,008,950 B1 * | 3/2006 | Ohkawa et al. | 514/278 |
| 7,101,912 B2 | 9/2006 | Xiang et al. | |
| 7,323,585 B2 | 1/2008 | Xiang et al. | |
| 7,342,131 B2 | 3/2008 | Xiang et al. | |
| 7,534,813 B2 | 5/2009 | Xiang et al. | |
| 7,563,821 B2 | 7/2009 | Xiang et al. | |
| 7,671,089 B2 | 3/2010 | Xiang et al. | |
| 7,709,527 B2 | 5/2010 | Xiang et al. | |
| 7,829,592 B2 | 11/2010 | Xiang et al. | |
| 7,893,105 B2 * | 2/2011 | Xiang et al. | 514/517 |
| 7,956,212 B2 | 6/2011 | Xiang et al. | |
| 7,968,597 B2 * | 6/2011 | Xiang et al. | 514/517 |
| 8,163,958 B2 | 4/2012 | Xiang et al. | |
| 2002/0099041 A1 | 7/2002 | Gallop et al. | |
| 2003/0152628 A1 | 8/2003 | Licht et al. | |
| 2003/0158254 A1 | 8/2003 | Zerangue et al. | |
| 2005/0209181 A1 | 9/2005 | Akil et al. | |
| 2005/0209246 A1 | 9/2005 | Ueda et al. | |
| 2005/0282891 A1 | 12/2005 | Xiang et al. | |
| 2006/0020028 A1 | 1/2006 | Xiang et al. | |
| 2007/0225366 A1 | 9/2007 | Xiang et al. | |
| 2008/0070984 A1 | 3/2008 | Tran et al. | |
| 2008/0103200 A1 | 5/2008 | Xiang et al. | |
| 2008/0132570 A1 | 6/2008 | Xiang et al. | |
| 2008/0171789 A1 | 7/2008 | Xiang et al. | |
| 2008/0214663 A1 | 9/2008 | Xiang et al. | |
| 2009/0137834 A1 | 5/2009 | Xiang et al. | |
| 2009/0156679 A1 | 6/2009 | Xiang et al. | |
| 2010/0099761 A1 | 4/2010 | Karaborni et al. | |
| 2010/0099907 A1 | 4/2010 | Raillard et al. | |
| 2010/0173992 A1 | 7/2010 | Xiang et al. | |
| 2010/0226855 A1 * | 9/2010 | Nangia et al. | 424/9.1 |
| 2011/0028544 A1 | 2/2011 | Xiang et al. | |
| 2011/0111062 A1 | 5/2011 | Xiang et al. | |
| 2011/0201817 A1 | 8/2011 | Xiang et al. | |
| 2012/0190861 A1 | 7/2012 | Xiang et al. | |

FOREIGN PATENT DOCUMENTS

| | | |
|---|---|---|
| EP | 0 309 827 B1 | 1/1992 |
| GB | 1447599 | 8/1976 |
| GB | 1537951 | 1/1979 |
| JP | 58-024547 | 2/1983 |
| WO | WO 86/04579 | 8/1986 |
| WO | WO 88/01615 A1 | 3/1988 |
| WO | WO 01/68065 A2 | 9/2001 |
| WO | WO 02/28882 A1 | 4/2002 |
| WO | WO 2007/087256 A2 | 8/2007 |

OTHER PUBLICATIONS

Staab et al., Control of polymorphism by 'tailor-mad' polymeric crystallization auxiliaries. Preferential precipitation of a metastable polar form for second harmonic generation. *Adv Mater* 1990, 2(1), 40-43.
Alpert and Friedhoff, Paradoxical reaction to L-dopa in schizophrenic patients. *Am J Psychiatry* 1978, 135(11), 1329-1332.
Bai, pGlu-L-Dopa-Pro: A tripeptide prodrug targeting the intestinal peptide transporter for absorption and tissue enzymes for conversion. *Pharm. Res.* 1995, 12(7), 1101-1104.
Betarbet et al., Animal models of Parkinson's disease. *Bioessays* 2002, 24(4), 308-18.
Berge et al., Pharmaceutical salts. *J. Pharm. Sci.* 1977, 66(1), 1-19.
Bodor et al., Improved delivery through biological membranes. 4. Prodrugs of L-Dopa. *J. Med. Chem.* 1977, 20(11), 1435-1445.
Boivin and Montplaisir, The effects of L-dopa on excessive daytime sleepiness in narcolepsy. *Neurology* 1991, 41, 1267-1269.
Bonelli and Wenning, Pharmacological management of Huntington's disease: an evidence-based review. *Current Pharmaceutical Design* 2006, 12(21), 2701-2720.
Bruno and Bruno, Effects of L-dopa on pharmacological parkinsonism. *Acta Psychiatr Scand* 1966, 4(3), 264-271.
Buchanan et al., Double blind trial of L-dopa in chronic schizophrenia. *Aust N Z J Psychiatry* 1975, 9(4), 269-271.
Carboxylic Acid Derivatives and Nitriles, http://www.chem.uky.edu/Courses/che232/JEA/In/9.%20Esters_etc.pdf, retrieved Mar. 24, 2010.
Cho et al., Dopamine neurons derived from embryonic stem cells efficiently induce behavioral recovery in a Parkinsonian rat model. *Biochem. Biophys. Res. Commun* 2006, 341(1), 6-12.
Coleman et al., A practical guide to polymer miscibility. *Polymer* 1990, 31, 1187-1203.
Conti et al., Levodopa for idiopathic restless legs syndrome: evidence-based review, *Mot Disord* 2007, 22(13), 1943-1951.
Cools, Dopaminergic modulation of cognitive function-implications for L-dopa treatment in Parkinson's disease. *Neuroscience Biobehavioral Rev* 2006, 30, 1-23.
Cooper et al., L-Dopa esters as potential prodrugs: behavioural activity in experimental models of Parkinson's disease. *J. Pharm. Pharmacol.* 1987, 39, 627-635.
Davey et al., Polymorphism in molecular crystals: stabilization of a metastable form by conformational mimidry. *J Am Chem Soc* 1997, 119(7), 1767-1772.
"Dissolution Testing of Immediate Release Solid Oral Dosage Forms—Guidance for Industry," U.S. Department of Health and Human Services, FDA-CDER, Aug. 1997, pp. 1-17.
Di Stefano et al., Dimeric L-Dopa derivatives as potential prodrugs. *Bioorganic & Medicinal Chem. Lett.* 2001, 11, 1085-1088.
Doggrell, The therapeutic potential of dopamine modulators on the cardiovascular and renal systems. *Expert Opin. Investig. Drugs*, 2002, 11(5), 631-644.
Durif et al., Worsening of levodopa-induced dyskinesias by motor and mental tasks. *Mov Disord* 1999, 14, 242-245.
During et al., Controlled release of dopamine from a polymeric brain implant: In vivo Characterization. *Ann. Neurol.* 1989, 25(4), 351-356.
Ebadi and Srinivasan, Pathogenesis, prevention and treatment of neuroleptic-induced movement disorders. *Pharmacological Reviews* 1995, 47(4), 575-604.
Eltayb et al., Enhanced cortical dopamine output and antipsychotic-like effect of raclopride with adjunctive low-dose L-dopa. *Biol Psychiatry* 2005, 58, 337-343.
Emborg, Evaluation of animal models of Parkinson's disease for neuroprotective strategies. *J. Neurosci Methods* 2004, 139(2), 121-143.
Fahn et al., Levodopa and the progression of Parkinson's disease. *N Engl J Med* 2004, 351(24), 2498-2508.
Faulkner et al, *Ann. Pharmacother.* 2003, 37(2), 282-6.
Fincher, Particle size of drugs and Its relationship to absorption and activity. *J. Pharm. Sci.* 1968, 57(11), 1825-1835.
Fix et al., Short-chain alkyl esters of L-Dopa as prodrugs for rectal absorption. *Pharm. Res.* 1989, 6(6), 501-505.
Fix et al., A comparison of oral and rectal absorption of L-Dopa esters in rats and mice. *Pharm. Res.* 1990, 7(4), 384-387.
Floel et al., Dopaminergic effects on encoding of a motor memory in chronic stroke. *Neurology* 2005, 65(3), 472-474.
Floel et al., Levodopa increases memory encoding and dopamine release in the striatum in the elderly. *Neurobiology of Aging* 2006, PMID 17098331.

Folstein et al., Mini-mental state. A practical method for grading the cognitive state of patients for the clinician. *J Psychiatr Res* 1975, 12(3), 189-198.

Garcia-Borreguero et al., Treatment of restless legs syndrome with gabapentin: a double-blind, cross-over study. *Neurol.* 2002, 11(2), 1573-79.

Garzon-Aburbeh et al., A lymphotropic prodrug of L-Dopa: synthesis, pharmacological properties, and pharmacokinetic behavior of 1,3-dihexadecanoyl-2-[(S)-2-amino-3-(3,4-dihydroxyphenyl)propanoyl]propane-1,2,3-triol. *J. Med. Chem.* 1986, 29, 687-691.

Gelb et al., Diagnostic criteria for Parkinson disease. *Arch Neurol* 1999, 56(1), 33-9.

Gerlach and Luhdorf, The effect of L-dopa on young patients with simple schizophrenia, treated with neuroleptic drugs. *Psychopharmacologia* 1975, 44(1), 105-110.

Gibb and Lees, The relevance of the Lewy body to the pathogenesis of idiopathic Parkinson's disease. *J Neurol Neurosurg Psychiatry* 1988, 51(6), 745-752.

Giovannoni et al., Bradykinesia akinesia inco-ordination test (BRAIN TEST): an objective computerized assessment of upper limb motor function. *J Neurol Neurosurg Psychiatry* 1999, 67, 624-629.

"Guidance for Industry—Bioavailability and Bioequivalence Studies for Orally Administered Drug Products—General Considerations," U.S. Department of Health and Human Services, FDA-CDER, Mar. 2003, pp. 1-26.

Hirsch et al., Animal models of Parkinson's disease in rodents induced by toxins: an update. *J Neural Transm Suppl* 2003, 65, 89-100.

Hisaka et al., Absorption of a novel prodrug of L-Dopa, L-3-(3-hydroxy-4-pivaloyloxyphenyl)alanine (NB-355). In Vitro and In Situ Studies, *Drug Metabolism and Disposition* 1990, 18(5), 621-625.

Hogl et al., Increased daytime sleepiness in Parkinson's disease: a questionnaire survey. *Movement Disorders* 2003, 18(3), 319-323.

Howard et al., Intracerebral drug delivery in rats with lesion-induced memory deficits. *J. Neurosurg* 1989, 71, 105-112.

Inanaga et al., Double-blind controlled study of L-dopa therapy in schizophrenia. *Folia Psychiatr Neurol Jpn* 1975, 29(2), 123-143.

Ishikura et al., Database CAS citation 1994:701312 [retrieved Nov. 23, 2009] from STN; Columbus, OH USA.

Ishikura et al., Database CAS citation 1995:365090 [retrieved Nov. 23, 2009] from STN; Columbus, OH USA.

Ishikura et al., Drug delivery to the brain. DOPA prodrugs based on a ring-closure reaction to quaternary thiazolium compounds. *Int'l. J. Pharmaceutics* 1995, 116, 51-63.

Jankovic, Treatment of dystonia. *Lancet Neurol* 2006, 5(10), 864-872.

Jaskiw and Popli, A meta-analysis of the response to chronic L-dopa in patients with schizophrenia: therapeutic and heuristic implications. *Psychopharmacology* 2004, 171, 365-374.

Juncos et al., Levodopa methyl ester treatment of Parkinson's disease. *Neurology* 1987, 37, 1242-1245.

Kay and Opler, L-dopa in the treatment of negative schizophrenic symptoms: a single-subject experimental study. *Int'l J Psychiatry Med* 1985-86, 15(3), 293-298.

Knecht et al., Levodopa: faster and better word learning in normal humans. *Ann. Neurol* 2004, 56(1), 20-26.

Kulisevsky, Role of dopamine in learning and memory: implications for the treatment of cognitive dysfunction in patients with Parkinson's disease. *Drugs Aging* 2000, 16(5), 365-379.

Langer, New methods of drug delivery. *Science* 1990, 249, 1527-1533.

Langer and Peppas, Chemical and physical structure of polymers as carriers for controlled release of bioactive agents: a review. *JMS-Rev. Macromol. Chem. Phys.*1983, C23(1), 61-126.

Leong and Langer, Polymeric controlled drug delivery. *Advanced Drug Delivery Reviews* 1987, 1, 199-233.

Leppert et al., The effects of carbidopa dose and time and route of administration on systemic L-Dopa levels in rats. *Pharmaceutical Res*1988, 5(9), 587-591.

Levy et al., Inhibition of calcification of bioprosthetic heart valves by local controlled-release diphosphonate. *Science* 1985, 228, 190-192.

Lu and Yu, Dimensionless presentation for drug release from a coated pure drug head: 2. Experiment. *Int. J. Pharmaceutics*1994, 112, 117-124.

Ludatsher, Stable remission of tardive dyskinesia by L-dopa. *J Clin Psychopharm* 1989, 9(1), 39-41.

Manson et al., An ambulatory dyskinesia monitor. *J Neurol Neurosurg Psychiatry* 2000, 68(2), 196-201.

Marrel et al., L-DOPA esters as potential prodrugs. *Eur. J. Med. Chem. Chim. Ther.* 1985, 5, 459-465.

Movement Disorder Society Task Force, The Unified Parkinson's Disease Rating Scale (UPDRS): status and recommendations. *Mov Disord* 2003, 18(7), 738-50.

Nutt Response to levodopa treatment in dopa-responsive dystonia. *Arch Neurol* 2001, 58, 905-910.

Olanow et al., Drug insight: continuous dopaminergic stimulation in the treatment of Parkinson's disease. *Nat Clin Pract Neurol* 2006, 2(7), 382-92.

Olson et al., Gabapentin for parkinsonism: a double-blind, placebo-controlled, crossover trial. *Am. J. Med.* 1997, 102(1), 60-6.

Ondo and Jankovic, Restless legs syndrome: clinicoetiologic correlates. *Neurology* 1996, 47(6), 1435-1441.

O'Neill et al., LY503430: pharmacology, pharmacokinetics, and effects in rodent models of Parkinson's disease. *CNS Drug Rev.* 2005, 11(1), 77-96.

Orth and Tabrizi, Models of Parkinson's disease. *Mov Disord* 2003, 18(7), 729-37.

O'Suilleabhain and Dewey, Contributions of dopaminergic drugs and disease severity to daytime sleepiness in Parkinson disease. *Arch. Neurol* 2002, 59, 986-989.

Paus et al., Sleep attacks, daytime sleepiness, and dopamine agonists in Parkinson's disease. *Movement Disorders* 2003, 18(6), 659-667.

Racette and Perlmutter, Levodopa responsive parkinsonism in an adult with Huntington's disease. *J Neurol Neurosurg Psychiatry* 1998, 65(4), 577-579.

Rascol and Fabre, Dyskinesia: L-Dopa-induced and tardive dyskinesia. *Clinical Neuropharmacology* 2001, 24(6), 313-323.

Rouhi, The Right Stuff. *Science and Technology*, C&E News Feb. 2003, 32-35.

Saari, abstract, Database CAS citation 1978:444225 [retrieved Mar. 24, 2010] from STN: Columbus, OH, USA.

Sasahara et al., Dosage form design for improvement of bioavailability of levodopa II: bioavailability of marketed levodopa preparations in dogs and Parkinsonian patients. *J. Pharm. Sci.* 1980, 69(3), 261-265.

Saudek et al., A preliminary trial of the programmable implantable medication system for insulin delivery. *N. Engl. J. Med.* 1989, 321, 574-579.

Scheidtmann et al., Effect of levodopa in combination with physiotherapy on functional motor recovery after stroke: a prospective, randomized, double-blind study. *Lancet* 2001, 358(9284), 787-790.

Schneider et al., Familial dopa-responsive cervical dystonia. *Neurology* 2006, 66(4), 599-601.

Sefton, Implantable pumps. *CRC Critical Reviews in Biomedical Engineering* 1987, 14(3), 201-240.

Silber, Sleep disorders. *Neurologic Clin* 2001, 19(1), 173-186.

Soares and McGrath, The treatment of tardive dyskinesia—a systematic review and meta-analysis. *Schizophrenia Research* 1999, 39, 1-16.

Tang et al., Synthesis and characterization of water-soluble and photostable L-dopa dendrimers. *Organic Letters* 2006, 8(20), 4421-4424.

Tolwani et al., Experimental models of Parkinson's disease: insights from many models. *Lab Anim Sci* 1999, 49(4), 363-71.

Van Blercom et al., Effects of gabapentin on the motor response to levodopa: a double-blind, placebo-controlled, crossover study in patients with complicated Parkinson disease. *Clin Neuropharmacol* 2004, 27(3), 124-8.

Verma et al., Osmotically controlled oral drug delivery. *Drug Development and Industrial Pharmacy* 2000, 26(7), 695-708.

Von Scheele, Levodopa in restless legs. *Lancet* 1986, 2(8504), 426-427.

Wang et al., Preparation and intestinal absorption of L-Dopa-D-phenylglycine. *J. Food and Drug Analysis* 2002, 10(2), 81-87.

Wang et al., Synthesis and pharmacological activities of a novel tripeptide mimetic dopamine prodrug. *Bioorganic & Medicinal Chemistry Letters* 1995, 5(19), 2195-2198.

Wikstrom et al., Manipulating theophylline monohydrate formation during high-shear wet granulation through improved understanding of the role of pharmaceutical excipients. *Pharmaceutical Research* 2008, 25(4), 923-935.

International Search Report and Written Opinion mailed Nov. 3, 2005, for International Application No. PCT/US2005/019492, filed Jun. 3, 2005.

International Search Report and Written Opinion mailed Nov. 3, 2005, for International Application No. PCT/US2005/019493, filed Jun. 3, 2005.

International Search Report and Written Opinion mailed Jul. 23, 2007, for International Application No. PCT/US2006/046273, filed Dec. 4, 2006.

International Search Report and Written Opinion of the International Searching Authority mailed Apr. 15, 2008, for International Application No. PCT/US2007/026200 filed Dec. 20, 2007.

International Search Report and Written Opinion of the International Searching Authority mailed May 14, 2008, for International Application No. PCT/US2007/026271, filed Dec. 20, 2007.

International Search Report and Written Opinion of the International Searching Authority mailed May 27, 2008, for International Application No. PCT/US2007/078541, filed Sep. 14, 2007.

Office Action mailed Nov. 24, 2006, for U.S. Appl. No. 11/145,159, filed Jun. 3, 2005.

Final Office Action mailed Jun. 15, 2007, for U.S. Appl. No. 11/145,159, filed Jun. 3, 2005.

Office Action mailed Jan. 19, 2007, for U.S. Appl. No. 11/145,280, filed Jun. 3, 2005.

Office Action mailed Apr. 17, 2007, for U.S. Appl. No. 11/145,280, filed Jun. 3, 2005.

Office Action mailed Oct. 24, 2008, for U.S. Appl. No. 12/001,618, filed Dec. 11, 2007.

Office Action mailed Jun. 3, 2008, for U.S. Appl. No. 12/008,473, filed Jan. 10, 2008.

Office Action mailed Mar. 21, 2008, for U.S. Appl. No. 11/634,354, filed Dec. 4, 2006.

Office Action mailed Sep. 16, 2008, for U.S. Appl. No. 11/634,354, filed Dec. 4, 2006.

Office Action mailed Aug. 7, 2009, for U.S. Appl. No. 12/005,117, filed Dec. 20, 2007.

Notice of Allowance mailed Jun. 25, 2010, for U.S. Appl. No. 12/005,120, filed Dec. 20, 2007.

Notice of Allowance mailed Mar. 20, 2009, for U.S. Appl. No. 11/634,354, filed Dec. 4, 2006.

Notice of Allowance mailed Jun. 22, 2009, for U.S. Appl. No. 11/634,354, filed Dec. 4, 2006.

Notice of Allowance mailed Oct. 15, 2008, for U.S. Appl. No. 12/008,473, filed Jan. 10, 2008.

Notice of Allowance mailed May 29, 2009, for U.S. Appl. No. 12/001,618, filed Dec. 11, 2007.

Notice of Allowance, Notice of Allowability, and Examiner's Amendment mailed Sep. 11, 2007, for U.S. Appl. No. 11/145,280, filed Jun. 3, 2005.

Notice of Allowance mailed Oct. 10, 2007, for U.S. Appl. No. 11/145,159, filed Jun. 3, 2005.

Notice of Allowance mailed Jan. 23, 2008, for U.S. Appl. No. 11/145,159, filed Jun. 3, 2005 (Supplemental).

Notice of Allowance mailed Jan. 6, 2011, for U.S. Appl. No. 12/364,453.

U.S. Appl. No. 12/726,978, filed Mar. 18, 2010.

International Search Report and Written Opinion mailed on Apr. 28, 2011, for International Application No. PCT/US2010/002937, filed on Nov. 8, 2010.

Non-Final Office Action mailed Nov. 23, 2012 for U.S. Appl. No. 13/473,503.

Notice of Allowance mailed Nov. 14, 2012 for U.S. Appl. No. 12/581,810.

Final Office Action mailed Nov. 15, 2012 for U.S. Appl. No. 13/440,936.

"Methylpyrrolidone" article from Wikipedia downloaded Aug. 24, 2012.

Airaksinen et al., Excipient selection can significantly affect solid-state phase transformation in formulation during wet granulation. *AAPS PharmSciTech* 2005, 6(2), E311-E322.

Hoes et al., The application of drug-polymer conjugates in chemotherapy, *Drug Carrier System*, 1989, 9, 57-100.

Kirk-Othmer Encyclopedia of Chemical Technology, John Wiley & Sons, Inc., pp. 95-147 (Aug. 2002).

Langer, Medical applications of controlled release, *Science*, 1983, C23(1), 61-126.

Schneider et al., Familial dopa-responsive cervical dystonia, *Neurology*, 2006, 66(4), 599-601.

Sefton, Implantable pumps, *CRC Crit. Rev. Biomed. Eng.*, 1987, 14(3), 201-240.

Staab et al., Control of polymorphism by 'tailor-made' polymeric crystallization auxiliaries. Preferential precipitation of a metastable polar form for second harmonic generation, *Adv Mater* 1990, 2(1), 40-43.

*Ullmann's Encyclopedia of Industrial Chemistry*, Wiley-VCH Verlag GmbH & Co. pp. 1-51 (2002).

Van Blercom et al., Effects of gabapentin on the motor response to levodopa: a double blind, placebo-controlled, crossover study in patients with complicated Parkinson disease, *Clin Neuropharmacol*, 2004, 27(3), 124-128.

International Search Report, Written Opinion, and International Preliminary Report on Patentability mailed Jul. 30, 2012, Apr. 20, 2011, and Apr. 26, 2011, respectively, for PCT/US2009/005698 filed Oct. 19, 2009.

Notice of Allowance mailed Dec. 16, 2009, for U.S. Appl. No. 12/005,117, filed Dec. 20, 2007.

Office Action mailed Jan. 25, 2010, for U.S. Appl. No. 12/005,120, filed Dec. 20, 2007.

Notice of Allowance mailed Jan. 25, 2010, for U.S. Appl. No. 12/005,120, filed Dec. 20, 2007.

Office Action mailed May 4, 2010, for U.S. Appl. No. 12/347,807, filed Dec. 31, 2008.

Office Action mailed Oct. 18, 2010, for U.S. Appl. No. 12/347,807, filed Dec. 31, 2008.

Notice of Allowance mailed Feb. 17, 2011, for U.S. Appl. No. 12/347,807, filed Dec. 31, 2008.

Office Action mailed Dec. 1, 2009, (later vacated) for U.S. Appl. No. 12/364,453, filed Feb. 2, 2009.

Office Action mailed Apr. 1, 2010, for U.S. Appl. No. 12/364,453, filed Feb. 2, 2009.

Office Action mailed Aug. 30, 2010, for U.S. Appl. No. 12/364,453, filed Feb. 2, 2009.

Notice of Allowance mailed Jan. 6, 2011, for U.S. Appl. No. 12/364,453, filed Feb. 2, 2009.

Office Action mailed Apr. 28, 2010, for U.S. Appl. No. 12/489,146, filed Jun. 22, 2009.

Notice of Allowance mailed Oct. 12, 2010, for U.S. Appl. No. 12/489,146, filed Jun. 22, 2009.

Office Action mailed Jun. 11, 2012, for U.S. Appl. No. 12/581,810, filed Oct. 19, 2009.

Office Action mailed Jun. 11, 2012, for U.S. Appl. No. 12/726,978, filed Mar. 18, 2010.

Notice of Allowance and Notice of Allowability mailed Aug. 14, 2012, for U.S. Appl. No. 12/726,978, filed Mar. 18, 2010.

Office Action mailed Apr. 30, 2012, for U.S. Appl. No. 12/904,960, filed Oct. 14, 2010.

Notice of Allowance and Notice of Allowability mailed Jul. 27, 2012, for U.S. Appl. No. 12/904,960, filed Oct. 14, 2010.

Office Action mailed Mar. 27, 2012, for U.S. Appl. No. 12/941,971, filed Nov. 8, 2010.

Office Action mailed May 18, 2012, for U.S. Appl. No. 13/010,419, filed Jan. 20, 2011.

Notice of Allowance mailed Feb. 7, 2012, for U.S. Appl. No. 13/010,419, filed Jan. 20, 2011.

Office Action mailed Sep. 22, 2011, for U.S. Appl. No. 13/095,101, filed Apr. 27, 2011.

Notice of Allowance mailed Dec. 27, 2011, for U.S. Appl. No. 13/095,101, filed Apr. 27, 2011.
Office Action mailed May 18, 2012, for U.S. Appl. No. 13/440,936, filed Apr. 5, 2012.
Office Action mailed Aug. 30, 2012, for U.S. Appl. No. 12/581,808, filed Oct. 19, 2009.

* cited by examiner

PHARMACEUTICAL COMPOSITIONS AND ORAL DOSAGE FORMS OF A LEVODOPA PRODRUG AND METHODS OF USE

This application claims benefit of U.S. Provisional Application No. 61/259,567, filed on Nov. 9, 2009, which is incorporated by reference herein.

The disclosure relates to pharmaceutical compositions and oral dosage forms of a levodopa prodrug and to methods of treating a disease comprising orally administering such pharmaceutical compositions and dosage forms.

Parkinson's disease is a disabling, progressive illness that affects one in 1,000 people and generally occurs in people over the age of 50 years. Patients with Parkinson's disease have a deficiency of the neurotransmitter dopamine in the brain as a result of nigrostriatal pathway disruption caused by degeneration of the substantia nigra. Levodopa (L-dopa or L-3,4-dihydroxyphenylalanine), an immediate precursor of dopamine, is the most commonly prescribed drug for treatment of this disease.

Following oral administration, levodopa is rapidly absorbed via an amino acid transporter present in the upper small intestine. Due to the narrow distribution of this transporter system, the window available for levodopa absorption is limited and the extent of absorption can depend on the rate at which the drug passes through the upper gastrointestinal tract.

Intestinal metabolism of levodopa is the major source of first pass loss of the drug. Approximately 35% of an administered dose of levodopa reaches the systemic circulation as intact levodopa after oral administration in patients (Sasahara, *J. Pharm. Sci* 1990, 69, 261). Once absorbed, levodopa is rapidly metabolized to dopamine by L-aromatic amino acid decarboxylase (AADC) enzymes in the peripheral tissues (e.g., intestines and liver). For this reason, levodopa is normally co-administered with a decarboxylase enzyme inhibitor such as carbidopa or benserazide. When administered with carbidopa, the plasma concentration of intact levodopa increases and thus more levodopa becomes available to be transported into the central nervous system where it is converted to dopamine. Carbidopa and benserazide do not cross the blood-brain barrier to a significant extent and therefore do not inhibit the required conversion of levodopa to dopamine in the brain.

Levodopa prodrugs designed to be absorbed from both the small and large intestine have been described in U.S. Pat. No. 7,323,585, U.S. Pat. No. 7,342,131, U.S. Patent Application Publication No. 2008/0103200 (issued as U.S. Pat. No. 7,671,089), U.S. Pat. No. 7,534,813, U.S. Patent Application Publication No. 2008/0171789 (issued as U.S. Pat. No. 7,709,527), U.S. Patent Application Publication No. 2008/0214663, and U.S. Patent Application Publication No. 2009/0137834. These levodopa prodrugs can achieve an oral bioavailability of levodopa that is at least two times greater than the oral bioavailability of levodopa when orally administered on an equivalent molar basis. More specifically, U.S. Pat. No. 7,342,131 and U.S. Pat. No. 7,534,813 disclose the compound (2R)-2-phenylcarbonyloxypropyl (2S)-2-amino-3-(3,4-dihydroxyphenyl)propanoate hydrochloride in an amorphous or crystalline form. Crystalline (2R)-2-phenylcarbonyloxypropyl (2S)-2-amino-3-(3,4-dihydroxyphenyl)propanoate mesylate 1:

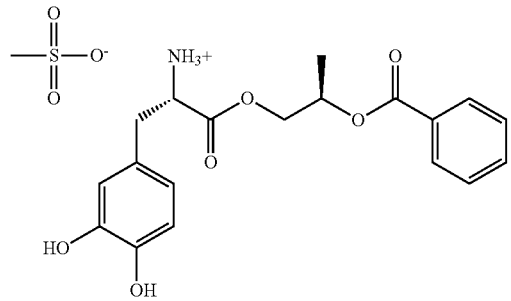

(1)

is described in U.S. Pat. No. 7,563,821. These levodopa prodrugs can be incorporated into sustained release formulations to provide sustained systemic exposure to levodopa upon oral administration to a patient.

U.S. application Ser. No. 12/581,810, filed on Oct. 19, 2009 (U.S. Application Publication No. 2010/0099761), discloses crystalline hydrates of (2R)-2-phenylcarbonyloxypropyl (2S)-2-amino-3-(3,4-dihydroxyphenyl)propanoate mesylate, and in particular (2R)-2-phenylcarbonyloxypropyl (2S)-2-amino-3-(3,4-dihydroxyphenyl)propanoate mesylate, sesqui-hydrate. Hydrates of (2R)-2-phenylcarbonyloxypropyl (2S)-2-amino-3-(3,4-dihydroxyphenyl)propanoate mesylate were found to be formed under certain conditions of environmental water content. Different crystalline forms and hydrates of a compound can have different solid state physical properties that can impact, for example, the processability of the compound, the rate of dissolution of the compound from a dosage form, and the stability of the compound. It is therefore desirable to control hydrate formation.

Accordingly, pharmaceutical compositions and oral dosage forms are disclosed wherein hydrate formation of crystalline (2R)-2-phenylcarbonyloxypropyl (2S)-2-amino-3-(3,4-dihydroxyphenyl)propanoate mesylate is controlled.

In a first aspect, pharmaceutical compositions are provided comprising crystalline (2R)-2-phenylcarbonyloxypropyl (2S)-2-amino-3-(3,4-dihydroxyphenyl)propanoate mesylate and a $C_{6-18}$ alkylsulfate or pharmaceutically acceptable salt thereof.

In a second aspect, oral tablet dosage forms are provided comprising crystalline (2R)-2-phenylcarbonyloxypropyl (2S)-2-amino-3-(3,4-dihydroxyphenyl)propanoate mesylate and a $C_{6-18}$ alkylsulfate or pharmaceutically acceptable salt thereof.

In a third aspect, methods are provided for treating a disease in a patient such as Parkinson's disease, schizophrenia, a cognitive impairment disorder, restless legs syndrome, a periodic limb movement disorder, tardive dyskinesia, Huntington's disease, hypertension, and excessive daytime sleepiness comprising administering to a patient in need of such treatment a pharmaceutical composition comprising a therapeutically effective amount of crystalline (2R)-2-phenylcarbonyloxypropyl (2S)-2-amino-3-(3,4-dihydroxyphenyl)propanoate, mesylate and a $C_{6-18}$ alkylsulfate or pharmaceutically acceptable salt thereof.

In a fourth aspect, methods are provided for treating a disease in a patient such as Parkinson's disease, schizophrenia, a cognitive impairment disorder, restless legs syndrome, a periodic limb movement disorder, tardive dyskinesia, Huntington's disease, hypertension, and excessive daytime sleepiness comprising administering to a patient in need of such treatment an oral dosage form comprising crystalline (2R)-2-phenylcarbonyloxypropyl (2S)-2-amino-3-(3,4-dihydroxyphenyl)propanoate, mesylate and a $C_{6-18}$ alkylsulfate or pharmaceutically acceptable salt thereof.

Those skilled in the art will understand that the drawings, described herein, are for illustration purposes only. The drawings are not intended to limit the scope of the present disclosure.

Figure 1:
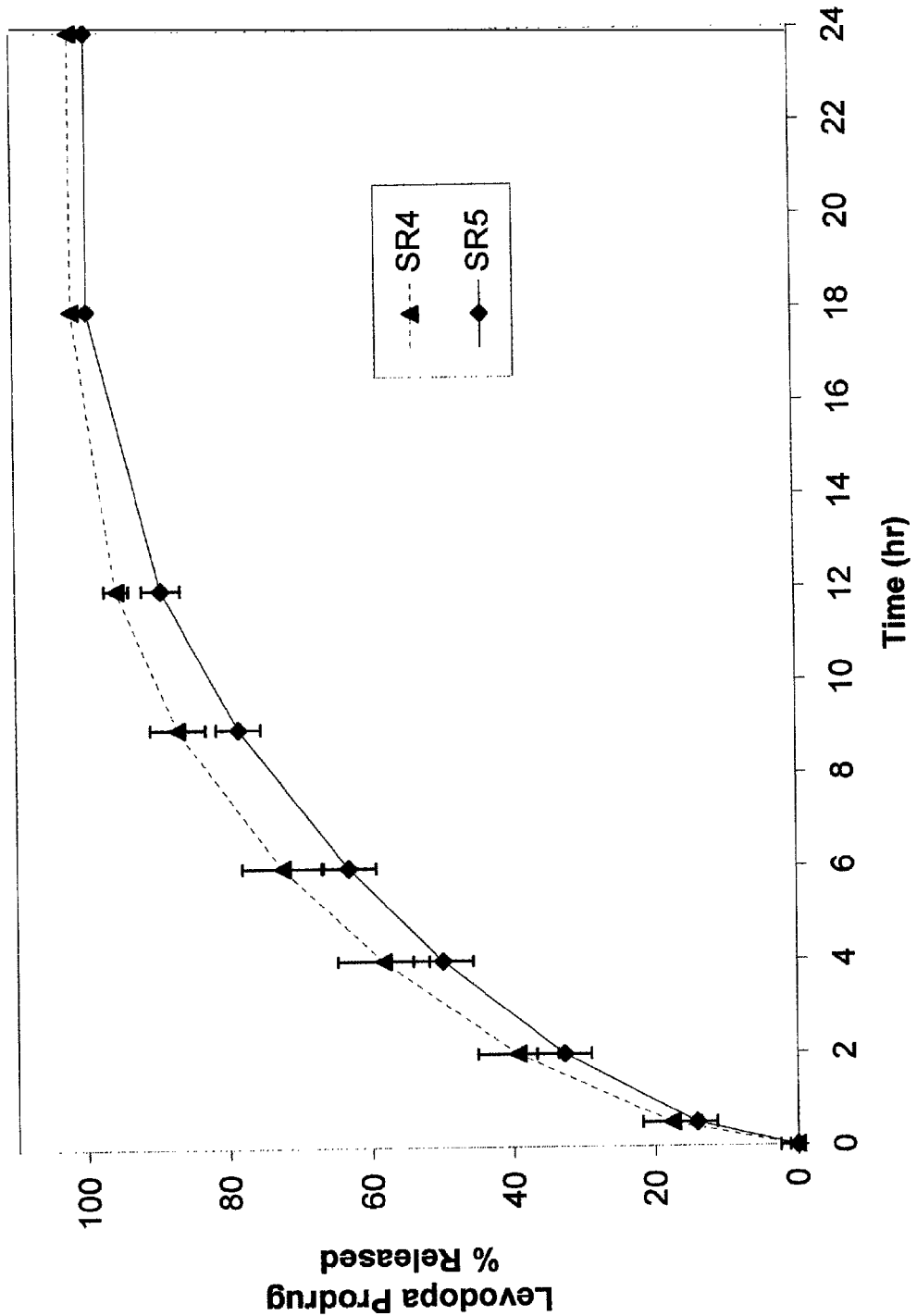
FIG. 1 shows dissolution profiles for SR4 and SR5 tablets prepared according to Example 5.

"Patient" or "subject" includes mammals, such as for example, humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a levodopa prodrug may be administered to a patient, which does not destroy the pharmacological activity thereof, and which is nontoxic when administered in doses sufficient to provide a therapeutically effective amount of levodopa.

"(2R)-2-Phenylcarbonyloxypropyl (2S)-2-amino-3-(3,4-dihydroxyphenyl)propanoate mesylate (1)" has the following structure:

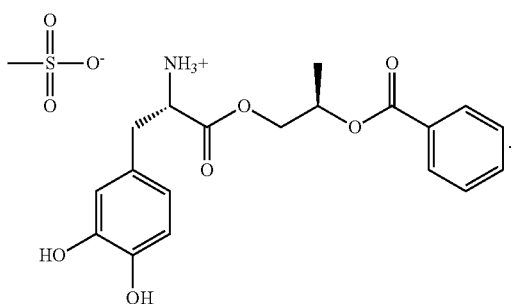

(1)

"Prodrug" refers to a derivative of an active compound (drug) that undergoes a transformation under the conditions of use, such as within the body, to release an active drug. Prodrugs are frequently, but not necessarily, pharmacologically inactive until converted into the active drug. Prodrugs can be obtained by bonding a promoiety (defined herein), typically via a functional group, to a drug. For example, (2R)-2-phenylcarbonyloxypropyl (2S)-2-amino-3-(3,4-dihydroxyphenyl)propanoate, mesylate is metabolized within a patient's body to form the parent drug levodopa.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach or the agent may be supplied exogenously. For example, for (2R)-2-phenylcarbonyloxypropyl (2S)-2-amino-3-(3,4-dihydroxyphenyl)propanoate, mesylate, the drug is levodopa and the promoiety has the structure:

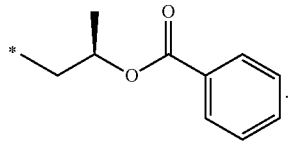

"Therapeutically effective amount" refers to the amount of a compound that, when administered to a subject for treating a disease or disorder, or at least one of the clinical symptoms of a disease or disorder, is sufficient to affect such treatment of the disease, disorder, or symptom. The therapeutically effective amount may vary depending, for example, on the compound, the disease, disorder, and/or symptoms of the disease, severity of the disease or disorder, and/or symptoms of the disease, the age, weight, and/or health of the patient to be treated, and the judgment of the prescribing physician. An appropriate amount may be ascertained by those skilled in the art or capable of determination by routine experimentation.

"Treating" or "treatment" of a disease refers to arresting or ameliorating a disease, disorder, or at least one of the clinical symptoms of a disease or disorder. In certain embodiments, "treating" or "treatment" refers to arresting or ameliorating at least one physical parameter of the disease or disorder, which may or may not be discernible by the patient. In certain embodiments, "treating" or "treatment" refers to inhibiting or controlling the disease or disorder, either physically (e.g., stabilization of a discernible symptom), physiologically (e.g., stabilization of a physical parameter), or both. In certain embodiments, "treating" or "treatment" refers to delaying, in some cases indefinitely, the onset of a disease or disorder.

Reference is now made in detail to certain embodiments of pharmaceutical compositions, dosage forms and methods. The disclosed embodiments are not intended to be limiting of the claims. To the contrary, the claims are intended to cover all alternatives, modifications, and equivalents.

Pharmaceutical compositions provided by the present disclosure comprise crystalline (2R)-2-phenylcarbonyloxypropyl (2S)-2-amino-3-(3,4-dihydroxyphenyl)propanoate, mesylate and a $C_{6-18}$ alkylsulfate or pharmaceutically acceptable salt thereof.

Levodopa prodrugs are disclosed in U.S. Pat. No. 7,323,585, U.S. Pat. No. 7,342,131, U.S. Patent Application Publication No. 2008/0171789, and U.S. Patent Application Publication No. 2008/0214663 (issued as U.S. Pat. No. 7,709,527). The levodopa prodrug, (2R)-2-phenylcarbonyloxypropyl (2S)-2-amino-3-(3,4-dihydroxyphenyl)propanoate mesylate 1:

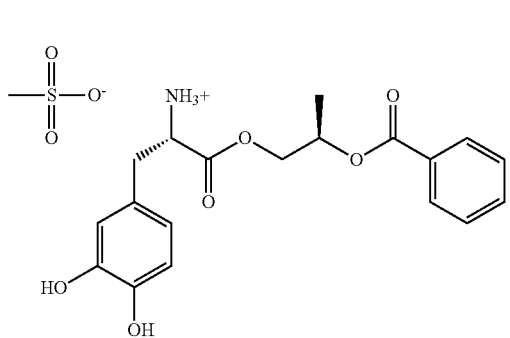

(1)

and the crystalline form thereof, and methods of synthesis are disclosed in U.S. Pat. No. 7,563,821. Methods of synthesis are also disclosed in U.S. application Ser. No. 12/581,808, filed on Oct. 19, 2009 (U.S. Application Publication No. 2010/0099907). Hydrates of crystalline (2R)-2-phenylcarbonyloxypropyl (2S)-2-amino-3-(3,4-dihydroxyphenyl)propanoate, mesylate are disclosed in U.S. application Ser. No. 12/581,810, filed on Oct. 19, 2009 (U.S. Application Publication No. 2010/0099761).

One skilled in the art will appreciate that although crystalline (2R)-2-phenylcarbonyloxypropyl (2S)-2-amino-3-(3,4-dihydroxyphenyl)propanoate mesylate is disclosed, a sample of crystalline (2R)-2-phenylcarbonyloxypropyl (2S)-2-amino-3-(3,4-dihydroxyphenyl)propanoate mesylate can have various compositional and diastereomeric purities. In certain embodiments, crystalline (2R)-2-phenylcarbonyloxypropyl (2S)-2-amino-3-(3,4-dihydroxyphenyl)propanoate mesylate can exhibit a compositional purity of at least about 90%, at least about 91%, at least about 92%, at least about 93%, at least about 94%, at least about 95%, at least about 96%, at least about 97%, at least about 98%, at least about 99%, and in certain embodiments, in excess of at least about 99%. In certain embodiments, crystalline (2R)-2-phenylcarbonyloxypropyl (2S)-2-amino-3-(3,4-dihydroxyphenyl)propanoate mesylate can exhibit a diastereomeric purity of at least about 90%, at least about 91%, at least about 92%, at least about 93%, at least about 94%, at least about 95%, at least about 96%, at least about 97%, at least about 98%, at least about 99%, and in certain embodiments, in excess of at least about 99%.

Crystalline (2R)-2-phenylcarbonyloxypropyl (2S)-2-amino-3-(3,4-dihydroxyphenyl)propanoate mesylate may exist in several tautomeric forms. Accordingly, all possible tautomeric forms of crystalline (2R)-2-phenylcarbonyloxypropyl (2S)-2-amino-3-(3,4-dihydroxyphenyl)propanoate mesylate are encompassed unless otherwise specified. All isotopically labeled forms of crystalline (2R)-2-phenylcarbonyloxypropyl (2S)-2-amino-3-(3,4-dihydroxyphenyl)propanoate mesylate are also encompassed unless otherwise specified. Examples of isotopes that may be incorporated into crystalline (2R)-2-phenylcarbonyloxypropyl (2S)-2-amino-3-(3,4-dihydroxyphenyl)propanoate mesylate include, but are not limited to, $^{2}H$, $^{3}H$, $^{11}C$, $^{13}C$, $^{14}C$, $^{15}N$, $^{18}O$, and $^{17}O$.

Figure 2:
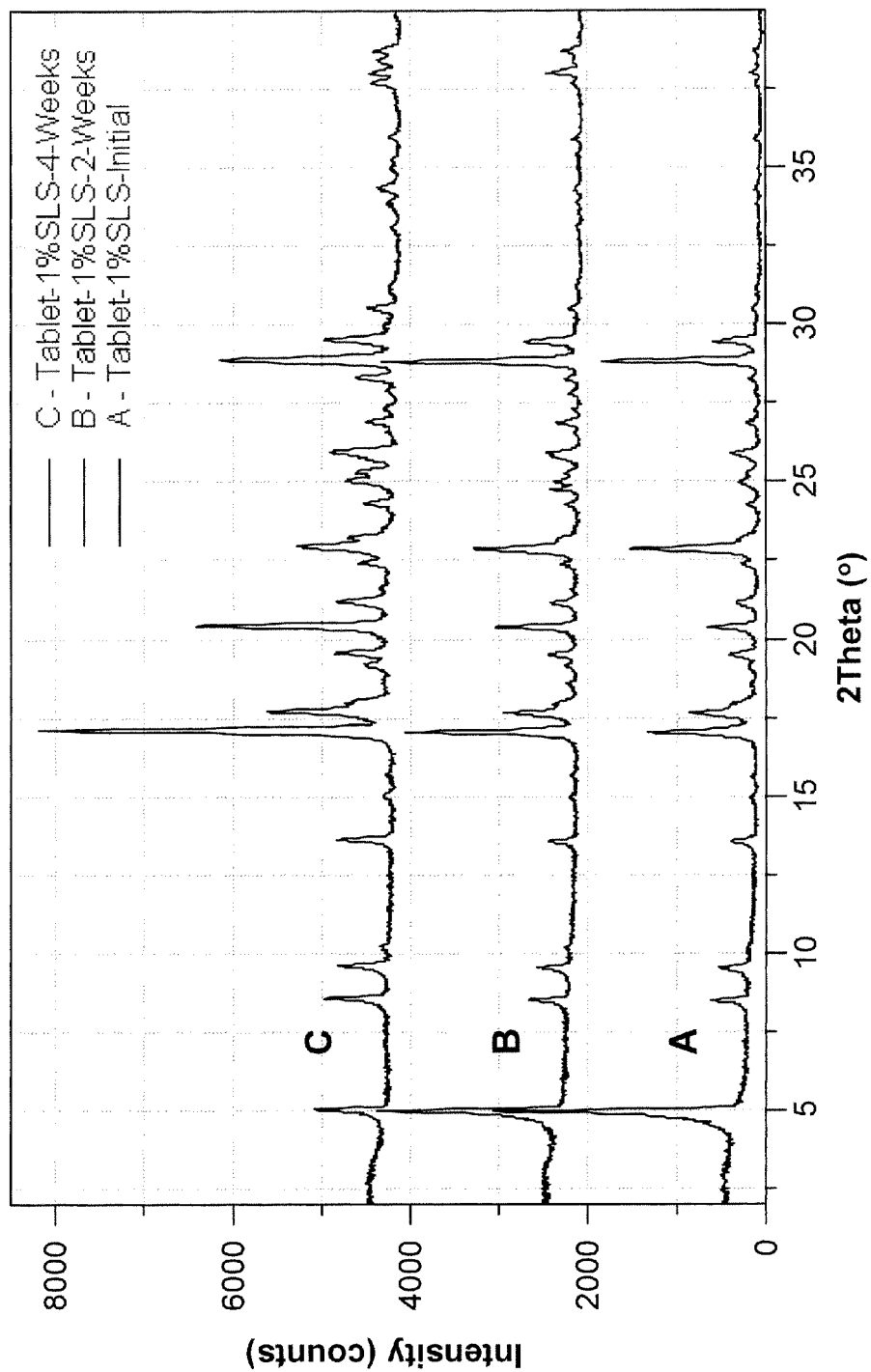
FIG. 2 shows PXRD patterns for ground SR5 tablets prepared according to Example 5 following exposure to 40° C./75% relative humidity (RH) for up to 4 weeks.

In certain embodiments, a powder X-ray diffraction (PXRD) pattern of anhydrous crystalline (2R)-2-phenylcarbonyloxypropyl (2S)-2-amino-3-(3,4-dihydroxyphenyl)propanoate mesylate exhibits characteristic diffraction peaks (° 2θ) at 4.7°±0.2°, 5.0°±0.2°, 8.5°±0.2°, 9.6°±0.2°, 13.6°±0.2°, 15.0°±0.2°, 17.0°±0.2°, 17.4°±0.2°, 17.7°±0.2°, 19.1°±0.2°, 19.5°±0.2°, 20.0°±0.2°, 20.4°±0.2°, 21.1°±0.2°, 22.3°±0.2°, 22.9°±0.2°, 23.1°±0.2°, 23.3°±0.2°, 24.3°±0.2°, 25.0°±0.2°, 25.3°±0.2°, 25.7°±0.2°, 25.8°±0.2°, 26.9°±0.2°, 27.3°±0.2°, 28.2°±0.2°, 30.1°±0.2°, 30.5°±0.2, 32.0°±0.2°, 33.8°±0.2°, 34.3°±0.2°, 37.6°±0.2°, and 38.4°±0.2°. PXRD patterns of anhydrous crystalline (2R)-2-phenylcarbonyloxypropyl (2S)-2-amino-3-(3,4-dihydroxyphenyl)propanoate mesylate are shown in FIG. 2 (patterns A-C) and FIG. 3 (pattern A).

One skilled in the art will recognize that slight variations in the observed ° 2θ diffraction angles can be expected based on, for example, the specific diffractometer employed, the analyst, and the sample preparation technique. Greater variation can be expected for the relative peak intensities. Comparison of diffraction patterns can be based primarily on observed ° 2θ diffraction angles with lesser importance attributed to relative peak intensities. For the powder X-ray diffraction patterns of anhydrous crystalline (2R)-2-phenylcarbonyloxypropyl (2S)-2-amino-3-(3,4-dihydroxyphenyl)propanoate mesylate, the peaks that generally exhibit the most intensity are located at ° 2θ diffraction angles of 5.0°±0.2°, 8.5°±0.2°, 13.6°±0.2°, 15.0°±0.2°, 17.0°±0.2°, 17.7°±0.2°, 20.4°±0.2°, 21.1°±0.2°, 25.0°±0.2°, 25.8°±0.2°, 28.2°±0.2, 30.1°±0.2°, and 37.6°±0.2°. A powder X-ray diffraction pattern that exhibits characteristic diffraction peaks (° 2θ) at 5.0°±0.2°, 8.5°±0.2°, 13.6°±0.2°, 15.0°±0.2°, 17.0°±0.2°, 17.7°±0.2°, 20.4°±0.2°, 21.1°±0.2°, 25.0°±0.2°, 25.8°±0.2°, 28.2°±0.2°, 30.1°±0.2°, and 37.6°±0.2° will be substantially the same as the X-ray powder diffraction pattern of anhydrous crystalline (2R)-2-phenylcarbonyloxypropyl (2S)-2-amino-3-(3,4-dihydroxyphenyl)propanoate mesylate.

In certain embodiments, anhydrous crystalline (2R)-2-phenylcarbonyloxypropyl (2S)-2-amino-3-(3,4-dihydroxyphenyl)propanoate mesylate exhibits a melting point from about 157° C. to about 162° C.

In certain embodiments, anhydrous crystalline (2R)-2-phenylcarbonyloxypropyl (2S)-2-amino-3-(3,4-dihydroxyphenyl)propanoate mesylate is characterized by a differential scanning calorimetry (DSC) thermogram having an endothermic peak at about 164.5° C., and in certain embodiments at about 164.5±2.5° C.

In certain embodiments, anhydrous crystalline (2R)-2-phenylcarbonyloxypropyl (2S)-2-amino-3-(3,4-dihydroxyphenyl)propanoate mesylate is stable, e.g., does not absorb moisture and/or convert to another isomorphic form under typical pharmaceutical processing and/or storage conditions.

The physical properties and characteristics of crystalline (2R)-2-phenylcarbonyloxypropyl (2S)-2-amino-3-(3,4-dihydroxyphenyl)propanoate mesylate prepared by methods disclosed in U.S. Pat. No. 7,563,821 are consistent with that of a single isomorph. The environmental stability of the single isomorphic form of crystalline (2R)-2-phenylcarbonyloxypropyl (2S)-2-amino-3-(3,4-dihydroxyphenyl)propanoate mesylate recommends its use in pharmaceutical compositions.

Under certain conditions of water activity as disclosed in U.S. application Ser. No. 12/581,810, filed on Oct. 19, 2009 (U.S. Application Publication No. 2010/0099761), anhydrous crystalline (2R)-2-phenylcarbonyloxypropyl (2S)-2- amino-3-(3,4-dihydroxyphenyl)propanoate, mesylate will convert to a crystalline hydrate.

Figure 3:
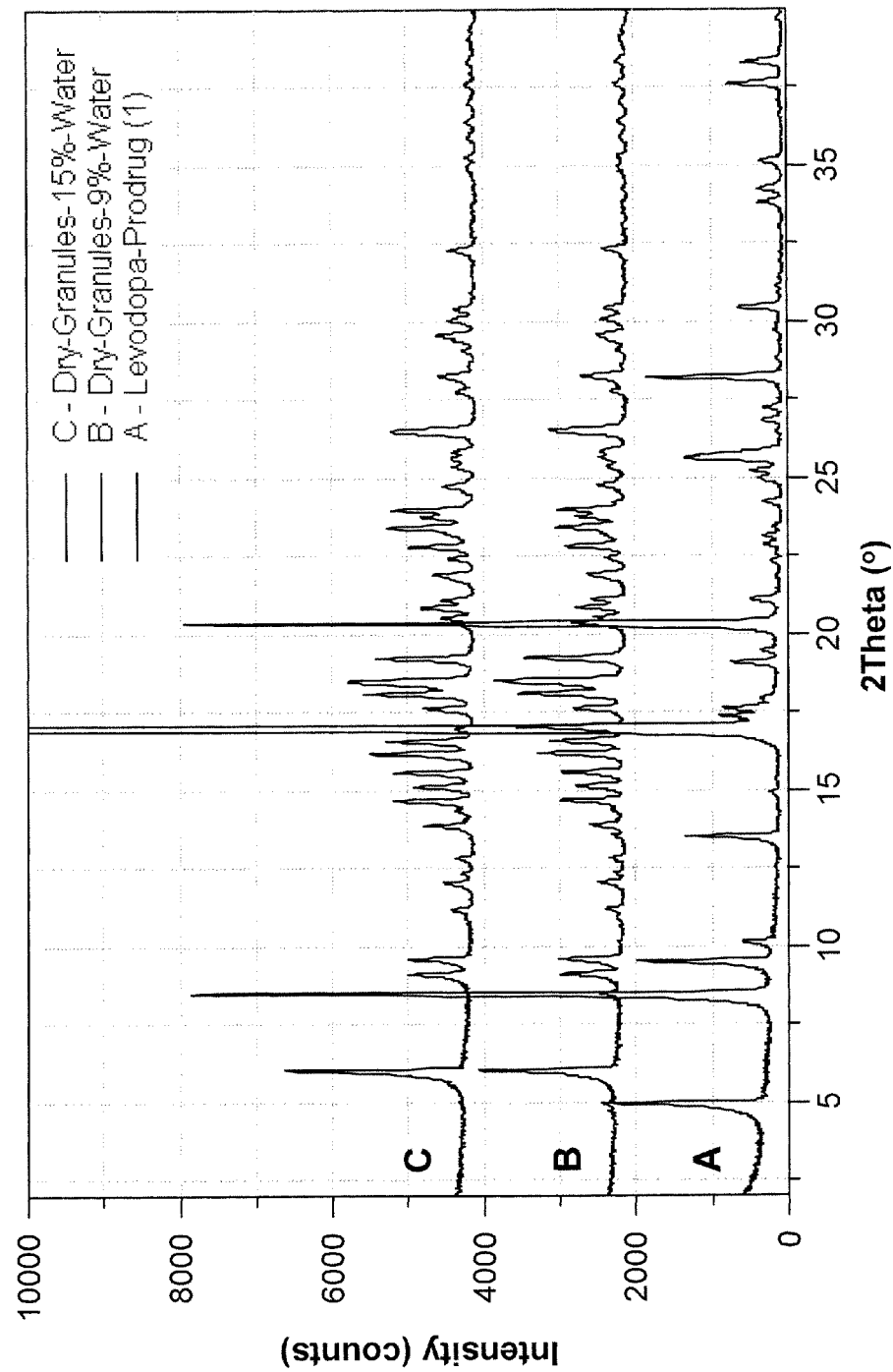
FIG. 3 shows PXRD patterns for (2R)-2-phenylcarbonyloxypropyl (2S)-2-amino-3-(3,4-dihydroxyphenyl)propanoate, mesylate and for granules comprising (2R)-2-phenylcarbonyloxypropyl (2S)-2-amino-3-(3,4-dihydroxyphenyl)propanoate, mesylate prepared using different amounts of water during high shear wet granulation.

In certain embodiments, crystalline (2R)-2-phenylcarbonyloxypropyl (2S)-2-amino-3-(3,4-dihydroxyphenyl)propanoate mesylate, hydrate is characterized by a powder X-ray powder diffraction pattern having characteristic scattering angles measured using Cu—K$_\alpha$ radiation (° 2θ) at least at 6.0°±0.2°, 9.1°±0.2°, 9.6°±0.2°, 12.0°±0.2°, 13.8°±0.2°, 14.6°±0.2°, 15.1°±0.2°, 15.6°±0.2°, 16.1°±0.2°, 16.6°±0.2°, 17.6°±0.2°, 18.5°±0.2°, and 19.2°±0.2°. In certain embodiments, crystalline (2R)-2-phenylcarbonyloxypropyl (2S)-2-amino-3-(3,4-dihydroxyphenyl)propanoate mesylate, hydrate is characterized by a powder X-ray diffraction pattern having characteristic scattering angles measured using Cu—K$_\alpha$ radiation (° 2θ) at least at 6.0°±0.2°, 9.1°±0.2°, 9.6°±0.2°, 12.0°±0.2°, 13.8°±0.2°, 14.6°±0.2°, 15.1°±0.2°, 15.6°±0.2°, 16.1°±0.2°, 16.6°±0.2°, 17.6°±0.2°, 18.5°±0.2°, 19.2°±0.2°, 20.8°±0.2°, 21.9°±0.2°, 22.8°±0.2°, 23.4°±0.2°, 23.7°±0.2°, 23.9°±0.2°, and 26.5°±0.2°. In certain embodiments, crystalline (2R)-2-phenylcarbonyloxypropyl (2S)-2-amino-3-(3,4-dihydroxyphenyl)propanoate mesylate, hydrate is characterized by a powder X-ray diffraction pattern having characteristic scattering angles measured using Cu—K$_\alpha$ radiation (° 2θ) at least at 6.0°±0.2°, 9.1°±0.2°, 9.6°±0.2°, 11.2°±0.2°, 12.0°±0.2°, 12.8°±0.2°, 13.8°±0.2°, 14.3°±0.2°, 14.6°±0.2°, 15.1°±0.2°, 15.6°±0.2°, 16.1°±0.2°, 16.6°±0.2°, 17.6°±0.2°, 18.5°±0.2°, 18.7°±0.2°, 19.2°±0.2°, 20.5°±0.2°, 20.8°±0.2°, 21.1°±0.2°, 21.9°±0.2°, 22.8°±0.2°, 23.4°±0.2°, 23.7°±0.2°, 23.9°±0.2°, 24.7°±0.2°, 26.5°±0.2°, 28.2°±0.2°, 28.3°±0.2°, and 29.5°±0.2°. PXRD patterns of crystalline (2R)-2-phenylcarbonyloxypropyl (2S)-2-amino-3-(3,4-dihydroxyphenyl)propanoate mesylate, hydrate are shown in FIG. 3 (pattern C). The crystalline hydrate may be formed during processing such as during high shear wet granulation or during exposure to certain temperature and humidity conditions.

It has been determined that adding a small amount of an alkylsulfate or pharmaceutically acceptable salt thereof to a pharmaceutical composition can control or prevent the conversion of anhydrous crystalline (2R)-2-phenylcarbonyloxypropyl (2S)-2-amino-3-(3,4-dihydroxyphenyl)propanoate, mesylate to the hydrated form. Accordingly, pharmaceutical compositions and oral dosage forms provided by the present disclosure comprise, in addition to crystalline (2R)-2-phenylcarbonyloxypropyl (2S)-2-amino-3-(3,4-dihydroxyphenyl)propanoate, mesylate, a $C_{6-18}$ alkylsulfate or pharmaceutically acceptable salt thereof. In certain embodiments, a $C_{6-18}$ alkylsulfate or pharmaceutically acceptable salt thereof is a $C_{8-16}$ alkylsulfate or pharmaceutically acceptable salt thereof, and in certain embodiments a $C_{10-14}$ alkylsulfate or pharmaceutically acceptable salt thereof. In certain embodiments, the $C_{6-18}$ alkylsulfate or pharmaceutically acceptable salt thereof is a salt of lauryl sulfate ($C_{12}$ alkylsulfate), and in certain embodiments, is sodium lauryl sulfate. In certain embodiments, the amount of a $C_{6-18}$ alkylsulfate or pharmaceutically acceptable salt thereof in a pharmaceutical composition is greater than about 0.5 wt-%, where wt-% is based on the total dry weight of the composition. In certain embodiments, the amount of $C_{6-18}$ alkylsulfate or pharmaceutically acceptable salt thereof in a pharmaceutical composition or oral dosage form can range from about 0.5 wt-% to about 2.0 wt-%, from about 0.5 wt-% to about 1.5 wt-%, and in certain embodiments is about 0.6 wt-% to about 0.9 wt-%. The amount of $C_{6-18}$ alkylsulfate or pharmaceutically acceptable salt thereof is sufficient to control or prevent conversion of anhydrous crystalline (2R)-2-phenylcarbonyloxypropyl (2S)-2-amino-3-(3,4-dihydroxyphenyl)propanoate, mesylate to a hydrated form.

In certain embodiments, the pharmaceutical compositions and oral dosage forms provided by the present disclosure may further comprise one or more pharmaceutically acceptable excipients.

In certain embodiments, the pharmaceutical composition comprises about 50 wt-% to about 90 wt-% crystalline (2R)-2-phenylcarbonyloxypropyl (2S)-2-amino-3-(3,4-dihydroxyphenyl)propanoate mesylate; about 0.5 wt-% to about 2.0 wt-% $C_{6-18}$ alkylsulfate or pharmaceutically acceptable salt thereof; about 6 wt-% to about 20 wt-% hydroxypropylmethylcellulose; and about 0.5 wt-% to about 2.0 wt-% magnesium stearate; wherein wt-% is based on the total dry weight of the composition. In certain embodiments, the pharmaceutical composition comprises about 80 wt-% to about 90 wt-% crystalline (2R)-2-phenylcarbonyloxypropyl (2S)-2-amino-3-(3,4-dihydroxyphenyl)propanoate mesylate; about 0.5 wt-% to about 1.0 wt-% $C_{6-18}$ alkylsulfate or pharmaceutically acceptable salt thereof; about 6 wt-% to about 10 wt-% hydroxypropylmethylcellulose; and about 0.5 wt-% to about 2.0 wt-% magnesium stearate; wherein wt-% is based on the total dry weight of the composition.

As disclosed in U.S. application Ser. No. 12/581,810, filed on Oct. 19, 2009 (U.S. Application Publication No. 2010/0099761) and in Example 3 herein, high shear wet granulation processing of anhydrous crystalline (2R)-2-phenylcarbonyloxypropyl (2S)-2-amino-3-(3,4-dihydroxyphenyl)propanoate, mesylate results in conversion to crystalline (2R)-2-phenylcarbonyloxypropyl (2S)-2-amino-3-(3,4-dihydroxyphenyl)propanoate, mesylate, hydrate. As demonstrated in Example 6, the addition of a small amount of sodium lauryl sulfate to the high shear wet granulation formulation controls or prevents conversion of anhydrous crystalline (2R)-2-phenylcarbonyloxypropyl (2S)-2-amino-3-(3,4-dihydroxyphenyl)propanoate, mesylate to the hydrated form. The use of anionic surfactants to control solid-state phase transformations in general (Davey et al., *J Am Chem Soc* 1997, 119, 1767-1772; and Ataab et al., *Adv Mater* 1990, 2(1), 40-43) and during high shear wet granulation (Airaksinen et al., *AAPS PharmSciTech* 2005, 6(2), E311-E322; and Wikstrom et al., *Pharmaceutical Research* 2008, 25(4), 923-935) is known in the art.

Oral dosage forms provided by the present disclosure comprise crystalline (2R)-2-phenylcarbonyloxypropyl (2S)-2-amino-3-(3,4-dihydroxyphenyl)propanoate, mesylate, and a $C_{6-18}$ alkylsulfate or pharmaceutically acceptable salt thereof. In certain embodiments, dosage forms may be capsules or tablets. In certain embodiments, an oral dosage form comprises granules, wherein the granules comprise crystalline (2R)-2-phenylcarbonyloxypropyl (2S)-2-amino-3-(3,4-dihydroxyphenyl)propanoate mesylate; and a $C_{6-18}$ alkylsulfate or pharmaceutically acceptable salt thereof. In certain embodiments of oral dosage forms and granules, a $C_{6-18}$ alkylsulfate or pharmaceutically acceptable salt thereof is a $C_{8-16}$ alkylsulfate or pharmaceutically acceptable salt thereof, and in certain embodiments a $C_{10-14}$ alkylsulfate or pharmaceutically acceptable salt thereof. In certain embodiments, the $C_{6-18}$ alkylsulfate or pharmaceutically acceptable salt thereof is a salt of lauryl sulfate ($C_{12}$ alkylsulfate), and in certain embodiments, is sodium lauryl sulfate. In certain embodiments, the granules comprise about 90 wt-% to about 99 wt-% crystalline (2R)-2-phenylcarbonyloxypropyl (2S)-2-amino-3-(3,4-dihydroxyphenyl)propanoate mesylate; and about 0.5 wt-% to about 2 wt-% $C_{6-18}$ alkylsulfate or pharmaceutically acceptable salt thereof; wherein wt-% is based on the total dry weight of the granules. In certain embodiments, granules comprise about 90 wt-% to about 99 wt-% crystalline (2R)-2-phenylcarbonyloxypropyl (2S)-2-amino-3-(3,4-dihydroxyphenyl)propanoate mesylate; and about 0.5 wt-% to about 1 wt-% sodium lauryl sulfate; wherein wt-% is based on the total dry weight of the granules.

Granules comprising crystalline (2R)-2-phenylcarbonyloxypropyl (2S)-2-amino-3-(3,4-dihydroxyphenyl)propanoate, mesylate, and a $C_{6-18}$ alkylsulfate or pharmaceutically acceptable salt thereof can be prepared using high shear wet granulation. To prepare granules crystalline (2R)-2-phenylcarbonyloxypropyl (2S)-2-amino-3-(3,4-dihydroxyphenyl)propanoate, mesylate, and a $C_{6-18}$ alkylsulfate or pharmaceutically acceptable salt thereof are combined with water. In certain embodiments, the amount of water added during high shear wet granulation is about 6 wt-% to about 10 wt-%, in certain embodiments, about 7 wt-% to about 10 wt-%, and in certain embodiments, about 7 wt-% to about 9 wt-%, where wt-% is based on the total weight of the water and dry materials added during high shear wet granulation.

Dosage forms comprising granules may comprise a suspension in which granules comprising crystalline (2R)-2-phenylcarbonyloxypropyl (2S)-2-amino-3-(3,4-dihydroxyphenyl)propanoate mesylate are dispersed in a pharmaceutically acceptable solvent formulation. Solvent formulations may include water, ethanol, flavorings, colorings, or combinations of any of the foregoing. Liquid oral dosage forms can include aqueous and non-aqueous solutions, emulsions, suspensions, and solutions and/or suspensions reconstituted from non-effervescent granules, containing suitable solvents, emulsifying agents, suspending agents, diluents, sweeteners, coloring agents, and flavoring agents, preservatives, and combinations of any of the foregoing. The solvent of an aqueous-based orally acceptable pharmaceutical carrier is entirely or predominantly water and can include a suspending agent. Examples of carriers include aqueous solutions, syrups, elixirs, dispersions, suspensions, emulsions such as oil-in-water emulsions, and microemulsions. Examples of suspending agents include microcrystalline cellulose/sodium carboxymethyl cellulose, guar gum, and the like. Co-solvents useful to solubilize and incorporate water-insoluble ingredients into a suspension include propylene glycol, glycerin, sorbitol solution, and the like. In addition, a liquid formulation may include vehicles such as wetting agents, emulsifying and suspension agents, sweetening, flavoring, coloring, perfuming, and preserving agents. Examples of useful suspension agents include ethoxylated isostearyl alcohols, polyoxyethylene sorbitol and sorbitan esters, microcrystalline cellulose, aluminum metahydroxide, bentonite, agar-agar, tragacanth, and combinations of any of the foregoing.

In certain embodiments, an oral dosage form comprises about 50 wt-% to about 90 wt-% crystalline (2R)-2-phenylcarbonyloxypropyl (2S)-2-amino-3-(3,4-dihydroxyphenyl)propanoate mesylate; about 0.5 wt-% to about 2.0 wt-% $C_{6-18}$ alkylsulfate or pharmaceutically acceptable salt thereof; about 6 wt-% to about 20 wt-% hydroxypropylmethylcellulose; and about 0.5 wt-% to about 2.0 wt-% magnesium stearate; wherein wt-% is based on the total dry weight of the dosage form. In certain embodiments, the oral dosage form comprises about 80 wt-% to about 90 wt-% crystalline (2R)-2-phenylcarbonyloxypropyl (2S)-2-amino-3-(3,4-dihydroxyphenyl)propanoate mesylate; about 0.5 wt-% to about 1.0 wt-% $C_{6-18}$ alkylsulfate or pharmaceutically acceptable salt thereof; about 6 wt-% to about 10 wt-% hydroxypropylmethylcellulose; and about 0.5 wt-% to about 2.0 wt-% magnesium stearate; wherein wt-% is based on the total dry weight of the dosage form.

In certain embodiments, an oral dosage form is a multilayer tablet such as a bilayer tablet where the layer comprising crystalline (2R)-2-phenylcarbonyloxypropyl (2S)-2-amino-3-(3,4-dihydroxyphenyl)propanoate mesylate comprises about 50 wt-% to about 90 wt-% crystalline (2R)-2-phenylcarbonyloxypropyl (2S)-2-amino-3-(3,4-dihydroxyphenyl) propanoate mesylate; about 0.5 wt-% to about 2.0 wt-% $C_{6-18}$ alkylsulfate or pharmaceutically acceptable salt thereof; about 6 wt-% to about 20 wt-% hydroxypropylmethylcellulose; and about 0.5 wt-% to about 2.0 wt-% magnesium stearate; wherein wt-% is based on the total dry weight of the layer composition. In certain embodiments, an oral dosage form is a multilayer tablet such as a bilayer tablet where the layer comprising crystalline (2R)-2-phenylcarbonyloxypropyl (2S)-2-amino-3-(3,4-dihydroxyphenyl)propanoate mesylate comprises about 80 wt-% to about 90 wt-% crystalline (2R)-2-phenylcarbonyloxypropyl (2S)-2-amino-3-(3,4-dihydroxyphenyl)propanoate mesylate; about 0.5 wt-% to about 1.0 wt-% $C_{6-18}$ alkylsulfate or pharmaceutically acceptable salt thereof; about 6 wt-% to about '0 wt-% hydroxypropylmethylcellulose; and about 0.5 wt-% to about 2.0 wt-% magnesium stearate; wherein wt-% is based on the total dry weight of the layer composition.

In certain embodiments, dosage forms may be in the form of tablets. In certain embodiments, granules and optional vehicles may be compressed into a tablet using conventional tableting equipment and standard techniques. Techniques and compositions for making tablets (compressed and molded), capsules (hard and soft gelatin), and pills are known in the art. When granules are incorporated into tablets, the granules may be compressed so as not to break. Disintegrants may be included in tablets comprising controlled release particles to facilitate release and/or dissolution of the granules from the tablet following ingestion. Tablet dosage forms may be of any shape suitable for oral administration of a drug such as spheroidal, cube-shaped oval, or ellipsoidal. In certain embodiments, tablet dosage forms provided by the present disclosure are matrix systems in which crystalline (2R)-2-phenylcarbonyloxypropyl (2S)-2-amino-3-(3,4-dihydroxyphenyl)propanoate, mesylate and a $C_{6-18}$ alkylsulfate or pharmaceutically acceptable salt thereof is dispersed in a matrix comprising at least one release-rate modifying compound. Matrix systems are well-known in the art. Tablet dosage forms may also be bilayer tablets in which a first layer comprises crystalline (2R)-2-phenylcarbonyloxypropyl (2S)-2-amino-3-(3,4-dihydroxyphenyl)propanoate mesylate and $C_{6-18}$ alkylsulfate or pharmaceutically acceptable salt thereof such as sodium lauryl sulfate, and the second layer comprises another pharmaceutically useful compound such as an L-aromatic amino acid decarboxylase inhibitor such as carbidopa, a catechol-O-methyltransferase inhibitor, or a combination of an L-aromatic amino acid decarboxylase inhibitor and a catechol-O-methyltransferase inhibitor.

Release rate modifying compounds can retard the release of a pharmaceutical composition from a dosage form. Examples of release rate modifying compounds include, but are not limited to, pH dependent release polymers, pH independent release polymers, hydrophilic polymers that have a high degree of swelling when in contact with water or aqueous media, polymers that form a gel on contact with water or aqueous media, polymers that exhibit both swelling and gelling characteristics in contact with water or aqueous media, fatty compounds such as waxes, and biodegradable polymers.

Examples of pH dependent release rate modifying polymers useful in tablet dosage forms provided by the present disclosure include acrylic acid and methacrylic acid polymers and copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymers, polyacrylamide, aminoalkyl methacrylate copolymer, poly(methacrylic acid anhydride), glycidyl methacrylate co-polymers, ammonioalkyl methacrylate copolymers, and combinations of any of the foregoing. In certain embodiments, a pH dependent polymer may be a copolymer synthesized from diethylaminoethyl methacrylate and other neutral methacrylic esters, also known as methacrylic acid copolymers or polymer methacrylates, commercially available as Eudragit® (Rohm Pharma).

Examples of pH independent release polymers useful in tablet dosage forms provided by the present disclosure include ammonioalkyl methacrylate copolymers such as Eudragit® RS and Eudragit® RL, which are acrylic resins comprising copolymers of acrylic and methacrylic acid esters with a low content of quaternary ammonium groups.

Examples of hydrophilic release rate modifying polymers that exhibit a high degree of swelling useful in tablet dosage forms provided by the present disclosure include cross linked sodium carboxymethylcellulose, cross-linked hydroxypropylcellulose, high-molecular weight hydroxypropylmethylcellulose, carboxymethylamide, potassium methacrylatedivinylbenzene co-polymer, polymethylmethacrylate, polyvinylpyrrolidone, high-molecular weight polyvinylalcohols, methyl cellulose, vinyl acetate copolymers, and combinations of any of the foregoing. In certain embodiments of tablets provided by the present disclosure a composition comprising crystalline (2R)-2-phenylcarbonyloxypropyl (2S)-2-amino-3-(3,4-dihydroxyphenyl)propanoate, mesylate, and a $C_{6-18}$ alkylsulfate or pharmaceutically acceptable salt thereof comprises about 6 wt-% to about 10 wt-% hydroxypropylmethyl cellulose, in certain embodiments, about 7 wt-% to about 9 wt-% hydroxypropylmethyl cellulose, in certain embodiments, about 8 wt-% hydroxypropylmethyl cellulose. In certain embodiments, the hydroxypropylmethyl cellulose comprises HPMC K100M.

Examples of release rate-modifying polymers that gel in contact with water useful in tablet dosage forms provided by the present disclosure include methylcellulose, carboxymethylcellulose, low-molecular weight hydroxypropylmethylcellulose, low-molecular weight polyvinylalcohols, polyoxyethyleneglycols, non-cross linked polyvinylpyrrolidone, xanthan gum, and combinations of any of the foregoing.

Examples of release rate-modifying polymers that exhibit both swelling and gelling properties useful in tablet dosage forms provided by the present disclosure include medium-viscosity hydroxypropylmethylcellulose and medium-viscosity polyvinylalcohols.

In certain embodiments, release rate-modifying compounds useful in tablet dosage forms provided by the present disclosure may be chosen from glyceryl esters such as glyceryl monostearate, glyceryl behenate, glyceryl palmitostearate, lauroyl macrogol glyceride, stearoyl macrogol glyceride, and combinations of any of the foregoing. Other fatty and/or waxy release rate-modifying compounds include lauryl alcohol, myristyl alcohol, stearyl alcohol, cetyl alcohol, cetostearyl alcohol, palmitoyl alcohol, ouricury wax, hydrogenated vegetable oil, candelilla wax, esparto wax, stearic acid, paraffin wax, beeswax, glycowax, castor wax, carnauba wax, and combinations of any of the foregoing.

Examples of bioerodible polymers include collagen, gelatin, polyvinyl alcohols, polyorthoesters, polyacetyls, polyorthocarbonates, polyamides, polyaminoacids, polyesters, polylactic acids, polyglycolic acids, polycarbohydrates, polyorthoesters, polyorthocarbonates, polyacetyls, polyanhydrides, polydehydropyrans, polydioxinones, and combinations of any of the foregoing.

Other useful release-rate modifying compounds that may be incorporated into tablet dosage forms provided by the present disclosure include hydrocolloids such as natural or synthetic gums, carbohydrate-based substances such as acacia, gum tragacanth, locust bean gum, guar gum, agar, pectin, carageenin, soluble and insoluble alginates, carboxypolymethylene, casein, zein, polyethylene oxide, maleic anhydride/methyl vinyl ether copolymers, and proteinaceous substances such as gelatin.

Release rate modifying polymers or compounds may be used alone or in combination with one or more other release rate-modifying polymers or compounds and/or can be a copolymer of more than one release rate modifying polymer.

Tablet dosage forms comprising a crystalline (2R)-2-phenylcarbonyloxypropyl (2S)-2-amino-3-(3,4-dihydroxyphenyl)propanoate mesylate and a $C_{6-18}$ alkylsulfate or pharmaceutically acceptable salt thereof and one or more release rate modifying compounds may be prepared using standard techniques well known in the art such as high shear wet granulation, fluid-bed granulation, dry granulation, and direct compression. In wet granulation, specified quantities of drug and one or more vehicles are mixed using a mechanical powder blender or mixer until uniform. A liquid binder is added to the powder mixture to facilitate adhesion of the powder particles. The wet mass is pressed through a sieve to provide granules, which are then dried. The dried granules are passed through a screen to reduce the particle size. A dry lubricant is added to the dried granulate and the resulting blend compressed into tablets. In fluid-bed granulation, particles comprising a drug are suspended in an air stream. A solution comprising a granulating material is sprayed into the air stream to coat the particles. After drying and the addition of vehicles, the granulated material is compressed into tablets. In dry granulation, the drug and vehicles such as binder, diluent, and/or lubricant is blended and compressed by roller compaction or slugging. The compressed material is sieved through a mesh screen to provide granules. Additional vehicles may be blended with the granules and the blend compressed into tablets. Tablets may also be formed by direct compression of compounds having sufficient coadhesive properties.

Matrix systems in which crystalline (2R)-2-phenylcarbonyloxypropyl (2S)-2-amino-3-(3,4-dihydroxyphenyl)propanoate mesylate and a $C_{6-18}$ alkylsulfate or pharmaceutically acceptable salt thereof is dispersed in a matrix comprising at least one release rate modifying compound may be prepared by dry blending a release-modifying polymer, filler, crystalline (2R)-2-phenylcarbonyloxypropyl (2S)-2-amino-3-(3,4-dihydroxyphenyl)propanoate mesylate, and vehicles followed by granulating the mixture using an alcohol until proper granulation is obtained. Granulation may be accomplished by methods known in the art. The wet granules may be dried in a fluid bed dryer, sifted, and ground to an appropriate size. Lubricating agents may be mixed with the dried granulation to obtain a final formulation. In certain embodiments, such formulations may be compressed into tablet dosage forms by methods well known in the art.

In certain embodiments, the amount of crystalline (2R)-2-phenylcarbonyloxypropyl (2S)-2-amino-3-(3,4-dihydroxyphenyl)propanoate mesylate in tablet dosage forms ranges from about 1 mg to about 400 mg, in certain embodiments, from about 1 mg to about 200 mg, and in certain embodiments, from about 50 mg to about 100 mg. The amount of levodopa in a dosage from comprising crystalline (2R)-2-phenylcarbonyloxypropyl (2S)-2-amino-3-(3,4-dihydroxyphenyl)propanoate mesylate corresponds to the mass equivalent weight of levodopa in the dosage form. For reference, 1.00 mg of crystalline (2R)-2-phenylcarbonyloxypropyl (2S)-2-amino-3-(3,4-dihydroxyphenyl)propanoate mesylate contains about 0.43 mg equivalents of levodopa. In certain embodiments, tablet dosage forms may comprise a therapeutically effective amount of crystalline (2R)-2-phenylcarbonyloxypropyl (2S)-2-amino-3-(3,4-dihydroxyphenyl)propanoate mesylate. In certain embodiments in which tablet dosage forms comprise less than a therapeutically effective amount of crystalline (2R)-2-phenylcarbonyloxypropyl (2S)-2-amino-3-(3,4-dihydroxyphenyl)propanoate mesylate, multiple tablet dosage forms may be administered to a patient simultaneously, or over a period of time to provide a therapeutically effective amount of crystalline (2R)-2-phenylcarbonyloxypropyl (2S)-2-amino-3-(3,4-dihydroxyphenyl)propanoate mesylate.

In addition to crystalline (2R)-2-phenylcarbonyloxypropyl (2S)-2-amino-3-(3,4-dihydroxyphenyl)propanoate mesylate and a $C_{6-18}$ alkylsulfate or pharmaceutically acceptable salt thereof, tablet dosage forms may also comprise one or more pharmaceutically acceptable vehicles such as surfactants, lubricants, binding agents, diluents, anti-adherents, glidants, buffers, dyes, wetting agents, emulsifying agents, pH buffering agents, stabilizing agents, thickening agents, disintegrants, and coloring agents.

Diluents, or fillers, may be added to increase the bulk to make dosage forms a practical size for compression. Examples of diluents useful in tablet dosage forms provided by the present disclosure include dibasic calcium phosphate, dibasic calcium phosphate dihydrate, calcium sulfate, dicalcium phosphate, tricalcium phosphate, lactose, cellulose including microcrystalline cellulose, kaolin, mannitol, sodium chloride, dry starch, pregelatinized starch, compressible sugar, mannitol such as Pearlitol® 100SD and Perlitol® 50° C., and combinations of any of the foregoing. In certain embodiments, a diluent is selected from dibasic calcium phosphate and microcrystalline cellulose. Fillers may be water insoluble, water soluble, or combinations thereof. Examples of useful water insoluble fillers include silicon dioxide, titanium dioxide, talc, alumina, starch, kaolin, polacrilin potassium, powdered cellulose, microcrystalline cellulose, fumed silica, glyceryl monostearate, magnesium stearate, calcium stearate, colloidal silica, micronized silica, magnesium trisilicate, gypsum, and combinations of any of the foregoing. Examples of water-soluble fillers include water soluble sugars and sugar alcohols, such as lactose, glucose, fructose, sucrose, mannose, dextrose, galactose, the corresponding sugar alcohols and other sugar alcohols, such as mannitol, sorbitol, xylitol, and combinations of any of the foregoing. In certain embodiments, a dosage form comprises microcrystalline cellulose such as Avicel® MCC PH200 (FMC Biopolymer, Newark Del.). In certain embodiments wherein the diluent is microcrystalline cellulose, a tablet dosage form may comprise an amount of diluent ranging from about 1% w/w to about 60% w/w.

Glidants may be included in dosage forms provided by the present disclosure to reduce sticking effects during processing, film formation, and/or drying. Examples of useful glidants include talc, magnesium stearate, glycerol monostearate, colloidal silicon dioxide, precipitated silicon dioxide, fumed silicon dioxide, and combinations of any of the foregoing. In certain embodiments, a glidant is colloidal silicon dioxide. Dosage forms may comprise less than about 2% w/w of a glidant, and in certain embodiments, less than about 1% w/w of a glidant.

Binding agents may be included in dosage forms to facilitate adhesion of the constituents. Examples of binding agents useful in tablet dosage forms provided by the present disclosure include polyvinyl acetate phthalate, molasses, methylcellulose, carboxymethylcellulose, microcrystalline cellulose, hydroxypropylmethylcellulose, polyvinyl pyrrolidone, and combinations of any of the foregoing. In certain embodiments provided by the present disclosure, a binder is microcrystalline cellulose such as Avicel® MCC PH200 (FMC Biopolymers, Newark, Del.). In certain embodiments, the binder is hydroxypropylmethyl cellulose such as Methocel™ HPMC K4, Methocel™ HPMC K15M, Methocel™ HPMC K100M, Methocel™ HPMC E4M or combinations thereof (Dow Chemical, Midland, Mich.).

Lubricants and anti-adherents may be included in tablet dosage forms provided by the present disclosure to aid in processing. Examples of lubricants and/or anti-adherents useful in tablet dosage forms provided by the present disclosure include calcium stearate, glyceryl behenate, glyceryl monostearate, magnesium stearate, mineral oil, polyethylene glycol, sodium stearyl fumarate, sodium lauryl sulfate, sodium dodecyl sulfate, stearic acid, talc, hydrogenated vegetable oil, zinc stearate, and combinations of any of the foregoing. In certain embodiments, a lubricant is glyceryl monostearate. In certain embodiments, a lubricant is magnesium stearate such as magnesium stearate NF, EP Hyqual®, vegetable source (Mallinckrodt). Dosage forms may comprise an amount of lubricant and/or anti-adherent ranging from about 0.1% w/w to about 5% w/w, in certain embodiments, from about 0.1% w/w to about 2% w/w, and in certain embodiments, from about 0.1% w/w to about 1% w/w.

Examples of surfactants useful in tablet dosage forms provided by the present disclosure include pharmaceutically acceptable anionic surfactants, cationic surfactants, zwitterionic surfactants, amphoteric (amphiphatic/amphiphilic) surfactants, non-ionic surfactants, polyethyleneglycol esters or ethers, and combinations of any of the foregoing. Examples of useful pharmaceutically acceptable anionic surfactants include monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates such as sodium lauryl sulfate and sodium dodecyl sulfate, ethoxylated alkyl sulfates, ester linked sulfonates such as docusate sodium and dioctyl sodium succinate, alpha olefin sulfonates, phosphated ethoxylated alcohols, and combinations of any of the foregoing. Examples of useful pharmaceutically acceptable cationic surfactants include monoalkyl quaternary ammonium salts, dialkyl quaternary ammonium compounds, amidoamines, and aminimides. Examples of useful pharmaceutically acceptable amphoteric surfactants include N-substituted alkyl amides, N-alkyl betaines, sulfobetaines, and N-alkyl-6-aminopropionates. Examples of useful pharmaceutically acceptable polyethyleneglycol esters or ethers include polyethoxylated castor oil, polyethoxylated hydrogenated castor oil, and hydrogenated castor oil. In certain embodiments, a surfactant is sodium lauryl sulfate. In certain embodiments, dosage forms may comprise less than about 3% w/w of a surfactant, and in certain embodiments, less than about 2% w/w of a surfactant. In certain embodiments, a surfactant is a nonionic surfactant. In certain embodiments, a surfactant is a block copolymer of ethylene oxide and propylene oxide.

Disintegrants may be included in a tablet formulation to cause a tablet to break apart, for example, by expansion of a disintegrant when exposed to water. Examples of useful disintegrants include water swellable substances such as low-substituted hydroxypropyl cellulose, cross-linked sodium carboxymethylcellulose (sodium croscarmellose), sodium starch glycolate, sodium carboxymethylcellulose, sodium carboxymethyl starch, ion-exchange resins, microcrystalline cellulose, cross-linked polyvinyl pyrrolidone such as povidone, crospovidone, and Polyplasdone® XL-10, starches and pregelatinized starch, formalin-casein, alginic acid, certain complex silicates, and combinations of any of the foregoing.

Tablet dosage forms provided by the present disclosure may further comprise one or more coatings, which may partially or fully cover the tablets. While certain coatings may be applied to modify or affect the release of crystalline (2R)-2-phenylcarbonyloxypropyl (2S)-2-amino-3-(3,4-dihydroxyphenyl)propanoate mesylate from a dosage form in the gastrointestinal tract, others may have no such effect. For example, one or more additional coatings may be for physical protection, aesthetic considerations, ease in swallowing, identification, and/or to facilitate further processing of the particles. Coatings may be impermeable to moisture or moisture permeable. Moisture permeable exterior tablet coatings may be useful for maintaining low moisture content in a dosage form that is packaged in the presence of a desiccant and may thereby enhance, for example, the storage stability of a dosage form. Examples of materials useful in coatings for physical protection include permeable or soluble materials such as hydroxypropyl methylcellulose, hydroxypropyl cellulose, hydroxypropyl ethylcellulose, and xanthan gum. Examples of materials useful in external tablet coatings to facilitate further processing include talc, colloidal silica, polyvinyl alcohol, titanium dioxide, micronized silica, fumed silica, glycerol monostearate, magnesium trisilicate, and magnesium stearate. An external tablet coating may further include one or more vehicles such as plasticizers, binders, fillers, lubricants, compression aides, and combinations of any of the foregoing. The one or more additional coatings may comprise a single material or a combination of more than one material including any of those disclosed herein. These additional coatings may be applied to tablet dosage forms by methods known to those skilled in the art.

It is generally accepted that commercially acceptable tablets have a friability of less than about 1 wt-% determined according to USP Test No. 1216. In certain embodiments, tablets provided by the present disclosure have a friability of less than about 1 wt-%, in certain embodiments, less than about 0.5 wt-%, in certain embodiments, less than about 0.3 wt-%, and in certain embodiments, less than about 0.2 wt-%.

In certain embodiments, dosage forms provided by the present disclosure are substantially free of lactam side products formed by intramolecular cyclization of crystalline (2R)-2-phenylcarbonyloxypropyl (2S)-2-amino-3-(3,4-dihydroxyphenyl)propanoate mesylate and/or levodopa. Dosage forms may be stable to extended storage, such as for example, greater than one year, without substantial lactam formation such as less than 0.5% lactam by weight, less than 0.2% lactam by weight, or less than 0.1% lactam by weight.

Sustained release dosage forms comprising crystalline (2R)-2-phenylcarbonyloxypropyl (2S)-2-amino-3-(3,4-dihydroxyphenyl)propanoate, mesylate and a $C_{6-18}$ alkylsulfate or pharmaceutically acceptable salt thereof exhibit enhanced oral bioavailability as levodopa compared to the oral bioavailability of levodopa when administered in an equivalent dosage form of levodopa and/or racemate. The enhanced oral bioavailability of levodopa prodrug is believed to be due the efficient absorption of levodopa prodrug throughout the gastrointestinal tract, including the colon, via active and/or passive transport mechanisms. Dosage forms provided by the present disclosure provide for the release of crystalline (2R)-2-phenylcarbonyloxypropyl (2S)-2-amino-3-(3,4-dihydroxyphenyl)propanoate mesylate from the dosage form during passage of the dosage form throughout the gastrointestinal tract.

Following oral administration to a patient, sustained release dosage forms provided by the present disclosure provide levodopa in the systemic circulation of a patient. Crystalline (2R)-2-phenylcarbonyloxypropyl (2S)-2-amino-3-(3,4-dihydroxyphenyl)propanoate, mesylate may be absorbed from the gastrointestinal tract and enter the systemic circulation where the promoiety is cleaved to release levodopa. The promoiety may be cleaved from crystalline (2R)-2-phenylcarbonyloxypropyl (2S)-2-amino-3-(3,4-dihydroxyphenyl)propanoate, mesylate to release levodopa in the gastrointestinal tract following which levodopa can be absorbed into the systemic circulation. The promoiety of crystalline (2R)-2-phenylcarbonyloxypropyl (2S)-2-amino-3-(3,4-dihydroxyphenyl)propanoate, mesylate may be cleaved either chemically and/or enzymatically. For example, one or more enzymes, such as esterases, present in the intestinal lumen, intestinal tissue, blood, liver, brain, or any other suitable tissue of a mammal can enzymatically cleave the promoiety of crystalline (2R)-2-phenylcarbonyloxypropyl (2S)-2-amino-3-(3,4-dihydroxyphenyl)propanoate mesylate.

When administered orally to a patient, i.e., by a patient swallowing a dosage form provided by the present disclosure, a sustained therapeutically effective concentration of levodopa in the blood of the patient during a continuous period of time. In certain embodiments, dosage forms may provide a concentration of levodopa in the blood of a patient that is greater than a minimum therapeutically effective concentration and less than a minimum adverse concentration of levodopa in the blood of the patient. In certain embodiments, dosage forms provided by the present disclosure provide therapeutically effective concentrations levodopa in the blood of a patient for a continuous period of time without exceeding the minimum adverse concentration of levodopa. In certain embodiments, the concentration of levodopa in the blood of a patient does not exceed a minimum adverse concentration at any time after the dosage form is orally administered to the patient. Dosage forms provided by the present disclosure can provide a therapeutically effective concentration of levodopa in the blood of a patient for a continuous period of time while reducing or eliminating adverse drug effects associated with the high blood concentrations of levodopa, e.g., at concentrations above the minimum adverse concentration, observed following oral dosing of levodopa dosage forms. The high bioavailability of levodopa achievable using dosage forms comprising crystalline (2R)-2-phenylcarbonyloxypropyl (2S)-2-amino-3-(3,4-dihydroxyphenyl)propanoate, mesylate may facilitate the use of lower mass equivalents of levodopa in a dose to achieve a sustained therapeutically effective concentration of levodopa in the blood of a patient compared to the amount of levodopa in an oral dosage form comprising levodopa.

Dosage forms provided by the present disclosure are capable of providing a sustained therapeutically effective concentration of levodopa in the blood of a patient following oral administration. For example, dosage forms may provide a sustained therapeutically effective concentration of levodopa in the blood of a patient during a continuous time period selected from at least about 4 hours, at least about 8 hours, at least about 12 hours, at least about 16 hours, at least about 20 hours, or at least about 24 hours, after oral administration to a patient. In certain embodiments, the concentration of levodopa in the blood of a patient will not exceed a minimum adverse concentration at any time after the dosage form is orally administered to the patient, e.g., will not reach a concentration that causes adverse events in the particular patient. A therapeutically effective concentration of levodopa in the blood of a patient may range from about 1 µg/mL to about 100 µg/mL, from about 1 µg/mL to about 50 µg/mL, and in certain embodiments, from about 1 µg/mL to about 10 µg/mL.

The pharmacokinetic profile of the blood or plasma levodopa concentration can be characterized by a lower levodopa $C_{max}/C_4$ ratio, a lower levodopa $C_{max}/C_2$ ratio (where $C_{max}$ refers to the maximum levodopa concentration following administration, and $C_2$ and $C_4$ refer to the levodopa concentration at 2 hours and 4 hours following administration, respectively), and/or a lower $C_{max}$/dose, compared to immediate release dosage forms of levodopa, to certain other controlled release oral formulations comprising levodopa that provide a similar levodopa blood $AUC_{inf}$. In certain embodiments, pharmaceutical compositions and oral dosage forms provided by the present disclosure provide a levodopa $C_4/C_2$ value following oral administration to monkeys equal to or greater than about 0.25, equal to or greater than about 0.5, and in certain embodiments, equal to or greater than about 1.0.

A dosage regimen employing oral administration of dosage forms provided by the present disclosure may be developed to maintain a concentration of levodopa in the blood of a patient, which is greater than a minimum therapeutically effective concentration and less than a minimum adverse concentration for a prolonged period of time. In certain embodiments, a minimum therapeutically effective concentration of levodopa may range from about 1 µg/mL to about 100 µg/mL, from about 1 µg/mL to about 50 µg/mL, and in certain embodiments, from about 1 µg/mL to about 10 µg/mL. A minimum therapeutic concentration and a minimum adverse concentration will depend on a number of factors such as the disease being treated, the severity of the disease, the intended clinical outcome, the condition of the patient being treated, and so forth. Such regimens may employ repeated dosing of one or more dosage forms provided by the present disclosure. An appropriate interval of dosing may depend, for example, on the amount of crystalline (2R)-2-phenylcarbonyloxypropyl (2S)-2-amino-3-(3,4-dihydroxyphenyl)propanoate, mesylate contained in the dosage form, the composition of the dosage form, the release characteristics of the levodopa prodrug from the dosage form, the disease being treated, the condition of the patient, the potential adverse effects, and the judgment of the prescribing physician. Dosage regimens may include repeated administration of the same dosage form at each interval or different dosage forms at different intervals. For example, a twice-daily dosage regimen can include the administration of a first dosage form in the morning, and a second dosage form in the evening.

Dosage forms provided by the present disclosure include dosage forms that are bioequivalent to the dosage forms disclosed herein, in terms of both rate and extent of absorption, for example as defined by the U.S. Food and Drug Administration and discussed in "Guidance for Industry—Bioavailability and Bioequivalence Studies for Orally Administered Drug Products" (2003). Bioequivalence refers to equivalence of the rate and extent of absorption of crystalline (2R)-2-phenylcarbonyloxypropyl (2S)-2-amino-3-(3,4-dihydroxyphenyl)propanoate, mesylate after administration of equal doses of levodopa or crystalline (2R)-2-phenylcarbonyloxypropyl (2S)-2-amino-3-(3,4-dihydroxyphenyl)propanoate, mesylate to a patient. As used herein, two pharmacokinetic profiles are bioequivalent if the 90% confidence interval for the ratio of the mean response of the two profiles is within the limits of 0.8 and 1.25. The mean response includes at least one of the characteristic parameters of a profile such as $C_{max}$, $T_{max}$, and AUC.

Figure 4:
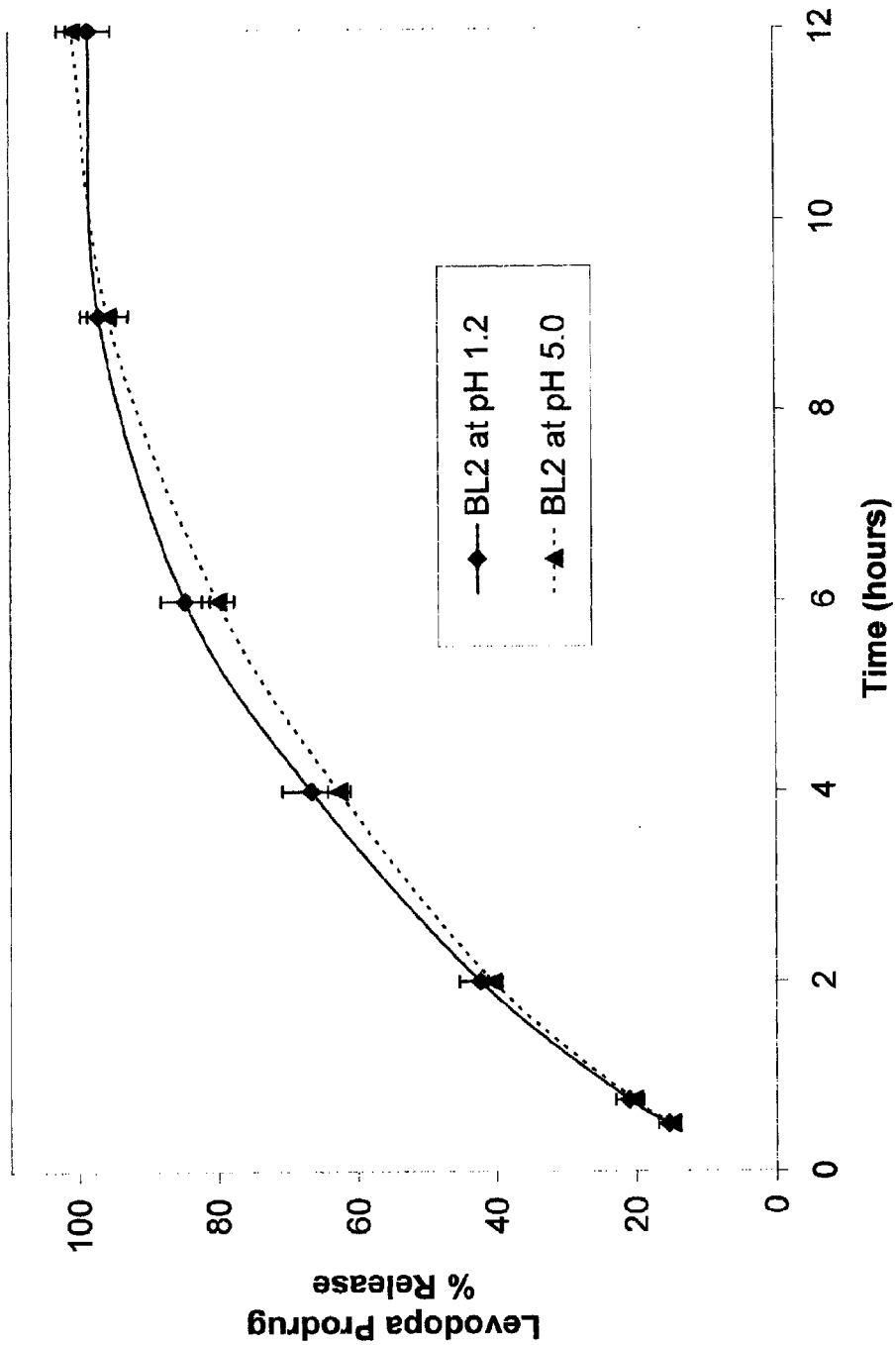
FIG. 4 shows the levodopa pharmacokinetic profile following oral administration of SR4 or SR5 tablets to fasted subjects.
Figure 5:
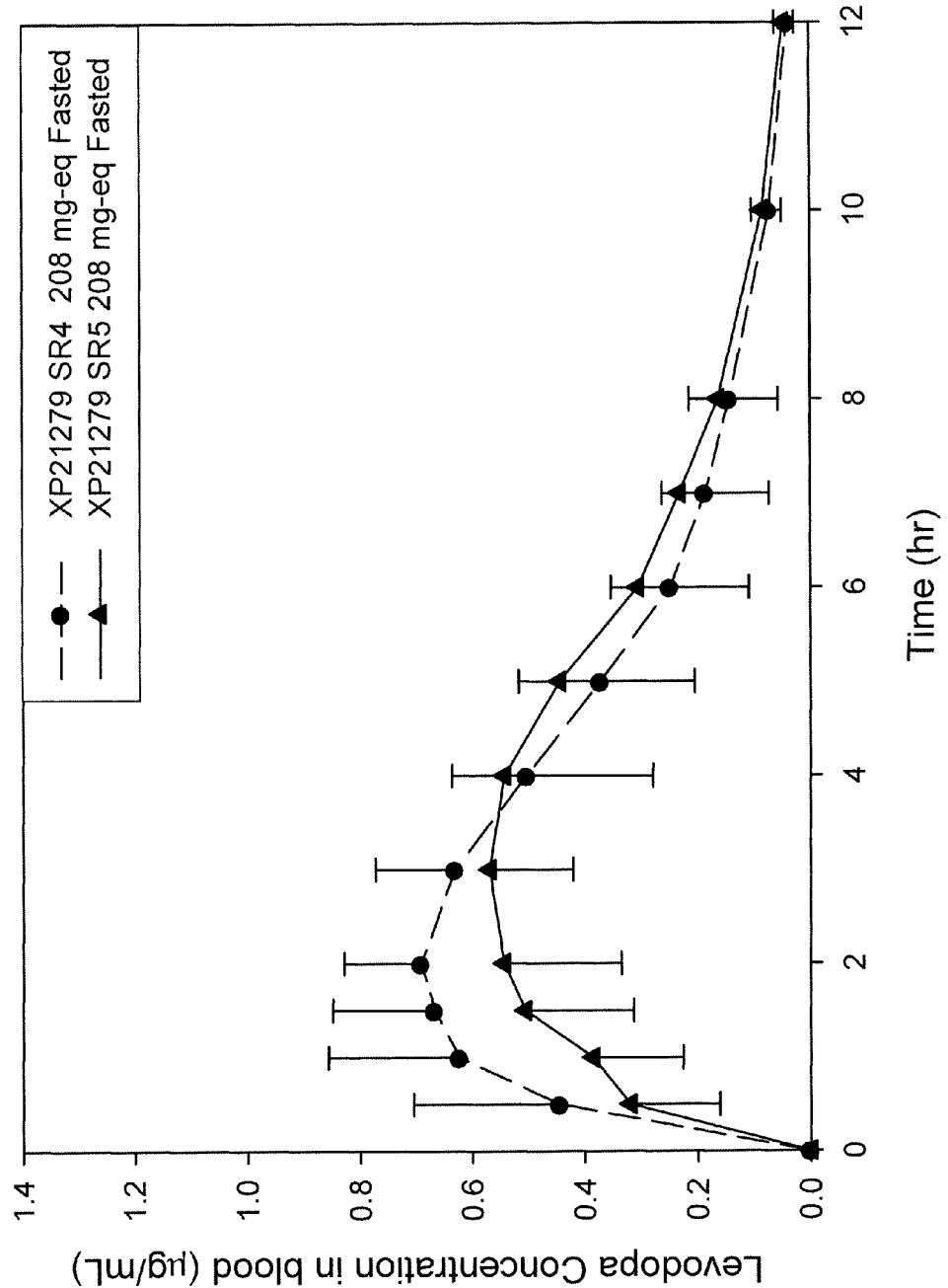
FIG. 5 shows the levodopa pharmacokinetic profile following oral administration of SR4 or SR5 tablets to fed subjects.

In certain embodiments, a single dose of oral tablet dosage forms provided by the present disclosure provide levodopa blood concentrations in blood as shown in Table 3, Table 4, FIG. 4, and/or FIG. 5. In certain embodiments, oral administration of a SR4 or SR5 tablet or tablets for a total dose of 360 mg levodopa prodrug (208 mg-equivalents levodopa) to (12) fed healthy adult human subjects provides a mean levodopa blood pharmacokinetic profile characterized by a $C_{max}$ of about 0.8±0.3 µg/mL; a $T_{max}$ of about 4.5±1.1 hours; a $C_8$ of about 0.38±0.15 µg/mL; a $T_{1/2}$ of about 2.5±0.9 hours; and an $AUC_{inf}$ of about 5.2±1.5 µg·hr/mL. In certain embodiments, oral administration of a SR4 or SR5 tablet or tablets for a total dose of 360 mg levodopa prodrug (208 mg-equivalents levodopa) to (12) feasted healthy adult human subjects provides a mean levodopa blood pharmacokinetic profile characterized by a $C_{max}$ of about 0.73±0.18 µg/mL; a $T_{max}$ of about 2.3±1.1 hours; a $C_8$ of about 0.15±0.08 µg/mL; a $T_{1/2}$ of about 2.7±0.6 hours; and an $AUC_{inf}$ of about 3.8±0.9 µg·hr/mL.

In certain embodiments, oral administration of a SR5 tablet or tablets for a total dose of 360 mg levodopa (208 mg-equivalents levodopa) to (12) fed healthy adult human subjects provides a mean levodopa blood pharmacokinetic profile where $C_1$ is about 0.14 µg/mL, $C_2$ is about 0.33 µg/mL, $C_4$ is about 0.56 µg/mL, $C_6$ is about 0.55 µg/mL, $C_8$ is about 0.34 µg/mL, and $C_{12}$ is about 0.13 µg/mL.

In certain embodiments, oral administration of a SR5 tablet or tablets for a total dose of 360 mg levodopa prodrug (208 mg-equivalents levodopa) to (12) fed healthy adult human subjects provides a mean levodopa blood pharmacokinetic profile where $C_1$ is from about 0.12 µg/mL to about 0.18 µg/mL; $C_2$ is from about 0.26 µg/mL to about 0.41 µg/mL; $C_4$ is from about 0.45 µg/mL to about 0.70 µg/mL; $C_6$ is from about 0.44 µg/mL to about 0.69 µg/mL; $C_8$ is from about 0.28 µg/mL to about 0.43 µg/mL; and $C_{12}$ is from about 0.10 µg/mL to about 0.16 µg/mL.

In certain embodiments, oral administration of a SR4 tablet or tablets for a total dose of 360 mg levodopa prodrug (208 mg-equivalents levodopa) to (12) fed healthy adult human subjects provides a mean levodopa blood pharmacokinetic profile where $C_1$ is about 0.18 µg/mL, $C_2$ is about 0.36 µg/mL, $C_4$ is about 0.65 µg/mL, $C_6$ is about 0.57 µg/mL, $C_8$ is about 0.38 µg/mL, and $C_{12}$ is about 0.09 µg/mL, where $C_1$, $C_2$, $C_4$, $C_6$, $C_8$, and C12 are the blood concentrations at 1, 2, 4, 6, 8, and 12 hours following dosing, respectively.

In certain embodiments, oral administration of a SR4 tablet or tablets for a total dose of 360 mg levodopa prodrug (208 mg-equivalents levodopa) to (12) fed healthy adult human subjects provides a mean levodopa blood pharmacokinetic profile where $C_1$ from about 0.14 µg/mL to about 0.23 µg/mL; $C_2$ is from about 0.28 µg/mL to about 0.44 µg/mL; $C_4$ is from about 0.52 µg/mL to about 0.81 µg/mL; $C_6$ is from about 0.46 µg/mL to about 0.72 µg/mL; $C_8$ is from about 0.31 µg/mL to about 0.48 µg/mL; and $C_{12}$ is from about 0.07 µg/mL to about 0.11 µg/mL.

In certain embodiments, oral administration of a SR5 tablet or tablets for a total dose of 360 mg levodopa prodrug (208 mg-equivalents levodopa) to (12) fasted healthy adult human subjects provides a mean levodopa blood pharmacokinetic profile where $C_1$ is about 0.39 µg/mL, $C_2$ is about 0.54 µg/mL, $C_4$ is about 0.54 µg/mL, $C_6$ is about 0.31 µg/mL, $C_8$ is about 0.16 µg/mL, and $C_{12}$ is about 0.05 µg/mL.

In certain embodiments, oral administration of a SR5 tablet or tablets for a total dose of 360 mg levodopa prodrug (208 mg-equivalents levodopa) to (12) fasted healthy adult human subjects provides a mean levodopa blood pharmacokinetic profile where $C_1$ is from about 0.31 µg/mL to about 0.48 µg/mL; $C_2$ is from about 0.43 µg/mL to about 0.68 µg/mL; $C_4$ is from about 0.43 µg/mL to about 0.68 µg/mL; $C_6$ is from about 0.25 µg/mL to about 0.39 µg/mL; $C_8$ is from about 0.13 µg/mL to about 0.21 µg/mL; and $C_{12}$ is from about 0.04 µg/mL to about 0.06 µg/mL.

In certain embodiments, oral administration of a SR4 tablet or tablets for a total dose of 360 mg levodopa prodrug (208 mg-equivalents levodopa) to (12) fasted healthy adult human subjects provides a mean levodopa blood pharmacokinetic profile where $C_1$ is about 0.62 µg/mL, $C_2$ is about 0.69 µg/mL, $C_4$ is about 0.50 µg/mL, $C_6$ is about 0.24 µg/mL, $C_8$ is about 0.14 µg/mL, and $C_{12}$ is about 0.04 µg/mL.

In certain embodiments, oral administration of a SR4 tablet or tablets for a total dose of 360 mg levodopa prodrug (208 mg-equivalents levodopa) to (12) fasted healthy adult human subjects provides a mean levodopa blood pharmacokinetic profile where $C_1$ is from about 0.50 µg/mL to about 0.78 µg/mL; $C_2$ is from about 0.55 µg/mL to about 0.86 µg/mL; $C_4$ is from about 0.40 µg/mL to about 0.63 µg/mL; $C_6$ is from about 0.19 µg/mL to about 0.30 µg/mL; $C_8$ is from about 0.11 µg/mL to about 0.17 µg/mL; and $C_{12}$ is from about 0.03 µg/mL to about 005 µg/mL.

Dosage forms provided by the present disclosure may be characterized, in part, by their in vitro dissolution profile. Methods for determining dissolution profiles of dosage forms are well known to those skilled in the pharmaceutical arts. Standard methodologies set forth in the U.S. Pharmacopeia may be used. For example, a dissolution profile may be measured in either U.S. Pharmacopeia Type I Apparatus (baskets) or a U.S. Pharmacopeia Type II Apparatus (paddles).

Using the latter method, dissolution, or release, profiles of dosage forms provided by the present disclosure may be determined by immersing dosage forms in 0.1 N HCl, pH 1.2, pH 5, or other pH and a temperature of 37° C. and the dissolution medium agitated at 50 rpm (USP, Type II). Samples can be withdrawn from the dissolution medium at intervals and the content of (2R)-2-phenylcarbonyloxypropyl (2S)-2-amino-3-(3,4-dihydroxyphenyl)propanoate, mesylate and other compounds in the dissolution medium determined using reversed phase HPLC.

In certain embodiments, release of crystalline (2R)-2-phenylcarbonyloxypropyl (2S)-2-amino-3-(3,4-dihydroxyphenyl)propanoate, mesylate from tablets comprising crystalline (2R)-2-phenylcarbonyloxypropyl (2S)-2-amino-3-(3,4-dihydroxyphenyl)propanoate, mesylate and a $C_{6-18}$ alkylsulfate or pharmaceutically acceptable salt thereof, such as sodium lauryl sulfate exhibits an in vitro dissolution profile in 0.1 N HCl, pH 1.2 and 37° C. agitated at 50 rpm (USP, Type II) in which from about 37% to about 47% of crystalline (2R)-2-phenylcarbonyloxypropyl (2S)-2-amino-3-(3,4-dihydroxyphenyl)propanoate, mesylate is released within about 2.5 hours; from about 54% to about 64% of crystalline (2R)-2-phenylcarbonyloxypropyl (2S)-2-amino-3-(3,4-dihydroxyphenyl)propanoate, mesylate is released within about 5 hours; from about 79% to about 89% of crystalline (2R)-2-phenylcarbonyloxypropyl (2S)-2-amino-3-(3,4-dihydroxyphenyl)propanoate, mesylate is released within about 10 hours; and from about 90% to about 100% of crystalline (2R)-2-phenylcarbonyloxypropyl (2S)-2-amino-3-(3,4-dihydroxyphenyl)propanoate, mesylate is released within about 15 hours. In certain embodiments, release of crystalline (2R)-2-phenylcarbonyloxypropyl (2S)-2-amino-3-(3,4-dihydroxyphenyl)propanoate, mesylate from tablets comprising crystalline (2R)-2-phenylcarbonyloxypropyl (2S)-2-amino-3-(3,4-dihydroxyphenyl)propanoate, mesylate and a $C_{6-18}$ alkylsulfate or pharmaceutically acceptable salt thereof, such as sodium lauryl sulfate exhibits an in vitro dissolution profile in 0.1 NHCl, pH 1.2 and 37° C. agitated at 50 rpm (USP, Type II) in which from about 42% of crystalline (2R)-2-phenylcarbonyloxypropyl (2S)-2-amino-3-(3,4-dihydroxyphenyl)propanoate, mesylate is released within about 2.5 hours; from about 59% of crystalline (2R)-2-phenylcarbonyloxypropyl (2S)-2-amino-3-(3,4-dihydroxyphenyl)propanoate, mesylate is released within about 5 hours; about 84% of levodopa prodrug is released within about 10 hours; and about 95% of levodopa prodrug is released within about 15 hours. In certain embodiments, release of crystalline (2R)-2-phenylcarbonyloxypropyl (2S)-2-amino-3-(3,4-dihydroxyphenyl)propanoate, mesylate from tablets comprising crystalline (2R)-2-phenylcarbonyloxypropyl (2S)-2-amino-3-(3,4-dihydroxyphenyl)propanoate, mesylate and a $C_{6-18}$ alkylsulfate or pharmaceutically acceptable salt thereof, such as sodium lauryl sulfate exhibits an in vitro dissolution profile in 0.1 N HCl, pH 1.2 at 37° C. and agitated at 50 rpm, releases about 28% to about 58% of the crystalline (2R)-2-phenylcarbonyloxypropyl (2S)-2-amino-3-(3,4-dihydroxyphenyl)propanoate mesylate within about 2 hours, about 40% to about 70% within about 4 hours, about 67% to about 97% within about 9 hours, and greater than about 80% within about 18 hours.

In certain embodiments, the dissolution profile is substantially as shown in FIG. 1.

In certain embodiments, an oral dosage from is a bilayer tablet dosage form comprising a first layer comprising crystalline (2R)-2-phenylcarbonyloxypropyl (2S)-2-amino-3-(3, 4-dihydroxyphenyl)propanoate mesylate and a $C_{6-18}$ alkylsulfate or pharmaceutically acceptable salt thereof; and a second layer comprising carbidopa. In certain embodiments of a bilayer tablet, the first layer comprise from about 70 wt-% to about 90% crystalline (2R)-2-phenylcarbonyloxypropyl (2S)-2-amino-3-(3,4-dihydroxyphenyl)propanoate mesylate, in certain embodiments about 85 wt-% to about 90 wt-% crystalline (2R)-2-phenylcarbonyloxypropyl (2S)-2-amino-3-(3,4-dihydroxyphenyl)propanoate mesylate, and in certain embodiments about 88 wt-% crystalline (2R)-2-phenylcarbonyloxypropyl (2S)-2-amino-3-(3,4-dihydroxyphenyl)propanoate mesylate. In certain embodiments of a bilayer tablet, the first layer comprises about 0.5 wt-% to about 3 wt-% a $C_{6-18}$ alkylsulfate or pharmaceutically acceptable salt thereof such as sodium lauryl sulfate, in certain embodiments about 0.7 wt-% to about 1.1 wt-% a $C_{6-18}$ alkylsulfate or pharmaceutically acceptable salt thereof such as sodium lauryl sulfate, and in certain embodiments about 0.9 wt-% a $C_{6-18}$ alkylsulfate or pharmaceutically acceptable salt thereof such as sodium lauryl sulfate. In certain embodiments of a bilayer tablet, the first layer comprises about 70 wt-% to about 90% crystalline (2R)-2-phenylcarbonyloxypropyl (2S)-2-amino-3-(3,4-dihydroxyphenyl)propanoate mesylate and about 0.5 wt-% to about 3 wt-% a $C_{6-18}$ alkylsulfate or pharmaceutically acceptable salt thereof such as sodium lauryl sulfate, and in certain embodiments, about 85 wt-% to about 90 wt-% crystalline (2R)-2-phenylcarbonyloxypropyl (2S)-2-amino-3-(3,4-dihydroxyphenyl)propanoate mesylate and about 0.7 wt-% to about 1.1 wt-% a $C_{6-18}$ alkylsulfate or pharmaceutically acceptable salt thereof such as sodium lauryl sulfate. In certain embodiments of a bilayer tablet dosage form, the second layer comprises about 15 wt-% to about 30 wt-% carbidopa, in certain embodiments about 15 wt-% to about 25 wt-% carbidopa, and in certain embodiments, about 20 wt-% carbidopa. In certain embodiments of a bilayer tablet, the first layer comprises about 70 wt-% to about 90% crystalline (2R)-2-phenylcarbonyloxypropyl (2S)-2-amino-3-(3,4-dihydroxyphenyl)propanoate mesylate and about 0.5 wt-% to about 3 wt-% a $C_{6-18}$ alkylsulfate or pharmaceutically acceptable salt thereof such as sodium lauryl sulfate, and the second layer comprises about 15 wt-% to about 30 wt-% carbidopa; and in certain embodiments, about 85 wt-% to about 90 wt-% crystalline (2R)-2-phenylcarbonyloxypropyl (2S)-2-amino-3-(3,4-dihydroxyphenyl)propanoate mesylate and about 0.7 wt-% to about 1.1 wt-% a $C_{6-18}$ alkylsulfate or pharmaceutically acceptable salt thereof such as sodium lauryl sulfate, and the second layer comprises about 15 wt-% to about 25 wt-% carbidopa. In certain of the foregoing embodiments, the first layer comprises granules wherein the granules comprise about 90 wt-% to about 99 wt-% crystalline (2R)-2-phenylcarbonyloxypropyl (2S)-2-amino-3-(3,4-dihydroxyphenyl)propanoate mesylate; and about 0.5 wt-% to about 2 wt-% $C_{6-18}$ alkylsulfate or pharmaceutically acceptable salt thereof; wherein wt-% is based on the total dry weight of the granules. In certain embodiments of a bilayer tablet, the second layer comprises an immediate release formulation of carbidopa.

In certain embodiments of a bilayer tablet dosage from, release of crystalline (2R)-2-phenylcarbonyloxypropyl (2S)-2-amino-3-(3,4-dihydroxyphenyl)propanoate, mesylate from bilayer tablets exhibits an in vitro dissolution profile in 0.1 N HCl, pH 1.2 or pH 5.0 and 37° C. agitated at 50 rpm (USP, Type II) in which from about 34% to about 50% of the crystalline (2R)-2-phenylcarbonyloxypropyl (2S)-2-amino-3-(3,4-dihydroxyphenyl)propanoate mesylate is released within about 2 hours, about 55% to about 75% within about 4 hours, about 71% to about 91% within about 6 hours, and about 86% to about 100% within about 9 hours. In certain embodiments of a bilayer tablet dosage from, release of crystalline (2R)-2-phenylcarbonyloxypropyl (2S)-2-amino-3-(3,4-dihydroxyphenyl)propanoate, mesylate from bilayer tablets exhibits an in vitro dissolution profile in 0.1 N HCl, pH 1.2 or pH 5.0 and 37° C. agitated at 50 rpm (USP, Type II) in which from about 38% to about 46% of the crystalline (2R)-2-phenylcarbonyloxypropyl (2S)-2-amino-3-(3,4-dihydroxyphenyl)propanoate mesylate is released within about 2 hours, about 60% to about 70% within about 4 hours, about 76% to about 86% within about 6 hours, and about 91% to about 100% within about 9 hours. In certain embodiments of a bilayer tablet dosage from, release of crystalline (2R)-2-phenylcarbonyloxypropyl (2S)-2-amino-3-(3,4-dihydroxyphenyl)propanoate, mesylate from bilayer tablets exhibits an in vitro dissolution profile in 0.1 N HCl, pH 1.2 or pH 5.0 and 37° C. agitated at 50 rpm (USP, Type II) in which from about 42% of the crystalline (2R)-2-phenylcarbonyloxypropyl (2S)-2-amino-3-(3,4-dihydroxyphenyl)propanoate mesylate is released within about 2 hours, about 65% within about 4 hours, about 81% within about 6 hours, and about 96% within about 9 hours. 19. In certain embodiments, of a bilayer tablet dosage from, release of crystalline (2R)-2-phenylcarbonyloxypropyl (2S)-2-amino-3-(3,4-dihydroxyphenyl)propanoate, mesylate from bilayer tablets exhibits an in vitro dissolution profile in 0.1 N HCl, pH 1.2 or pH 5.0 at 37° C. and agitated at 50 rpm, releases about 28% to about 58% of the crystalline (2R)-2-phenylcarbonyloxypropyl (2S)-2-amino-3-(3,4-dihydroxyphenyl)propanoate mesylate within about 2 hours, about 50% to about 80% within about 4 hours, and greater than about 80% within about 12 hours.

Figure 6:
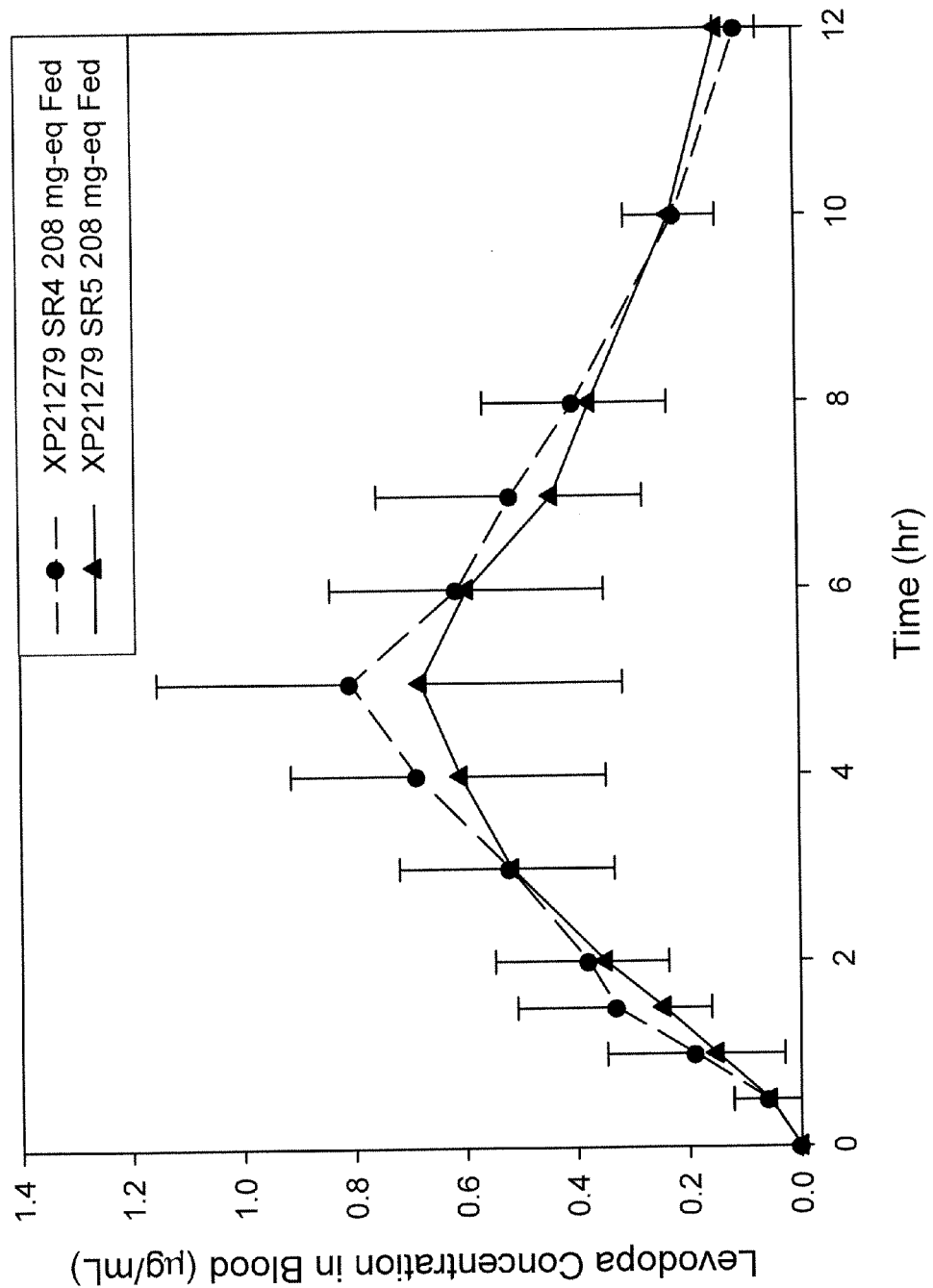
FIG. 6 shows levodopa prodrug dissolution profiles for bilayer tablets prepared according to Example 9 and having the composition described in Table 5.

In certain embodiments, the dissolution profile of a bilayer tablet is substantially as shown in FIG. 6.

In certain embodiments, bilayer tablet dosage forms exhibit a release profile that is similar to any of the profiles described in Example 8, Example 10, FIG. 4, FIG. 7, FIG. 8, or FIG. 9.

In certain embodiments, a tablet dosage form provided by the present disclosure exhibits a dissolution profile that is equivalent to any one of the dissolution profiles disclosed herein. Consistent with "Dissolution Testing of Immediate Release Solid Oral Dosage Forms—Guidance for Industry", FDA-CDER, August 1997, dissolution profiles may be considered similar based on a difference factor ($f_1$) and a similarity factor ($f_2$). For dissolution profiles to be considered similar, $f_1$ values should be close to 0 and $f_2$ values should be close to 100. Generally, $f_1$ values up to 15 (0-15) and $f_2$ values greater than 50 (50-100) ensure sameness or equivalence of two dissolution profiles. Procedures for calculating $f_1$ and $f_2$ are set forth in the foregoing reference. In certain embodiments, oral tablet dosage forms provided by the present disclosure exhibit a dissolution profile that when compared with any one of the foregoing dissolution profiles or any of the dissolution profiles presented in FIG. 1, FIG. 4, FIG. 7, FIG. 8, or FIG. 9 produce an $f_1$ difference factor less than 15 and an $f_2$ similarity factor from 50 to 100.

Crystalline (2R)-2-phenylcarbonyloxypropyl (2S)-2-amino-3-(3,4-dihydroxyphenyl)propanoate, mesylate is a precursor to levodopa, which is a precursor of dopamine. Thus, crystalline (2R)-2-phenylcarbonyloxypropyl (2S)-2-amino-3-(3,4-dihydroxyphenyl)propanoate, mesylate and oral dosage forms comprising crystalline (2R)-2-phenylcarbonyloxypropyl (2S)-2-amino-3-(3,4-dihydroxyphenyl)propanoate, mesylate and a $C_{6-18}$ alkylsulfate or pharmaceutically acceptable salt thereof, such as sodium lauryl sulfate provided by the present disclosure may be administered to a patient suffering from any disease or disorder for which the parent drug, levodopa or dopamine, is known, believed to be, or hereafter discovered to be therapeutically effective. Indications for which levodopa has been prescribed, and hence for which the dosage forms of the present disclosure are also effective, include Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, or excessive daytime sleepiness.

In therapeutic methods provided by the present disclosure, a therapeutically effective amount of crystalline (2R)-2-phenylcarbonyloxypropyl (2S)-2-amino-3-(3,4-dihydroxyphenyl)propanoate, mesylate may be administered to a patient suffering from a disease such as Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, or excessive daytime sleepiness.

Parkinson's disease (PD) is a progressive neurodegenerative disorder that affects about 1% of the population over 55 years of age. The pathological manifestation of PD is the loss of dopaminergic neurons in the Substantia Nigra pars compacta and the presence of intracycloplasmic inclusions, called Lewy bodies, formed mainly by α-synuclein and ubiquitin. The main symptoms of PD are tremor, bradykinesia, hypokinesia, and balance and coordination disturbances. Dopamine replacement therapy can alleviate the symptoms of PD, however as the disease progresses, drug-related side effects emerge as well as disabling symptoms that are not responsive to the treatment. Although the cause of PD is unknown, dopaminergic cell loss has been associated with several mechanisms of cell damage including excitotoxicity, disturbed calcium homeostasis, inflammation, apoptosis, distress energy metabolism, and protein aggregation. Because patients with PD have a normal lifespan, they must endure crippling symptoms for many years, severely impacting their quality of life. Therefore, a neuroprotective therapy that can stop or reduce the continual loss of dopaminergic neurons is needed.

Parkinson's disease is a clinical syndrome comprising bradykinesia (slowness and poverty of movement), muscular rigidity, resting tremor (which usually abates during voluntary movement), and an impairment of postural balance leading to disturbance of gait and falling. Other symptoms include gait and posture disturbances such as shuffling, decreased arm swing, turning "en bloc," stooped, forward-reflexed posture, festination, gait freezing and dystonia; speech and swallowing disturbances such as hypophonia, festinating speech, drooling, non-motor causes of speech/language disturbance in both expressive and receptive language, and dysphagia; as well as fatigue, masked facies, micorpgraphia, impaired fine motor dexterity and coordination, impaired gross motor coordination, and poverty of movement. Non-motor mood disturbances associated with Parkinson's disease include mood disturbances such as depression; cognitive disturbances such as slowed reaction time, executive dysfunction, dementia, memory loss, and medication effects; sleep disturbances such as excessive daytime somnolence, insomnia, and disturbances in REM sleep; sensation disturbances such as impair visual perception, dizziness and fainting, impaired proprioception, reduction or loss of sense of smell, and pain; and autonomic disturbances such as oily skin and seborrheic dermatitis, urinary incontinence, constipation and gastric dysmotility, altered sexual function, and weight loss.

The Unified Parkinson's disease Rating scale is the primary clinical tool used for the diagnosis of Parkinson's disease.

Levodopa has been shown effective in treating Parkinson's disease (Olanow et al., *Nat Clin Pract Neurol* 2006, 2, 382-92).

The efficacy of a compound of crystalline (2R)-2-phenylcarbonyloxypropyl (2S)-2-amino-3-(3,4-dihydroxyphenyl)propanoate, mesylate in treating Parkinson's disease may be assessed using animal models of Parkinson's disease and in clinical studies.

Schizophrenia includes a group of neuropsychiatric disorders characterized by dysfunctions of the thinking process, such as delusions, hallucinations, and extensive withdrawal of the patient's interests from other people. Schizophrenia includes the subtypes of paranoid schizophrenia characterized by a preoccupation with delusions or auditory hallucinations, hebephrenic or disorganized schizophrenia characterized by disorganized speech, disorganized behavior, and flat or inappropriate emotions; catatonic schizophrenia dominated by physical symptoms such as immobility, excessive motor activity, or the assumption of bizarre postures; undifferentiated schizophrenia characterized by a combination of symptoms characteristic of the other subtypes; and residual schizophrenia in which a person is not currently suffering from positive symptoms but manifests negative and/or cognitive symptoms of schizophrenia (DSM-IV-TR classifications 295.30 (Paranoid Type), 295.10 (Disorganized Type), 295.20 (Catatonic Type), 295.90 (Undifferentiated Type), and 295.60 (Residual Type); Diagnostic and Statistical Manual of Mental Disorders, 4$^{th}$ Edition, American Psychiatric Association, 297-319, 2005). Schizophrenia includes these and other closely associated psychotic disorders such as schizophreniform disorder, schizoaffective disorder, delusional disorder, brief psychotic disorder, shared psychotic disorder, psychotic disorder due to a general medical condition, substance-induced psychotic disorder, and unspecified psychotic disorders. Schizoaffective disorder characterized by symptoms of schizophrenia as well as mood disorder such as major depression, bipolar mania, or mixed mania, is included as a subtype of schizophrenia.

Schizophrenia symptoms can be classified as positive, negative, or cognitive. Positive symptoms of schizophrenia include delusion and hallucination, which can be measured using, for example, the Positive and Negative Syndrome Scale (PANSS). Negative symptoms of schizophrenia include affect blunting, anergia, alogia, and social withdrawal, which can be measured for example, using the Scales for the Assessment of Negative Symptoms (SANS). Cognitive symptoms of schizophrenia include impairment in obtaining, organizing, and using intellectual knowledge, which can be measured using the Positive and Negative Syndrome Scale-cognitive subscale (PANSS-cognitive subscale) or by assessing the ability to perform cognitive tasks.

Treating schizophrenia encompasses treating one or more symptoms, positive, negative, cognitive, and other associated features, of schizophrenia. Examples of symptoms of schizophrenia include delusions, hallucinations, disorganized speech, affective flattening, alogia, anhedonia, inappropriate affect, dysphoric mood (in the form of, for example, depression, anxiety, and/or anger), and some indications of cognitive dysfunction.

Administration of high doses of a dopamine D2 receptor agonist or precursor thereof such as levodopa, either alone or concomitant with an antipsychotic drug, has been shown to exacerbate psychosis, or even induce psychosis in non-psychotic patients. However, relatively low doses of levodopa given as adjunctive treatment with typical antipsychotic drugs improves the clinical outcome in schizophrenia (see Jaskiw and Popli, *Psychopharmacology* 2004, 171, 365-374), suggesting an enhanced effect on negative symptoms and cognitive impairment without worsening of psychotic symptoms (Alpert and Friedhoff, *Am J Psychiatry* 1980, 135, 1329-32; Bruno and Bruno, *Acta Psychiatr Scand,* 1966, 42, 264-71; Buchanan et al., *Aust N Z J Psychiatry* 1975, 9, 269-71; Gerlach and Luhdorf, *Psychopharmacologia* 1975, 44, 105-110; Inanaga et al., *Folia Psychiatr Neurol Jpn* 1975, 29, 123-43; and Kay and Opler, *Int J Psychiat Med* 1985-86, 15, 293-98). The results of these studies suggest that adjunctive low-dose levodopa together with a low dose of a conventional antipsychotic drug can be expected to generate a therapeutic profile similar to that of atypical antipsychotic drugs, including enhanced treatment efficacy against negative symptoms and cognitive impairment in schizophrenia, with retained therapeutic effects on positive symptoms and without concomitant increased extrapyramidal symptom liability. Because the severity of cognitive impairment has a crucial impact on treatment outcome the use of adjunctive, low-dose levodopa with selective dopamine D2 antagonists might also prove efficacious in treating both the positive and negative or cognitive symptoms of schizophrenia (Trân, U.S. Patent Application Publication No. 2008/0070984).

Oral dosage forms comprising a levodopa prodrug may be used to treat a positive symptom of schizophrenia, a negative or cognitive symptom of schizophrenia, both a positive and a negative or cognitive symptom of schizophrenia and/or closely associated psychotic disorders such as schizophreniform disorder, schizoaffective disorder, delusional disorder, brief psychotic disorder, shared psychotic disorder, psychotic disorder due to a general medical condition, substance-induced psychotic disorder, and/or unspecified psychotic disorders in a patient. Positive symptoms of schizophrenia include delusion and hallucination. Negative symptoms of schizophrenia include affect blunting, anergia, alogia, and social withdrawal. Cognitive symptoms of schizophrenia include impairment in obtaining, organizing, and using intellectual knowledge. In certain embodiments, a levodopa prodrug may be used to treat both a positive and a negative or cognitive symptom of schizophrenia by orally administering a levodopa prodrug to a patient in need of such treatment.

The efficacy of a levodopa prodrug and oral dosage forms thereof in treating schizophrenia may be determined by methods known to those skilled in the art. For example, negative, positive, and/or cognitive symptom(s) of schizophrenia may be measured before and after treatment of the patient. Reduction in such symptom(s) indicates that a patient's condition has improved. Improvement in the symptoms of schizophrenia may be assessed using, for example, the Scale for Assessment of Negative Symptoms (SANS), Positive and Negative Symptoms Scale (PANSS), and/or using Cognitive Deficits tests such as the Wisconsin Card Sorting Test (WCST) and other measures of cognitive function.

The efficacy of a levodopa prodrug may also be evaluated using animal models of schizophrenia.

Restless legs syndrome (RLS) is an intensely uncomfortable sensory-motor disorder that afflicts between 5 and 10% of the general population. Characteristic symptoms of RLS include lower extremity dysesthesias or paresthesias, motor restlessness, nocturnal increase of paresthesias and motor restlessness, and symptoms that increase at rest, i.e., sitting or lying. Typically, symptoms increase at night (Garcia-Borreguero et al., *Neurol.* 2002, 11(2), 1573-79). RLS may start at any age, even during childhood, although is usually observed in adults. The clinical course generally changes over time, but tends to become more pronounced with age, with up to 28% of those over 65 being affected.

In addition to sensory symptoms such as paresthesia, which is a sensation of numbness, tingling, burning or pain, accompanied by an urge to move the limbs, patients also experience motor symptoms. When awake and sitting or lying down, the patient has rhythmic or semi-rhythmic movements of the legs (i.e., dysesthesias). While sleeping, patients frequently demonstrate similar semi-rhythmic legs movements, which have been referred to as periodic leg movements during sleep (PLMS). These jerky leg movements are repetitive, highly stereotypical and are characterized by extension of the big toe along with flexion of the ankle, knee and sometimes the hip. About 85-90% of RLS sufferers also exhibit PLMS and these patients complain of daytime fatigue and sleepiness or insomnia, which have a profound negative effect on quality of life, including daytime fatigue, poor work performance and interrupted social and/or family life. Diagnostic criteria for RLS includes a distressing urge to move the limbs because of paraesthesias or spontaneous jerks in the legs or less often in other body parts, a worsening of these symptoms at rest, a temporary relief by motor activity, and worsening of the symptoms in the evening or during the night.

Levodopa has been shown to be effective in treating RLS (Ondo and Jankovic, *Neurology* 1996, 47, 1435-41).

The efficacy of a compound of a levodopa prodrug in treating RLS may be assessed using animal and human models of RLS and in clinical studies.

Huntington's disease is an autosomal dominant neurodegenerative disorder in which specific cell death occurs in the neostriatum and cortex. Onset usually occurs during the fourth or fifth decade of life, with a mean survival at age onset of 14 to 20 years. Huntington's disease is universally fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein, huntingtin. A number of studies suggest that there is a progressive impairment of energy metabolism, possibly resulting from mitochondrial damage caused by oxidative stress as a consequence of free radical generation.

Levodopa has shown effectiveness in treating rigidity associated with Huntington's disease (Bonelli and Wenning, *Current Pharmaceutical Design* 2006, 12(21), 2701-2720).

The efficacy of crystalline (2R)-2-phenylcarbonyloxypropyl (2S)-2-amino-3-(3,4-dihydroxyphenyl)propanoate, mesylate for treating Huntington's disease may be assessed using animal and human models of Huntington's disease and clinical studies.

Dystonia is involuntary, slow, repetitive, sustained muscle contractions that may cause freezing in the middle of an action, as well as twisting or turning of the trunk, the entire body, or part of the body.

Dystonia is a neurological syndrome characterized by involuntary, patterned, sustained, or repetitive muscle contractions of opposing muscles, causing twisting movements and abnormal postures. Causes of dystonia include a severe lack of oxygen to the brain that occurs at birth or later in life, Parkinson's disease, multiple sclerosis, toxicity due to accumulation of certain metals such as copper in Wilson's disease, stroke, and as side effects to antipsychotic drugs. Chronic dystonia is usually genetic. Types and symptoms of dystonia include focal dystonias confined to particular muscles or muscle groups such as blepharospasm, oromandibular dystonia, spasmodic dysphonia, cervical dystonia, and task-specific dystonias, segmental dystonias in which certain parts of the body are affected, and generalized dystonias in which muscles throughout the body are affected. Dopa-responsive dystonia, characterized by childhood onset, parkinsonian features, gait and postural abnormalities, diurnal fluctuation, and autosomal dominant inheritance is a genetic disorder representing up to about 5% of childhood dystonias.

Levodopa substantially improves or can completely resolve this type of dystonia (Jankovic, *Lancet Neurol* 2006, 5, 864-72; and Schneider et al., *Neurology* 2006, 66(4), 599-601).

The efficacy of a compound of a levodopa prodrug in treating dystonia may be assessed using animal and human models of dystonia and in clinical studies.

Tardive dyskinesia is a neurological disorder caused by the long-term or high-dose use of dopamine antagonists such as antipsychotics. Tardive dyskinesia is characterized by repetitive, involuntary, purposeless movements such as grimacing, tongue protrusion, lip smacking, puckering and pursing of the lips, and rapid eye blinking, and can also involve rapid movements of the arms, legs, and trunk.

Studies suggest that levodopa can be useful in treating movement disorders induced by neuroleptic drugs such as tardive dyskinesia (Rascol and Fabre, *Clinical Neuropharmacology* 2001, 24(6), 313-323; Soares and McGrath, *Schizophr Res* 1999, 39(1), 1-16; and Ebadi and Srnivasan, *Pharmacological Reviews* 1996, 47(4), 575-604).

Efficacy of tardive dyskinesia treatment can be assessed using animal models and in clinical trials.

Levodopa combined with physiotherapy has been shown to improve motor recovery after stroke (Scheidtmann et al., *The Lancet*, 2001, 358, 787-790; and Floel et al., *Neurology* 2005, 65(3), 472-4).

The efficacy of a compound of a levodopa prodrug in treating stroke may be assessed using animal and human models of stroke and in clinical studies.

Levodopa has been shown to be effective in treating cognitive dysfunction in patients with Parkinson's disease (Cools, *Neuroscience Biobehavioral Rev* 2006, 30, 1-23; and Kulisevsky, *Drugs Aging* 2000, 16(5), 365-79), enhance training effects in motor memory formation in the elderly (Floel et al., *Neurobiology of Aging* 2006, PMID 17098831), and improve word learning in healthy patients (Knecht et al., *Ann. Neurol* 2004, 56(1), 20-6).

The efficacy of a compound of a levodopa prodrug in treating learning and memory disorders may be assessed using animal and human models of learning and memory disorders and in clinical studies.

Excessive daytime sleepiness (EDS), also known as hypersomnia is characterized by recurrent episodes of excessive daytime sleepiness or prolonged nighttime sleep. Hypersomnia can be caused by genetics, brain damage, and disorders such as clinical depression and fibromyalgia and can also be a symptom of other sleep disorders such as narcolepsy, sleep apnea, and restless legs syndrome. Hypersomnia can be diagnosed using the Epworth sleepiness test. Levodopa has shown efficacy in treating hypersomnia (Silber, *Neurologic Clinics* 2001, 19(1), 173-86).

The efficacy of a compound of a levodopa prodrug in treating excessive daytime sleepiness may be assessed using animal and human models of excessive daytime sleepiness and in clinical studies.

Depressive disorders include major depressive disorder, dysthymic disorder, premenstrual dysphoric disorder, minor depressive disorder, recurrent brief depressive disorder, and postpsychotic depressive disorder of schizophrenia (see DSM IV).

The efficacy of compounds provided by the present disclosure for treating depression can be evaluated in animal models of depression such as the forced swim test.

The amount of crystalline (2R)-2-phenylcarbonyloxypropyl (2S)-2-amino-3-(3,4-dihydroxyphenyl)propanoate, mesylate that will be effective in the treatment of a particular disease disclosed herein will depend, at least in part, on the nature of the disease, and may be determined by standard clinical techniques known in the art as previously described. In addition, in vitro or in vivo assays can optionally be employed to help identify optimal dosage ranges. Dosage regimens and dosing intervals may also be determined by methods known to those skilled in the art. The amount of crystalline (2R)-2-phenylcarbonyloxypropyl (2S)-2-amino-3-(3,4-dihydroxyphenyl)propanoate, mesylate administered may depend on, among other factors, the subject being treated, the weight of the subject, the severity of the disease or disorder, the manner of administration, and the judgment of the prescribing physician. Suitable doses of orally administered levodopa are generally from about 0.1 mg/day to about 2 grams/day.

A dose of crystalline (2R)-2-phenylcarbonyloxypropyl (2S)-2-amino-3-(3,4-dihydroxyphenyl)propanoate, mesylate can be adjusted to provide an equivalent molar quantity or mass equivalent dose of levodopa (expressed as mg-equivalent levodopa). Therapeutically effective doses of levodopa are generally from about 0.15 mg to about 2.5 mg per kilogram body weight per day. In certain embodiments, a dose can comprise a mass equivalent of levodopa ranging from about 0.1 mg to about 2 grams, in certain embodiments, from about 10 mg to about 1 gram, in certain embodiments, from about 50 mg to about 500 mg, in certain embodiments, from about 100 mg to about 250 mg, and in certain embodiments, from about 2 mg to about 40 mg. The dose of crystalline (2R)-2-phenylcarbonyloxypropyl (2S)-2-amino-3-(3,4-dihydroxyphenyl)propanoate, mesylate and appropriate dosing intervals can be selected to maintain a sustained therapeutically effective concentration of levodopa in the blood of a patient, and in certain embodiments, without exceeding a minimum adverse concentration.

Oral dosage forms comprising crystalline (2R)-2-phenylcarbonyloxypropyl (2S)-2-amino-3-(3,4-dihydroxyphenyl)propanoate, mesylate and a $C_{6-18}$ alkylsulfate or pharmaceutically acceptable salt thereof, such as sodium lauryl sulfate, may be administered in similar amounts and using a similar schedule as described in the art for levodopa. For example, oral dosage forms provided by the present disclosure may be useful in treating Parkinson's disease by administration of crystalline (2R)-2-phenylcarbonyloxypropyl (2S)-2-amino-3-(3,4-dihydroxyphenyl)propanoate, mesylate together with a decarboxylase inhibitor such as carbidopa or a prodrug of carbidopa and/or COMT inhibitor such as entacapone or tolecapone, in certain embodiments by the oral route, to a mammalian subject in need of the treatment. In a human subject weighing about 70 kg, crystalline (2R)-2-phenylcarbonyloxypropyl (2S)-2-amino-3-(3,4-dihydroxyphenyl)propanoate, mesylate may be administered at a dose over time having an equivalent weight of levodopa of from about 10 mg to about 10 g per day, from about 10 mg to about 1 gram per day, from about 50 mg to about 500 mg per day, from about 100 mg to about 250 mg per day, and in certain embodiments, an equivalent weight of levodopa of from about 100 mg to about 3 g per day. A dose of crystalline (2R)-2-phenylcarbonyloxypropyl (2S)-2-amino-3-(3,4-dihydroxyphenyl)propanoate, mesylate taken at any one time can have an equivalent weight of levodopa of from about 10 mg to about 3 g, from about 50 mg to about 1 gram, from about 100 mg to about 500 mg, and in certain embodiments, from about 100 mg to about 250 mg. A dose may be adjusted by one skilled in the art based on several factors, including, for example, the body weight and/or condition of the subject treated, the dose of the decarboxylase inhibitor or prodrug of a decarboxylase inhibitor being administered, the severity of the disease being treated, the incidence of side effects, the manner of administration, and the judgment of the prescribing physician. Dosage ranges may be determined by methods known to one skilled in the art.

In certain embodiments, a therapeutically effective dose of crystalline (2R)-2-phenylcarbonyloxypropyl (2S)-2-amino-3-(3,4-dihydroxyphenyl)propanoate, mesylate may provide therapeutic benefit without causing substantial toxicity. Toxicity of crystalline (2R)-2-phenylcarbonyloxypropyl (2S)-2-amino-3-(3,4-dihydroxyphenyl)propanoate, mesylate may be determined using standard pharmaceutical procedures and may be ascertained by one skilled in the art. The dose ratio between toxic and therapeutic effect is the therapeutic index. A dose of crystalline (2R)-2-phenylcarbonyloxypropyl (2S)-2-amino-3-(3,4-dihydroxyphenyl)propanoate, mesylate may be within a range capable of establishing and maintaining a therapeutically effective circulating plasma and/or blood concentration of levodopa that exhibits little or no toxicity.

In certain embodiments, dosage forms provided by the present disclosure may be administered once per day, twice per day, and in certain embodiments at intervals greater than once per day. Dosing may be provided alone or in combination with other drugs and may continue as long as required for effective treatment of the disease. Dosing includes administering a dosage form to a mammal, such as a human, in a fed or fasted state.

In certain embodiments, crystalline (2R)-2-phenylcarbonyloxypropyl (2S)-2-amino-3-(3,4-dihydroxyphenyl)propanoate, mesylate may be used in combination therapy with at least one other therapeutic agent. Pharmaceutical compositions and oral dosage forms provided by the present disclosure may include, in addition to crystalline (2R)-2-phenylcarbonyloxypropyl (2S)-2-amino-3-(3,4-dihydroxyphenyl)propanoate, mesylate, one or more therapeutic agents effective for treating the same or different disease, disorder, or condition.

Methods provided by the present disclosure include administration of crystalline (2R)-2-phenylcarbonyloxypropyl (2S)-2-amino-3-(3,4-dihydroxyphenyl)propanoate, mesylate or pharmaceutical compositions and oral dosage forms provided by the present disclosure and one or more other therapeutic agents, provided that the combined administration does not inhibit the therapeutic efficacy of crystalline (2R)-2-phenylcarbonyloxypropyl (2S)-2-amino-3-(3,4-dihydroxyphenyl)propanoate, mesylate or levodopa and/or does not produce adverse combination effects.

Crystalline (2R)-2-phenylcarbonyloxypropyl (2S)-2-amino-3-(3,4-dihydroxyphenyl)propanoate, mesylate and another therapeutic agent or agents may act additively or synergistically. In certain embodiments, pharmaceutical compositions and oral dosage forms provided by the present disclosure can be administered concurrently with the administration of another therapeutic agent, which may be contained in the same pharmaceutical composition or dosage form as, or in a different composition or dosage form from that containing crystalline (2R)-2-phenylcarbonyloxypropyl (2S)-2-amino-3-(3,4-dihydroxyphenyl)propanoate, mesylate. In certain embodiments, crystalline (2R)-2-phenylcarbonyloxypropyl (2S)-2-amino-3-(3,4-dihydroxyphenyl)propanoate, mesylate may be administered prior or subsequent to administration of another therapeutic agent. In certain embodiments of combination therapy, the combination therapy can comprise alternating between administering a composition provided by the present disclosure and a composition comprising another therapeutic agent, e.g., to minimize adverse side effects associated with a particular drug. When crystalline (2R)-2-phenylcarbonyloxypropyl (2S)-2-amino-3-(3,4-dihydroxyphenyl)propanoate, mesylate is administered concurrently with another therapeutic agent that can potentially produce adverse side effects including, but not limited to, toxicity, the therapeutic agent may advantageously be administered at a dose that falls below the threshold at which the adverse side effect is elicited.

In certain embodiments, a pharmaceutical composition or oral dosage form provided by the present disclosure may further be administered together with one or more compounds that enhance, modulate, and/or control the release, bioavailability, therapeutic efficacy, therapeutic potency, and/or stability of a crystalline (2R)-2-phenylcarbonyloxypropyl (2S)-2-amino-3-(3,4-dihydroxyphenyl)propanoate, mesylate and/or levodopa. For example, to enhance therapeutic efficacy of crystalline (2R)-2-phenylcarbonyloxypropyl (2S)-2-amino-3-(3,4-dihydroxyphenyl)propanoate, mesylate, the levodopa prodrug may be co-administered with one or more active agents to increase the absorption or diffusion of crystalline (2R)-2-phenylcarbonyloxypropyl (2S)-2-amino-3-(3,4-dihydroxyphenyl)propanoate, mesylate and/or levodopa through the gastrointestinal tract, or to modify degradation of crystalline (2R)-2-phenylcarbonyloxypropyl (2S)-2-amino-3-(3,4-dihydroxyphenyl)propanoate, mesylate and/or levodopa in the systemic circulation. In certain embodiments, a levodopa prodrug may be co-administered with an active agent having pharmacological effects that enhance the therapeutic efficacy of levodopa after being released from crystalline (2R)-2-phenylcarbonyloxypropyl (2S)-2-amino-3-(3,4-dihydroxyphenyl)propanoate, mesylate. In certain embodiments, crystalline (2R)-2-phenylcarbonyloxypropyl (2S)-2-amino-3-(3,4-dihydroxyphenyl)propanoate, mesylate may be co-administered with an active agent having pharmacological effects that enhance the therapeutic efficacy of dopamine after being released from levodopa.

In certain embodiments, crystalline (2R)-2-phenylcarbonyloxypropyl (2S)-2-amino-3-(3,4-dihydroxyphenyl)propanoate, mesylate may be co-administered with another therapeutic agent or drug, such as a decarboxylase inhibitor, which may act as a protectant to inhibit or prevent premature decarboxylation of crystalline (2R)-2-phenylcarbonyloxypropyl (2S)-2-amino-3-(3,4-dihydroxyphenyl)propanoate, mesylate and/or the levodopa metabolite. Examples of decarboxylase inhibitors include carbidopa and benserazide.

Crystalline (2R)-2-phenylcarbonyloxypropyl (2S)-2-amino-3-(3,4-dihydroxyphenyl)propanoate, mesylate may be delivered from the same dosage form as an L-aromatic amino acid decarboxylase inhibitor or from a different dosage form. Crystalline (2R)-2-phenylcarbonyloxypropyl (2S)-2-amino-3-(3,4-dihydroxyphenyl)propanoate, mesylate may be administered at the same time as, prior to, or subsequent to, the administration of a decarboxylase inhibitor. Crystalline (2R)-2-phenylcarbonyloxypropyl (2S)-2-amino-3-(3,4-dihydroxyphenyl)propanoate, mesylate together with a decarboxylase inhibitor or decarboxylase inhibitor prodrug or derivative may be administered to a patient, such as a human, to treat a disease or disorder such as Parkinson's disease.

In certain embodiments, crystalline (2R)-2-phenylcarbonyloxypropyl (2S)-2-amino-3-(3,4-dihydroxyphenyl)propanoate, mesylate may be co-administered with a catechol-O-methyltransferase (COMT) inhibitor such as entacapone and/or tolecapone. In certain embodiments, levodopa prodrugs may be administered to a patient, such as a human, together with a decarboxylase inhibitor such as carbidopa, a carbidopa prodrug, benserazide, or a benserazide prodrug, and a pharmaceutically active agent such as a COMT inhibitor or prodrug thereof, to treat a disease or disorder such as Parkinson's disease.

In certain embodiments, crystalline (2R)-2-phenylcarbonyloxypropyl (2S)-2-amino-3-(3,4-dihydroxyphenyl)propanoate, mesylate may be co-administered together with an L-aromatic amino acid decarboxylase inhibitor and a catechol-O-methyltransferase inhibitor, which may be included in the same pharmaceutical composition or dosage form as the crystalline (2R)-2-phenylcarbonyloxypropyl (2S)-2-amino-3-(3,4-dihydroxyphenyl)propanoate, mesylate, or may be contained in a separate pharmaceutical composition or administered as a separate dosage form. For example, crystalline (2R)-2-phenylcarbonyloxypropyl (2S)-2-amino-3-(3,4-dihydroxyphenyl)propanoate, mesylate and an L-aromatic amino acid decarboxylase inhibitor such as carbidopa and/or a catechol-O-methyltransferase inhibitor may be contained in a single dosage form such as a bilayer tablet. A bilayer tablet may contain one layer comprising crystalline (2R)-2-phenylcarbonyloxypropyl (2S)-2-amino-3-(3,4-dihydroxyphenyl)propanoate, mesylate and a second layer comprising an L-aromatic amino acid decarboxylase inhibitor such as carbidopa and/or a catechol-O-methyltransferase inhibitor. In certain embodiments of a bilayer tablet, the bilayer tablet comprises about a 1 to 4 ratio of carbidopa to levodopa equivalents. In certain embodiments, a bilayer tablet comprises from about 200 mg to about 300 mg crystalline (2R)-2-phenylcarbonyloxypropyl (2S)-2-amino-3-(3,4-dihydroxyphenyl)propanoate, mesylate and from about 17 mg to about 37 mg carbidopa. In certain embodiments, a bilayer tablet comprises from about 225 mg to about 275 mg crystalline (2R)-2-phenylcarbonyloxypropyl (2S)-2-amino-3-(3, 4-dihydroxyphenyl)propanoate, mesylate and from about 22 mg to about 32 mg carbidopa.

In certain embodiments, a pharmaceutical composition or oral dosage form provided by the present disclosure may be administered to a patient together with another compound for treating Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, stroke, excessive daytime sleepiness, dystonia, memory and learning deficits or loss, and Lewy Body disease.

In certain embodiments, a pharmaceutical composition or oral dosage form provided by the present disclosure may be administered to a patient for treating Parkinson's disease in combination with a therapy or another therapeutic agent known or believed to be effective in treating Parkinson's disease. Examples of drugs useful for treating Parkinson's disease include amantadine, baclofen, biperiden, benztropine, orphenadrine, procyclidine, trihexyphenidyl, levodopa, carbidopa, andropinirole, apomorphine, benserazide, bromocriptine, budipine, cabergoline, eliprodil, eptastigmine, ergoline, galanthamine, lazabemide, lisuride, mazindol, memantine, mofegiline, pergolide, piribedil, pramipexole, propentofylline, rasagiline, remacemide, ropinirole, selegiline, spheramine, terguride, entacapone, and tolcapone.

In certain embodiments, a pharmaceutical composition or oral dosage form provided by the present disclosure may be administered to a patient for treating depression in combination with a therapy or another therapeutic agent known or believed to be effective in treating depression. Examples of drugs useful for treating mood disorders such as depression include tricyclic antidepressants such as amitriptyline, amoxapine, clomipramine, desipramine, doxepin, imipramine, maprotiline, nortriptyline, protriptyline, and trimipramine; selective serotonin reuptake inhibitors such as citalopram, escitalopram, fluoxetine, fluvoxamine, paroxetine, and sertraline; serotonin-noradrenaline reuptake inhibitors such as venlafaxine, duloxetine, sibutramine, and milnacipran; monoamine oxidase inhibitors such as phenelzine and tranylcypromine; and psychostimulants such as dextroamphetamine and methylphenidate. Other antidepressants include benmoxine, butriptyline, dosulepin, imipramine, kitanserin, lofepramine, medifoxamine, mianserin, mirtazapine, viloxazine, cotinine, nisoxetine, reboxetine, tianeptine, acetaphenazine, binedaline, brofaromine, cericlamine, clovoxamine, iproniazid, isocarboxazid, moclobemide, phenyhydrazine, selegiline, sibutramine, ademetionine, adrafinil, amesergide, amisulpride, amperozide, benactyzine, bupropion, caroxazone, gepirone, idazoxan, metralindole, minaprine, nefazodone, nomifensine, ritanserin, roxindole, S-adenosylmethionine, escitalopram, tofenacin, trazodone, tryptophan, zalospirone, and Saint John's wort. An oral dosage form provided by the present disclosure may also be used in conjunction with psychotherapy or electroconvulsive therapy to treat mood disorders such as depression.

In certain embodiments, a pharmaceutical composition or oral dosage form provided by the present disclosure may be administered to a patient for treating attention deficit disorder in combination with a therapy or another therapeutic agent known or believed to be effective in treating attention deficit disorder. Examples of drugs useful for treating attention deficit disorder include atomoxetine, bupropion, dexmethylphenidate, dextroamphetamine, metamphetamine, methylphenidate, and pemoline.

In certain embodiments, a pharmaceutical composition or oral dosage form provided by the present disclosure may be administered to a patient for treating schizophrenia in combination with a therapy or another therapeutic agent known or believed to be effective in treating schizophrenia. Examples of drugs for treating schizophrenia include aripiprazole, loxapine, mesoridazine, quetiapine, reserpine, thioridazine, trifluoperazine, and ziprasidone.

In certain embodiments, a pharmaceutical composition or oral dosage form provided by the present disclosure may be administered to a patient for treating manic depression in combination with a therapy or another therapeutic agent known or believed to be effective in treating manic depression. Examples of drugs useful for treating manic depression include carbamazepine, clonazepam, clonidine, valproic acid, verapamil, lamotrigine, gabapentin, topiramate, lithium, clozapine, olanzapine, risperidone, quetiapine, ziprasidone, clonazepam, lorazepam, zolipidem, St. John's wort, and omega-3 fatty acids.

In certain embodiments, a pharmaceutical composition or oral dosage form provided by the present disclosure may be administered to a patient for treating cognitive or memory disorders in combination with a therapy or another therapeutic agent known or believed to be effective in treating cognitive or memory disorders. Examples of drugs useful for treating cognitive or memory disorders include antipsychotic drugs such as chlorpromazine, fluphenazine, haloperidol, loxapine, mesoridazine, molindone, perphenazine, pimozide, thioridazine, thiothixene, trifluoperazine, aripiprazole, clozapine, olanzapine, quetiapine, risperidone, and ziprasidone; sedatives such as diazepam and lorazepam; benzodiazepines such as alprazolam, chlordiazepoxide, clonazepam, clorazepate, diazepam, lorazepam, and oxazepam; nonsteroidal anti-inflammatory drugs such as aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, clopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and valdecoxib; acetylcholinesterase inhibitors such as donepezil, galantamine, rivastigmine, physostigmine, and tacrine; and N-methyl-D-aspartate (NMDA) receptor blockers such as memantine.

In certain embodiments, a pharmaceutical composition or oral dosage form provided by the present disclosure may be administered to a patient for treating restless legs syndrome in combination with a therapy or another therapeutic agent known or believed to be effective in treating restless legs syndrome. Examples of drugs useful for treating restless legs syndrome include dopaminergics such as levodopa, pergolide mesylate, pramipexole, and riniprole hydrochloride, benzodiazepines such as clonazepam and diazepam, opioids such as codeine, propoxyphene, and oxycodone, and anticonvulsants such as gabapentin, pregabalin, and carbamazepine.

In certain embodiments, a pharmaceutical composition or oral dosage form provided by the present disclosure may be administered to a patient for treating movement disorders in combination with a therapy or another therapeutic agent known or believed to be effective in treating movement disorders. Examples of drugs useful for treating movement disorders such as tardive dyskinesia include reserpine, tetrabenazine, and vitamin E.

In certain embodiments, a pharmaceutical composition or oral dosage form provided by the present disclosure may be administered to a patient for treating Huntington's disease in combination with a therapy or another therapeutic agent known or believed to be effective in treating Huntington's disease. Examples of drugs useful for treating Huntington's disease include antipsychotics such as haloperidol, chlorpromazine, and olanzapine; antidepressants such as fluoxetine, sertraline hydrochloride, and nortriptyline; tranquilizers such as benzodiazepines, paroxetine, venlafaxin, and beta-blockers; mood-stabilizers such as lithium, valproate, and carbamazepine; and Botulinum toxin.

In certain embodiments, a pharmaceutical composition or oral dosage form provided by the present disclosure may be administered to a patient for treating Tourette's syndrome in combination with a therapy or another therapeutic agent known or believed to be effective in treating Tourette's syndrome. Examples of drugs useful for treating Tourette's syndrome include haloperidol, pergolide, and pimozide.

In certain embodiments, a pharmaceutical composition or oral dosage form provided by the present disclosure may be administered to a patient for treating hypertension in combination with a therapy or another therapeutic agent known or believed to be effective in treating hypertension. Examples of drugs useful for treating hypertension include acebutolol, amiloride, amlodipine, atenolol, benazepril, betaxolol, bisoprolol, candesartan captopril, careolol, carvedilol, chlorothiazide, chlorthalidone, clonidine, diltiazem, doxazocin, enalapril, eplerenone, eprosartan, felodipine, fosinopril, furosemide, guanabenz, guanethidine, guanfacine, hydralazine, hydrochlorothiazide, indapamide, irbesartan, Isradipine, labetalol, lisinopril, losartan, methyldopa, metolazone, metoprolol, minoxidil, moexipril, nadolol, nicardipine, nifedipine, nisoldipine, nitroglycerin, olmesartan, perindopril, pindolol, prazosin, propranolol, quinapril, ramipril, reserpine, spironolactone, telmisartan, terazosin, timolol, torsemide, trandolapril, valsartan, and verapamil.

In certain embodiments, a pharmaceutical composition or oral dosage form provided by the present disclosure may be administered to a patient for treating alcohol addiction and abuse in combination with a therapy or another therapeutic agent known or believed to be effective in treating alcohol addiction and abuse. Examples of drugs useful for treating alcohol addiction or abuse include disulfuram, naltrexone, clonidine, methadone, 1-α-acetylmethadol, buprenorphine, and bupropion.

In certain embodiments, a pharmaceutical composition or oral dosage form provided by the present disclosure may be administered to a patient for treating narcotic addiction and abuse in combination with a therapy or another therapeutic agent known or believed to be effective in treating narcotic addiction and abuse. Examples of drugs useful for treating narcotic addiction or abuse include buprenorphine, tramadol, methadone, and naltrexone.

In certain embodiments, a pharmaceutical composition or oral dosage form provided by the present disclosure may be administered to a patient for treating nicotine addiction and abuse in combination with a therapy or another therapeutic agent known or believed to be effective in treating nicotine addiction and abuse. Examples of drugs useful for treating nicotine addiction or abuse include bupropion, clonidine, and nicotine.

In certain embodiments, a pharmaceutical composition or oral dosage form provided by the present disclosure may be administered to a patient for treating congestive heart failure in combination with a therapy or another therapeutic agent known or believed to be effective in treating congestive heart failure. Examples of drugs useful for treating congestive heart failure include allopurinol, amiloride, amlodipine, benazepril, bisoprolol, carvedilol, digoxin, enalapril, eplerenone, fosinopril, furosemide, hydrochlorothiazide, hydralazine, isosorbide dinitrate, isosorbide mononitrate, lisinopril, metoprolol, moexipril, nesiritide, nicardipine, nifedipine, nitroglycerin, perindopril, prazosin, quinapril, ramipril, spironolactone, torsemide, trandolapril, triamcinolone, and valsartan.

In certain embodiments, a pharmaceutical composition or oral dosage form provided by the present disclosure may be administered to a patient for treating excessive daytime sleepiness in combination with a therapy or another therapeutic agent known or believed to be effective in treating excessive daytime sleepiness. Examples of drugs useful for treating excessive daytime sleepiness include dextroamphetamine, methylphenidate, modafinil, sodium oxylate, clonidine, bromocriptine, antidepressants, and monoamine oxidase inhibitors.

In certain embodiments, a pharmaceutical composition or oral dosage form provided by the present disclosure may be administered to a patient for treating dystonia in combination with a therapy or another therapeutic agent known or believed to be effective in treating dystonia. Examples of drugs useful for treating dystonia include Botulinum-toxin, clonazepam, lorazepam, trihexyphenidyl, baclofen, diazepam, tetrabenazine, cyclobenzaprine, carbamazepine, and benzatropine.

EXAMPLES

The following examples describe in detail pharmaceutical compositions and oral dosage forms comprising crystalline (2R)-2-phenylcarbonyloxypropyl (2S)-2-amino-3-(3,4-dihydroxyphenyl)propanoate, mesylate and a $C_{6-18}$ alkylsulfate or pharmaceutically acceptable salt thereof such as sodium lauryl sulfate. It will be apparent to those skilled in the art that many modifications, both to materials and methods, may be practiced without departing from the scope of the disclosure.

Example 1

Synthesis of (2R)-2-Phenylcarbonyloxypropyl (2S)-2-Amino-3-(3,4-dihydroxyphenyl)propanoate Mesylate, Anhydrous (1)

Step A: (2S)-3-(3,4-Dihydroxyphenyl)-2-[(tert-butoxycarbonyl)amino]propanoic acid, tetrabutylammonium salt (1a)

A solution of N-Boc-(L)-Dopa (175 g, 0.59 mol) in methanol (1 L) was cautiously mixed with a methanolic solution of tetrabutylammonium hydroxide (1.0 M, 0.55 L) at 0° C. for 30 min. The mixture was then concentrated under reduced pressure and dried by azeotroping twice with toluene. The residue was crystallized after cooling at 4° C. for 16 h. The resulting crystalline solid was washed with acetone (400 mL×3), collected on a Buchner funnel, and then dried under high vacuum to afford 245 g (83% yield) of the title compound 1a. $^1$H NMR (400 MHz, DMSO-d6): δ 0.94 (t, J=7.6 Hz, 12H), 1.30 (m, 17H), 1.60 (m, 8H), 3.18 (m, 8H), 4.58 (m, 1H), 5.68 (d, J=5.6 Hz, 1H), 6.30 (d, J=7.6 Hz, 1H), 6.46 (d, J=8.0 Hz, 1H), 6.51 (s, 1H), 8.85 (s, 1H): 8.94 (s, 1H).

Step B: (1R)-2-Bromo-1-methylethyl benzoate (1b)

A solution of (2R)-propylene glycol (20.0 g, 262.8 mmol), benzaldehyde (33.4 mL, 328.6 mmol, 1.25 eq) and p-toluenesulfonic acid (2.5 g, 0.05 eq) in benzene (200 mL) was refluxed for 8 h after which water was removed using a Dean-Stark apparatus. The cooled solution was diluted with diethyl ether (100 mL), washed with aqueous NaOH (15%, 100 mL), brined (100 mL) and dried over $Na_2SO_4$. After filtration, removal of solvent under reduced pressure gave 44 g of crude benzaldehyde (2R)-propylene glycolacetal as an oil.

To a solution of the above crude benzaldehyde (2R)-propylene glycolacetal (10.0 g, 60.9 mmol) in hexane (100 mL) was added N-bromosuccinamide (NBS) (11.9 g, 67 mmol, 1.1 eq). The resulting mixture was stirred overnight at room temperature. The suspension was filtered through Celite and the filtrate was diluted with hexane (300 mL), washed with saturated $NaHCO_3$ (100 mL) and brine (100 mL), and dried over $Na_2SO_4$. After filtration, removal of the solvent under reduced pressure gave the title compound 1b (quantitative yield) as an oil. $^1H$ NMR (400 MHz, $CDCl_3$): δ 1.48 (d, J=6.4 Hz, 3H), 3.58 (m, 2H), 5.31 (m, 1H), 7.43 (t, J=7.6 Hz, 2H), 7.53 (t, J=7.6 Hz, 1H), 8.05 (d, J=7.2 Hz, 2H).

Step C: (2R)-2-Phenylcarbonyloxypropyl (2S)-2-(tert-butoxycarbonyl)amino-3-(3,4-dihydroxyphenyl)propanoate (1c)

A suspension of (1R)-2-bromo-1-methylethyl benzoate 1b (4.98 g, 20.6 mmol), (2S)-3-(3,4-dihydroxyphenyl)-2-[(tert-butoxycarbonyl)amino]propanoic acid, tetrabutylammonium salt 1a (7.3 g, 25 mmol), and cesium bicarbonate (4.85 g, 25 mmol) in N,N-dimethylacetamide (100 mL) was stirred at 55° C. for 16 h. The solvent was evaporated under vacuum. Ethyl acetate was added to the residue and the resulting solution was washed with water, then 5% $NaHCO_3$ and brine, and dried over $Na_2SO_4$. After removing the solvent under reduced pressure, chromatography (silica gel, 30% ethyl acetate in hexane) of the residue gave 6.3 g (68% yield) of the title compound 1c as a white solid. $^1H$ NMR (400 MHz, $CD_3OD$): δ 1.25 (s, 9H), 1.40 (d, J=6.4 Hz, 3H), 2.99 (dd, J=7.6, 14.4 Hz, 1H), 3.10 (dd, J=5.6, 14.4 Hz, 1H), 4.24 (dd, J=5.6, 7.4 Hz, 1H), 4.38 (dd, J=6.8, 11.6 Hz, 1H), 4.52 (dd, J=3.2, 11.6 Hz, 1H), 5.40 (m, 1H), 6.53 (dd, J=2.2, 8.4 Hz, 1H), 6.66 (d, J=2.2 Hz, 1H), 6.69 (d, J=8.4 Hz, 1H), 7.47 (t, J=7.6 Hz, 2H), 7.60 (t, J=7.6 Hz, 1H), 8.02 (d, J=7.6 Hz, 2H). MS (ESI) m/z 360.15 $(M+H)^+$ and 358.09 $(M-H)^-$.

Method 1

Step D: (2R)-2-Phenylcarbonyloxypropyl (2S)-2-amino-3-(3,4-dihydroxyphenyl)propanoate hydrochloride (1d)

A solution of (2R)-2-phenylcarbonyloxypropyl (2S)-2-(tert-butoxycarbonyl)amino-3-(3,4-dihydroxyphenyl)propanoate 1c (6.3 g, 13.7 mmol) in 50 mL of 4N HCl in dioxane was stirred at room temperature for 30 min. The mixture was concentrated to dryness under reduced pressure. The resulting residue was dissolved in ca. 20 mL of anhydrous acetonitrile and 4 mL of ether. The solution was refrigerated, and the resulting white precipitate was filtered, washed with ether, and dried under vacuum to afford 4.7 g (87% yield) of the hydrochloride salt 1d as a white solid. $^1H$ NMR (400 MHz, $CD_3OD$): δ 1.40 (d, J=6.4 Hz, 3H), 2.99 (dd, J=7.6, 14.4 Hz, 1H), 3.10 (dd, J=5.6, 14.4 Hz, 1H), 4.24 (dd, J=6, 8 Hz, 1H), 4.38 (dd, J=6.8, 11.6 Hz, 1H), 4.52 (dd, J=3.2, 11.6 Hz, 1H), 5.40 (m, 1H), 6.52 (dd, J=2.2, 8.4 Hz, 1H), 6.66 (d, J=2.2 Hz, 1H), 6.69 (d, J=8.2 Hz, 1H), 7.47 (t, J=7.6 Hz, 2H), 7.60 (t, J=7.6 Hz, 1H), 8.02 (d, J=7.6 Hz, 2H). MS (ESI) m/z 360.15 $(M+H)^+$ and 358.09 $(M-H)^-$.

Step E: (2R)-2-Phenylcarbonyloxypropyl (2S)-2-amino-3-(3,4-dihydroxyphenyl)propanoate mesylate, anhydrous (1)

A solution of $NaHCO_3$ (9.87 g, 117.5 mmol) in water (80 mL) was slowly added to a solution of hydrochloride salt 1d (31.0 g, 78.3 mmol) in water (300 mL). The resulting aqueous suspension was extracted with ethyl acetate (EtOAc) (2×400 mL). The combined EtOAc extract was washed with water, then brine, and dried through $MgSO_4$. Methanesulfonic acid (6.04 mL, 93.12 mmol) was slowly added to the ethyl acetate (EtOAc) solution while stirred. White precipitate formed as soon as the addition of methanesulfonic acid was complete. The suspension was stirred for another 30 min and then filtered. The filter cake was washed three times with ethyl acetate (EtOAc) and vacuum dried overnight to afford 35.4 g (quantitative yield) of anhydrous mesylate salt 1 as a white solid. $^1H$ NMR (400 MHz, $CD_3OD$): δ 1.40 (d, J=6.4 Hz, 3H), 2.70 (s, 3H), 2.98 (dd, J=7.8, 14.6 Hz, 1H), 3.10 (dd, J=5.6, 14.4 Hz, 1H), 4.24 (dd, J=5.8, 7.8 Hz, 1H), 4.38 (dd, J=6.8, 12.0 Hz, 1H), 4.52 (dd, J=3.4, 11.8 Hz, 1H), 5.40 (dp, J=3.2, 6.4 Hz, 1H), 6.52 (dd, J=2.2, 8.2 Hz, 1H), 6.67 (d, J=2.2 Hz, 1H), 6.69 (d, J=8.0 Hz, 1H), 7.47 (t, J=7.6 Hz, 2H), 7.60 (br t, J=7.4 Hz, 1H), 8.01 (d, J=7.6 Hz, 2H). MS (ESI) m/z 360.07 $(M+H)^+$ and 358.01 $(M-H)^-$.

Method 2

Methanesulfonic acid (3.9 mL, 60.1 mmol) was slowly added to a solution of (2R)-2-phenylcarbonyloxypropyl (2S)-2-(tert-butoxycarbonyl)amino-3-(3,4-dihydroxyphenyl)propanoate 1e (11.0 g, 22.1 mmol) in 1,4-dioxane (30 mL) while stirred at room temperature. The mixture was stirred for 2 h. The solution was slowly added to methyl tert-butyl ether (MTBE) (600 mL) with vigorous stirring. The resulting suspension was filtered. The filter cake was washed three times with methyl tort-butyl ether and air dried to afford 5.48 g (54% yield) of anhydrous mesylate salt 1 as an off-white solid.

Method 3

A solution of (2R)-2-phenylcarbonyloxypropyl (2S)-2-(tert-butoxycarbonyl)amino-3-(3,4-dihydroxyphenyl)propanoate 1c (10.5 g, 21.1 mmol) in 34 mL (6.0 eq) of 4.0 N HCl/1,4-dioxane was stirred at room temperature for 1 h. Methanesulfonic acid (1.48 mL, 22.8 mmol) was slowly added to the reaction mixture while stirred at room temperature. The solution was concentrated under vacuum to afford the anhydrous mesylate salt 1 as a brown solid.

Example 2

Preparation of Crystalline Anhydrous (2R)-2-Phenylcarbonyloxypropyl (2S)-2-Amino-3-(3,4-dihydroxyphenyl)propanoate Mesylate (1)

Anhydrous mesylate salt 1 (10.0 g, 22.0 mmol) was dissolved in 200 mL of isopropanol at 70° C. and the resulting solution was cooled to room temperature. Filtration afforded 5.8 g (58% yield) of the crystalline anhydrous mesylate salt 1 as a white crystalline solid (m.p. 160.5-161.3° C.). Other solvents and methods useful for crystallizing anhydrous (2R)-2-phenylcarbonyloxypropyl (2S)-2-amino-3-(3,4-dihydroxyphenyl)propanoate mesylate 1 are disclosed in U.S. Pat. No. 7,563,821.

Example 3

Preparation of Crystalline (2R)-2-Phenylcarbonyloxypropyl (2S)-2-Amino-3-(3,4-dihydroxyphenyl)propanoate Mesylate, Hydrate Method 1

High Shear Wet Granulation

Anhydrous (2R)-2-phenylcarbonyloxypropyl (2S)-2-amino-3-(3,4-dihydroxyphenyl)propanoate mesylate (138.6 g) and hydroxypropylmethyl cellulose (1.4 g) (Methocer HPMC E4M, Dow Chemical) were weighed and sieved through an 18-mesh screen. The screened materials were placed into a high shear wet granulator (KG-5 high sheer blender, 5 L bowl, Key International) and pre-blended for 2 min. Water was weighed out (USP, 9.8 g, 7 wt-%). The material was blended for ca. 10-20 min at an impeller speed of 250 rpm and a chopper speed of 2,000 rpm, and a water spray rate of 2 g/min. After granulation the wet granules were milled through a 16-mesh screen with a brush. The milled wet granules were placed in a dryer (UniGlatt Fluid Bed Dryer, Glatt GmbH) and dried for 24 min at an inlet temperature of 65° C. with airflow adjusted at 8-10 SCFM. The dried granules were milled by manually pressing the granules through a screen. As shown by powder X-ray diffraction analysis, the granules comprised a combination of the anhydrous and hydrated forms of (2R)-2-phenylcarbonyloxypropyl (2S)-2-amino-3-(3,4-dihydroxyphenyl)propanoate mesylate.

Using similar processing conditions and 15 wt-% water, the granules contain predominantly crystalline (2R)-2-phenylcarbonyloxypropyl (2S)-2-amino-3-(3,4-dihydroxyphenyl)propanoate mesylate, hydrate.

Method 2

Crystallization from Alcohol/Water

Anhydrous (2R)-2-phenylcarbonyloxypropyl (2S)-2-amino-3-(3,4-dihydroxyphenyl)propanoate mesylate (1 g) was suspended in ca. 1 mL isopropanol/water mixture (40/60 v/v). The suspension was stirred at 700 rpm at 25° C. The solid completely dissolved with time (ca. 2 h) and then gradually precipitated out as (2R)-2-phenylcarbonyloxypropyl (2S)-2-amino-3-(3,4-dihydroxyphenyl)propanoate mesylate, hydrate as determined by PXRD analysis.

Example 4

Preparation of Granules Comprising Crystalline (2R)-2-Phenylcarbonyloxypropyl (2S)-2-amino-3-(3, 4-dihydroxyphenyl)propanoate mesylate and Surfactant Crystalline (2R)-2-phenylcarbonyloxypropyl (2S)-2-amino-3-(3,4-dihydroxyphenyl)propanoate mesylate was first screened through a 16-mesh screen. The screened crystalline (2R)-2-phenylcarbonyloxypropyl (2S)-2-amino-3-(3, 4-dihydroxyphenyl)propanoate mesylate (98 wt-%), sodium lauryl sulfate (1 wt-%, Fischer Scientific), and hydroxypropylmethylcellulose (1 wt-%, Methocer E4M, Dow Chemical, Midland, Mich.) were combined in a 1 L bowl of a KG-5 high shear wet granulator. The dry blend was premixed for 2 minutes, and a total amount of 7 wt-% to 9 wt-% water was sprayed into the granulator using a 0.8 mm nozzle and L/S 14 tubing for about 12 to 13 minutes (about 1 rpm). The impeller speed was about 325 rpm, the chopper speed about 1990 rpm, and the current about 70 Amps to about 120 Amps. The granules were then passed through a CoMil using a 0.079 G (grated) screen or through a size 16 mesh hand screen. The milled granules were then dried for about 15 minutes using a GPCG2 fluid bed drier (Glatt, GmbH) at an inlet temperature of about 55° C. The dried granules were passed through a CoMil using a 0.05 G (grated) screen set at 1500 rpm. For different lots, the granules exhibited a density from about 0.55 g/mL to about 0.59 g/mL; a tap density from about 0.63 g/mL to about 0.68 g/mL, a compressibility index from about 13% to about 14%; a Hausner ratio from about 1.15 to about 1.16, and a Flodex value from about 6 mm to about 9 mm.

Larger granule quantities were prepared using, for example, the following procedure. Crystalline (2R)-2-phenylcarbonyloxypropyl (2S)-2-amino-3-(3,4-dihydroxyphenyl)propanoate mesylate (452.9 g, 98 wt-%) was sifted through a 16 mesh, and hydroxypropylmethylcellulose (4.62 g, 1 wt-%, Methocel™ E4M, Dow Chemical, Midland, Mich.) and sodium lauryl sulfate (4.62 g, 1 wt-%) were sifted through a 16 mesh hand screen. The sifted materials were placed into a KG-5 granulator and pre-blended for 2 minutes at an impeller speed of ca. 250 rpm and a chopper speed of ca. 2,000 rpm. At an impeller speed of ca. 240-260 rpm and a chopper speed of ca. 1,900 to 2,100 rpm, 23.1 g purified water (5 wt-%) was added at a spray rate of ca. 2.6 g per minute to initiate the granulation process. Additional water (e.g., 17 g) was added as necessary to facilitate granulation. The wet granules were then sifted through a 16 mesh hand screen. The wet granules were loaded into a UniGlatt fluid bed drier and the granules dried at an inlet temperature set point of 55° C. to an LOD<1% (about 20 min). The dried granules were discharged and sieved through a 20 mesh screen.

Example 5

Tablet Dosage Forms

Oral tablet dosage forms comprising crystalline (2R)-2-phenylcarbonyloxypropyl (2S)-2-amino-3-(3,4-dihydroxyphenyl)propanoate mesylate and surfactant were prepared according to the following procedures.

SR4 Tablets

Granules (168 g) prepared according to Example 4 and hydroxypropylmethylcellulose (30 g, Methocel™ H100M, Colorcon) were added to a V-blender shell and mixed for 10 min. Magnesium stearate (2 g, Mallinckrodt, Philipsburg, N.J.) was added and the combination blended for an additional 3 min. Tablets were prepared using a Korsch Model XL100 tableting press to provide tablets with a mean weight of 299 mg and a hardness ranging from 8 kp to 15 kp.

For larger lots, granules (462.14 g) prepared according to Example 4 were transferred to a 2-quart V-shell blender. Hydroxypropylmethylcellulose (82.52 g, Methocel™ K100M, Dow Chemical, Midland, Mich.) was sieved through a 20 mesh screen and added to the 2-quart blender and the combination blended for 15 min. Magnesium stearate (5.502 g, Mallinckrodt, Philipsburg, N.J.) was sieved through a 20 mesh screen, added to the 2-quart V-shell blender, and the combination blended for ca. 4 min. To prepare tablets, the blend was charged to a Globe Pharma Mini Press (GlobePharma, New Brunswick, N.J.) with 2-stations of 13/32 standard concave tooling (plain/plain). Tablets weighing about 246 mg were prepared containing about 241 mg of crystalline (2R)-2-phenylcarbonyloxypropyl (2S)-2-amino-3-(3,4-dihydroxyphenyl)propanoate mesylate corresponding to about 190 mg-equivalents of levodopa.

TABLE 1

Example composition of SR4 tablets.

| Component | Percentage (wt-%) | Weight per Tablet (mg) |
|---|---|---|
| Levodopa Prodrug | 82.32 | 246.16 |
| Sodium lauryl sulfate | 0.84 | 2.51 |
| HPMC (Methocel ™ E4M) | 0.84 | 2.51 |
| HPMC (Methocel ™ K100M) | 15.00 | 44.85 |
| Magnesium Stearate | 1.00 | 2.99 |
| Total | 100.00 | 299.02 |

SR5 Tablets

Granules (134 g) prepared according to Example 4, hydroxypropylmethylcellulose (30 g, Methocer K100M, Colorcon), and fumaric acid (34 g, granular, Spectrum Laboratory Products, Gardena, Calif.) were added to a V-blender shell (2 quart, Model MaxiBlend-1, GlobePharma, New Brunswick, N.J.) and mixed for 10 min. Magnesium stearate (2 g, Mallinckrodt, Philipsburg, N.J.) was added to the blend and mixed for an additional 3 min. Tablets were prepared from the blend using a Korsch Model XL100 tableting press to obtain tablets having a mean weight of 375 mg (±5%) and a hardness ranging from 8 kp to 10 kp.

For larger lots granules (462.14 g, 67 wt-%) prepared according to Example 4 were transferred to a 2-quart V-shell blender. Hydroxypropylmethylcellulose (103.5 g, 15 wt-%, Methocel™ K100M, Colorcon) and fumaric acid (117.2 g, 17 wt-%, Spectrum Laboratory Products, Gardena, Calif.) were sieved through a 20 mesh screen and added to the 2-quart blender and the combination blended for 15 min. Magnesium stearate (6.9 g, 1.0 wt-%. Mallinckrodt, Philipsburg, N.J.) was sieved through a 20 mesh screen, added to the 2-quart V-shell blender, and the combination blended for ca. 4 min. To prepare tablets, the blend was charged to a GlobePharma Mini Press (GlobePharma, New Brunswick, N.J.) with 2-stations of 13/32 standard concave tooling (plain/plain). Tablets weighing about 246 mg were prepared containing about 241 mg of crystalline (2R)-2-phenylcarbonyloxypropyl (2S)-2-amino-3-(3,4-dihydroxyphenyl)propanoate mesylate corresponding to about 190 mg-equivalents of levodopa.

TABLE 2

Example composition of SR5 tablets.

| Component | Percentage (wt-%) | Weight per Tablet (mg) |
|---|---|---|
| Levodopa Prodrug | 65.67 | 246.16 |
| Sodium lauryl sulfate | 0.67 | 2.51 |
| HPMC (Methocel ™ E4M) | 0.67 | 2.51 |
| HPMC (Methocel ™ K100M) | 15.00 | 56.23 |
| Fumaric acid | 17.00 | 63.72 |
| Magnesium Stearate | 1.00 | 3.75 |
| Total | 100.00 | 374.88 |

Dissolution profiles for SR4 and SR5 tablets were determined using USP Apparatus II (paddles) at a stirring speed of 50 rpm, a temperature of 37° C.±0.5° C. in 900 mL of 0.1N HCl, pH 1.2. Dissolution profiles (mean±SD) for the SR4 and SR5 tablets prepared according to the above procedures are shown in FIG. 1.

Example 6

Powder X-Ray Diffraction Analysis of Granules

Powder X-ray diffraction (PXRD) analysis was performed using a PANalytical X'Pert Pro X-ray diffractometer. The X-ray source was Cu $k_{\alpha 1}$ with output voltage of 45 kV and current of 40 mA. The instrument employed para-focusing Bragg-Brentano geometry with incident divergence and scattering slits set at $1/16°$ and $1/8°$, respectively. Soller slits with a 0.04-mm radius were used for both the incident and diffracted beams to remove axial divergence. Powder samples (9-12 mg) were gently pressed onto a single crystal silicon sample holder to form a smooth surface, and samples were spun at 8 sec/revolution throughout the data acquisition process. The samples were scanned from 2° to 40°(2θ°) with a step size of 0.017° (2θ angle) and a scan speed of 0.067°/sec. Data acquisition was controlled and analyzed with X'Pert Data Collector Software (version 2.2d) and X'Pert Data Viewer (version 1.2c), respectively.

PXRD patterns of granules prepared without sodium lauryl sulfate (Example 3) confirm the transformation of the anhydrous form of crystalline (2R)-2-phenylcarbonyloxypropyl (2S)-2-amino-3-(3,4-dihydroxyphenyl)propanoate mesylate to the hydrate during high shear wet granulation using a water content of 9 wt-% and 15 wt-% (FIG. 3). The PXRD pattern for anhydrous (2R)-2-phenylcarbonyloxypropyl (2S)-2-amino-3-(3,4-dihydroxyphenyl)propanoate mesylate is shown in pattern A of FIG. 3 and the PXRD patterns of (2R)-2-phenylcarbonyloxypropyl (2S)-2-amino-3-(3,4-dihydroxyphenyl)propanoate mesylate, hydrate obtained without sodium lauryl sulfate and using a water content of 9 wt-% and 15 wt-% as shown in patterns B and C are characteristic of the hydrated form.

As shown in FIG. 2, when the same granulation is performed with 1% sodium lauryl sulfate (SLS), crystalline (2R)-2-phenylcarbonyloxypropyl (2S)-2-amino-3-(3,4-dihydroxyphenyl)propanoate mesylate did not transform to the hydrate (compare PXRD of SR5 tablet with 1% SLS, and PXRD patterns in FIG. 3). Crystalline (2R)-2-phenylcarbonyloxypropyl (2S)-2-amino-3-(3,4-dihydroxyphenyl)propanoate mesylate in tablets made from granules containing 1 wt-% sodium lauryl sulfate also did not undergo form conversion under the stressed condition of 40° C. and 75% RH for at least four weeks (FIG. 2).

Example 7

Open Dish Stability of Tablets

The open dish stability of SR4 and SR5 tablets prepared according to Example 5 was determined. Appearance, assay, impurities/degradants, dissolution profile, water content, and PXRD were assessed following storage at (a) 2° C. to 8° C.; (b) 25° C./60% RH; and (c) 40° C./20% RH.

For storage condition (a) no significant changes were observed after 4 weeks. For storage conditions (b) and (c) no significant changes were observed after 3 months.

Example 8

Levodopa Pharmacokinetic Profiles Following Administration of SR4 or SR5 Tablets The levodopa pharmacokinetics was measured following administration of two (2) SR4 or SR5 tablets (see Example 5) to twelve (12) fed or fasted healthy human subjects. A dose corresponds to 208 mg levodopa.

Subjects dosing under fed conditions were served a high-fat (approximately 50 percent of total caloric content of the meal) and high-calorie (approximately 800 to 1000 calories) meal for breakfast, approximately 30 minutes prior to dosing. The meal derived approximately 150, 250, and 500-600 calories from protein, carbohydrate, and fat, respectively. Within 10 minutes following consumption of the high fat breakfast, subjects received the dose of levodopa prodrug as SR4 or SR5 tablets with 240 mL of non-carbonated water.

Blood samples (5 mL) were collected in Vacutainers® or Monovette® tubes containing potassium K2-EDTA. Six-hundred fifty (650) µL of 10% sodium metabisulfite was added to the tubes within 1 minute of blood collection, and the tubes gently inverted 10 to 15 times. Within 2 minutes of blood collection, 1 mL of whole blood was transferred into Nalgene Cryovial tubes containing 3 mL of chilled quenching media. These tubes were gently inverted 10 to 15 times and vortexed for 30 seconds upside down and for 30 seconds right side up. Within 30 seconds of quenching, the blood samples were stored at −70±10° C. prior to analysis.

Levodopa concentration in the blood samples was determined using sensitive and specific LC-MS/MS methods. Concentration data were analyzed by non-compartmental methods using the software program WinNonlin™ (Pharsight Corporation, Mountain View, Calif.). The following pharmacokinetic parameters were determined: $C_{max}$ (maximum concentration), $T_{max}$ (time to maximum concentration), $C_8$ (concentration at 8 hours), Kel (terminal elimination rate constant), $T_{1/2}$ (apparent elimination half-life (calculated as 0.693/Kel), $AUC_{inf}$ (area under the blood concentration-time curve extrapolated to infinity calculated as $AUC_{inf}=AUC_{last}+C_t/Kel$ where $C_t$ is the last quantifiable concentration and Kel is the terminal elimination rate constant), and $F_{rel}(\%)$ is the relative oral bioavailability of levodopa.

Levodopa pharmacokinetic profiles (mean±SD) following oral administration of SR4 or SR5 tablets to fed or fasted subjects are shown in FIG. 4 and FIG. 5, respectively. The levodopa pharmacokinetic parameters following oral administration of SR4 or SR5 tablets are provided in Table 3 and Table 4, respectively.

TABLE 3

Levodopa pharmacokinetic parameters following administration of SR4 or SR5 dosage forms to fasted subjects.

| Treatment | N | Mean (SD) Pharmacokinetic Parameters for Levodopa | | | | | |
|---|---|---|---|---|---|---|---|
| | | $C_{max}$ (µg/mL) | $T_{max}$ (hr) | $T_{1/2}$ (hr) | $AUC_{inf}$ (µg*hr/mL) | $C_{8\,hr}$ (µg/mL) | $F_{rel}$ (%) |
| SR4 Fasted | 12 | 0.76 (0.17) | 1.88 (1.05) | 2.37 (0.45) | 3.88 (0.81) | 0.14 (0.07) | 61.7 (8.8) |
| SR5 Fasted | 12 | 0.70 (0.21) | 2.75 (1.20) | 2.96 (0.88) | 3.78 (1.04) | 0.163 (0.11) | 59.4 (7.6) |

TABLE 4

Levodopa pharmacokinetic parameters following administration of SR4 or SR5 dosage forms to fed subjects.

| Treatment | N | Mean (SD) Pharmacokinetic Parameters for Levodopa | | | | | |
|---|---|---|---|---|---|---|---|
| | | $C_{max}$ (µg/mL) | $T_{max}$ (hr) | $T_{1/2}$ (hr) | $AUC_{inf}$ (µg*hr/mL) | $C_{8\,hr}$ (µg/mL) | $F_{rel}$ (%) |
| SR4 Fed | 12 | 0.88 (0.34) | 4.42 (1.08) | 2.29 (0.76) | 5.22 (1.68) | 0.40 (0.16) | 76.3 (13.8) |
| SR5 Fed | 12 | 0.77 (0.28) | 4.58 (1.24) | 2.83 (1.17) | 5.07 (1.43) | 0.37 (0.14) | 74.2 (10.6) |

Example 9

Bilayer Tablets

Bilayer tablets containing crystalline (2R)-2-phenylcarbonyloxypropyl (2S)-2-amino-3-(3,4-dihydroxyphenyl)propanoate mesylate (levodopa prodrug) and carbidopa were prepared according to the following procedure. Hypromellose 2910, hypromellose 2208, sodium lauryl sulfate, mannitol (e.g., Pearlitol® 100SD, Pearlitol® 200SD, and Pearlitol® 50C), microcrystalline cellulose (E4M Premium, Dow Chemical), and crospovidone (e.g., Polyplasdone® XL-10) were screened through a no. 30 mesh screen Magnesium stearate (2257 non bovine, Mallickrodt) was screened through a no. 60 mesh screen. Mannitol (Pearlitol® 100 SD, Roquette), carbidopa (Sochinaz), crospovidone (Polyplasdone® XL-10, ISP Technologies), and microcrystalline cellulose (Avicel® PH-101, FMC BioPolymer) were loaded into a high shear granulator and blended with the impeller on and the chopper off. The high shear blend containing carbidopa and the screened magnesium stearate were loaded into a V-blender and blended. The final carbidopa blend was discharged from the V-blender and stored in closed double polyethylene bags until tableting.

Crystalline (2R)-2-phenylcarbonyloxypropyl (2S)-2-amino-3-(3,4-dihydroxyphenyl)propanoate mesylate, hypromellose 2910, and sodium lauryl sulfate (SLS) (S529, Fisher Scientific) were loaded into a high shear granulator, and 7.2 wt-% to 9.7 wt-% water was added with both the impeller and chopper on to produce granules. The wet granules containing levodopa prodrug were passed through a Quadro Comil. The milled granules were then dried in a fluid bed dryer until the LOD was <1.0%. The dried granules containing levodopa prodrug were passed through a Quadro Comil. Hypromellose 2208 (K100M Premium CR, Dow Chemical) was sandwiched between two halves of the dried and milled granules in a V-blender and the combination blended. Magnesium stearate was added to the blend containing the levodopa prodrug granules and blended. The final blend containing levodopa prodrug granules was discharged and stored in closed double polyethylene bags until tableting.

Bilayer tablets were prepared by compressing the levodopa prodrug and carbidopa blends using ⅜-in round, standard concave tooling. To prepare the coating suspension purified water was first weighed out and Opadry was added to the water with agitation. After approximately 1.5 hours of mixing, the suspension was screened through a no. 30 mesh screen. The bilayer tablets were film coated until the target coat weight was achieved.

Bilayer tablets comprising similar constituents and amounts were also prepared using similar procedures.

The composition of various bilayer tablets comprising crystalline (2R)-2-phenylcarbonyloxypropyl (2S)-2-amino-3-(3,4-dihydroxyphenyl)propanoate mesylate (levodopa prodrug) and carbidopa are provided in Tables 5-11. Tablet using compositions shown in Tables 5 and 7-11 were produced, whereas the compositions shown in Table 6 represent proposed ranges for various doses of levodopa prodrug. Levodopa prodrug (free form) refers to the amount of (2R)-2-phenylcarbonyloxypropyl (2S)-2-amino-3-(3,4-dihydroxyphenyl)propanoate and does not include the weight of the mesylate salt. The weight of (2R)-2-phenylcarbonyloxypropyl (2S)-2-amino-3-(3,4-dihydroxyphenyl)propanoate mesylate is 1.268 times greater than the weight of the free from, (2R)-2-phenylcarbonyloxypropyl (2S)-2-amino-3-(3, 4-dihydroxyphenyl)propanoate.

TABLE 5

Composition of bilayer tablets containing 190 mg levodopa prodrug (free form) and 25 mg carbidopa.

| Tablet Component | wt-%/layer | mg/tablet | wt-%/tablet |
|---|---|---|---|
| Levodopa Prodrug | 88.1 | 246.9 | 59.5 |
| HPMC-E4M | 2.75 | 7.7 | 1.8 |
| Sodium lauryl sulfate | 0.9 | 2.5 | 0.6 |
| HPMC-K100M | 8.0 | 22.4 | 5.4 |
| Magnesium Stearate | 0.25 | 0.7 | 0.2 |
| Total in Levodopa Prodrug Layer | 100.0 | 280.2 | 67.5 |
| Carbidopa | 20.0 | 27.0 | 6.5 |
| Avicel ® PH-101 | 19.0 | 25.7 | 6.2 |
| Pearlito ® 100SD | 46.75 | 63.1 | 15.2 |
| Pearlitol ® 50C | 10.0 | 13.5 | 3.2 |
| Polyplasdone ® XL-10 | 3.0 | 4.0 | 1.0 |
| Magnesium Stearate | 1.25 | 1.7 | 0.4 |
| Total in Carbidopa Layer | 100.0 | 135.0 | 32.5 |
| Coating (Opadry Pink 03K94010) | N/A | 16.6 | 4.0 |
| Total Tablet | N/A | 431.8 | 104.0 |

TABLE 6

Composition of bilayer tablets containing 95 mg to 380 mg levodopa prodrug (free form) and 12.5-50 mg carbidopa.

| Tablet Component | 95/12.5 wt-%/layer | 190/25 wt-%/layer | 285/37.5 wt-%/layer | 380/50 wt-%/layer | 380/20 wt-%/layer |
|---|---|---|---|---|---|
| Levodopa Prodrug | 71.5-88 | 76.5-93 | 76.5-93 | 76.5-93 | 76.5-93 |
| Hypromellose 2910 (4M cps) | 0.5-3 | 0.5-3 | 0.5-3 | 0.5-3 | 0.5-3 |
| Sodium lauryl sulfate | 0.5-2.0 | 0.5-2.0 | 0.5-2.0 | 0.5-2.0 | 0.5-2.0 |
| Hypromellose 2208 (100M cps) | 10-20 | 5-15 | 5-15 | 3-15 | 3-15 |
| Magnesium Stearate | 0.5-2 | 0.5-2 | 0.5-2 | 0.5-2 | 0.5-2 |
| Carbidopa | 15-30 | 15-30 | 15-30 | 15-30 | 15-30 |
| Microcrystalline cellulose | 15-40 | 15-40 | 15-40 | 15-40 | 15-40 |
| Mannitol | 35-60 | 35-60 | 35-60 | 35-60 | 35-60 |
| Crospovidone | 1-3 | 1-3 | 1-3 | 1-3 | 1-3 |
| Magnesium Stearate | 0.5-2 | 0.5-2 | 0.5-2 | 0.5-2 | 0.5-2 |

TABLE 7

Composition of bilayer tablets containing 190 mg levodopa prodrug (free form) and 25 mg carbidopa.

| Tablet Component | a wt %/layer | b wt %/layer | c wt %/layer | d wt %/layer | e wt %/layer | f wt %/layer | g wt %/layer | h wt %/layer |
|---|---|---|---|---|---|---|---|---|
| Levodopa prodrug | 89.7 | 87.2 | 84.8 | 82.4 | 89.52 | 87.6 | 85.68 | 88.56 |
| Hypromellose 2910 (4M cps) | 0.9 | 0.9 | 0.9 | 0.8 | 2.8 | 2.74 | 2.68 | 2.77 |
| Sodium lauryl sulfate | 0.9 | 0.9 | 0.9 | 0.8 | 0.93 | 0.91 | 0.89 | 0.92 |
| Hypromellose 2208 (100M cps) | 7.5 | 10 | 12.5 | 15 | 6 | 8 | 10 | 7 |
| Magnesium Stearate | 1 | 1 | 1 | 1 | 0.75 | 0.75 | 0.75 | 0.75 |
| Carbidopa | 20 | 20 | 20 | 20 | 20 | 20 | 20 | 20 |
| Microcrystalline cellulose | 38 | 38 | 38 | 38 | 19 | 19 | 19 | 19 |
| Mannitol | 38 | 38 | 38 | 38 | 57 | 57 | 57 | 57 |
| Crospovidone | 3 | 3 | 3 | 3 | 3 | 3 | 3 | 3 |
| Magnesium Stearate | 1 | 1 | 1 | 1 | 1 | 1 | 1 | 1 |

TABLE 8

Composition of BL2-A and BL2-B bilayer tablets containing 190 mg levodopa prodrug (free form) and 25 mg carbidopa.

| | BL2-A/B (190 mg levodopa prodrug (free form)/ 25 mg carbidopa) | | |
|---|---|---|---|
| Tablet Component | wt-%/layer | mg/tablet | wt-%/tablet |
| Levodopa prodrug (mesylate salt) | 87.3 | 240.7 | 58.6 |
| HPMC-E4M | 2.7 | 7.6 | 1.8 |
| Sodium lauryl sulfate | 0.9 | 2.5 | 0.6 |
| HPMC-K100M | 8.0 | 22.0 | 5.4 |
| Magnesium stearate | 1.0 | 2.8 | 0.6 |
| Total in levodopa prodrug layer | 100.0 | 275.6 | 67.0 |

TABLE 8-continued

Composition of BL2-A and BL2-B bilayer tablets containing 190 mg levodopa prodrug (free form) and 25 mg carbidopa.

| Tablet Component | BL2-A/B (190 mg levodopa prodrug (free form)/ 25 mg carbidopa) | | |
|---|---|---|---|
| | wt-%/layer | mg/tablet | wt-%/tablet |
| Carbidopa Monohydrate | 20.0 | 27.0 | 6.6 |
| Avicel ® PH-101 | 19.0 | 25.7 | 6.3 |
| Pearlitol ® 100SD | 57.0 | 77.0 | 18.8 |
| Polyplasdone ® XL-10 | 3.0 | 4.0 | 1.0 |
| Magnesium stearate | 1.0 | 1.3 | 0.3 |
| Total in carbidopa layer | 100.0 | 135.0 | 33.0 |
| Coating (Opadry Pink 03K94010) | N/A | 16.4 | 4.0 |
| Total Tablet | N/A | 427.0 | 104.0 |

TABLE 9

Composition of BL2-C bilayer tablets containing 190 mg levodopa prodrug (free form) and 25 mg carbidopa.

| Tablet Component | BL2-C (190 mg levodopa prodrug (free form)/25 mg carbidopa) | | |
|---|---|---|---|
| | wt-%/layer | mg/tablet | wt-%/tablet |
| Levodopa prodrug (mesylate salt) | 87.8 | 240.7 | 58.9 |
| HPMC-E4M | 2.8 | 7.6 | 1.8 |
| Sodium lauryl sulfate | 0.9 | 2.5 | 0.6 |
| HPMC-K100M | 8.0 | 21.9 | 5.4 |
| Magnesium stearate | 0.50 | 1.3 | 0.3 |
| Total in levodopa prodrug layer | 100.0 | 274.0 | 67.0 |
| Carbidopa Monohydrate | 20.0 | 27.0 | 6.6 |
| Avicel ® PH-101 | 19.0 | 25.7 | 6.3 |
| Pearlitol ® 100SD | 52.0 | 70.2 | 17.1 |
| Pearlitol ® 50C | 5.0 | 6.8 | 1.7 |
| Polyplasdone ® XL-10 | 3.0 | 4.0 | 1.0 |
| Magnesium stearate | 1.0 | 1.3 | 0.3 |
| Total in carbidopa layer | 100.0 | 135.0 | 33.0 |
| Coating (Opadry Pink 03K94010) | N/A | 16.4 | 4.0 |
| Total Tablet | N/A | 425.4 | 104.0 |

TABLE 10

Composition of BL2-D bilayer tablets containing 190 mg levodopa prodrug (free form) and 25 mg carbidopa.

| Tablet Component | BL2-D (190 mg levodopa prodrug (free form)/25 mg carbidopa) | | |
|---|---|---|---|
| | wt-%/layer | mg/tablet | wt-%/tablet |
| Levodopa prodrug (mesylate salt) | 88.1 | 246.9 | 59.5 |
| HPMC-E4M | 2.75 | 7.7 | 1.8 |
| Sodium lauryl sulfate | 0.9 | 2.5 | 0.6 |
| HPMC-K100M | 8.0 | 22.4 | 5.4 |
| Magnesium stearate | 0.25 | 0.7 | 0.2 |
| Total in levodopa prodrug layer | 100.0 | 280.2 | 67.5 |
| Carbidopa Monohydrate | 20.0 | 27.0 | 6.5 |
| Avicel ® PH-101 | 19.0 | 25.7 | 6.2 |
| Pearlitol ® 100SD | 46.75 | 63.1 | 15.2 |
| Pearlitol ® 50C | 10.0 | 13.5 | 3.2 |
| Polyplasdone ® XL-10 | 3.0 | 4.0 | 1.0 |
| Magnesium stearate | 1.25 | 1.7 | 0.4 |
| Total in carbidopa layer | 100.0 | 135.0 | 32.5 |
| Coating (Opadry Pink 03K94010) | N/A | 16.6 | 4.0 |
| Total Tablet | N/A | 431.8 | 104.0 |

TABLE 11

Composition of BL2-E bilayer tablets containing 190 mg levodopa prodrug (free form) and 25 mg carbidopa.

| Tablet Component | BL2-E (190 mg levodopa prodrug (free form)/25 mg carbidopa) | | |
|---|---|---|---|
| | wt-%/layer | mg/tablet | wt-%/tablet |
| Levodopa prodrug (mesylate salt) | 85.4 | 246.9 | 58.2 |
| HPMC-E4M | 2.7 | 7.7 | 1.8 |
| Sodium lauryl sulfate | 0.9 | 2.6 | 0.6 |
| HPMC-K100M | 10.0 | 28.8 | 6.8 |
| Magnesium stearate | 1.0 | 2.9 | 0.7 |
| Total in levodopa prodrug layer | 100.0 | 288.9 | 68.2 |
| Carbidopa Monohydrate | 20.0 | 27.0 | 6.4 |
| Avicel ® PH-102 | 19.1 | 25.8 | 6.1 |
| Pearlitol ® 200SD | 57.15 | 77.2 | 18.2 |
| Polyplasdone ® XL-10 | 3.0 | 4.0 | 0.9 |
| Magnesium stearate | 0.75 | 1.0 | 0.2 |
| Total in carbidopa layer | 100.0 | 135.0 | 31.8 |
| Coating (Opadry OY-S-7322) | N/A | 29.6 | 7.0 |
| Total Tablet | N/A | 452.6 | 107.0 |

Example 10

Dissolution Profiles for Bilayer Tablets

Dissolution profiles for bilayer tablets were obtained using a USP paddle apparatus (Type II) with sinkers in 900 mL of 0.1 N hydrochloric acid at pH 1.2 or pH 5.0 and a temperature of 37° C. The dissolution medium was stirred at 50 rpm. Samples were withdrawn and filtered at 15, 30, and 45 minutes for carbidopa; and at 0.5, 0.75, 2, 4, 6, 9, and 12 hours for levodopa prodrug. The samples were analyzed by HPLC with UV detection at 280 nm against carbidopa and levodopa prodrug external standards.

Representative levodopa prodrug dissolution profiles (mean±SD) at pH 1.2 or pH 5.0 for coated bilayer tablets prepared according to Example 9 and having the composition described in Table 5 are shown in FIG. 6.

Figure 7:
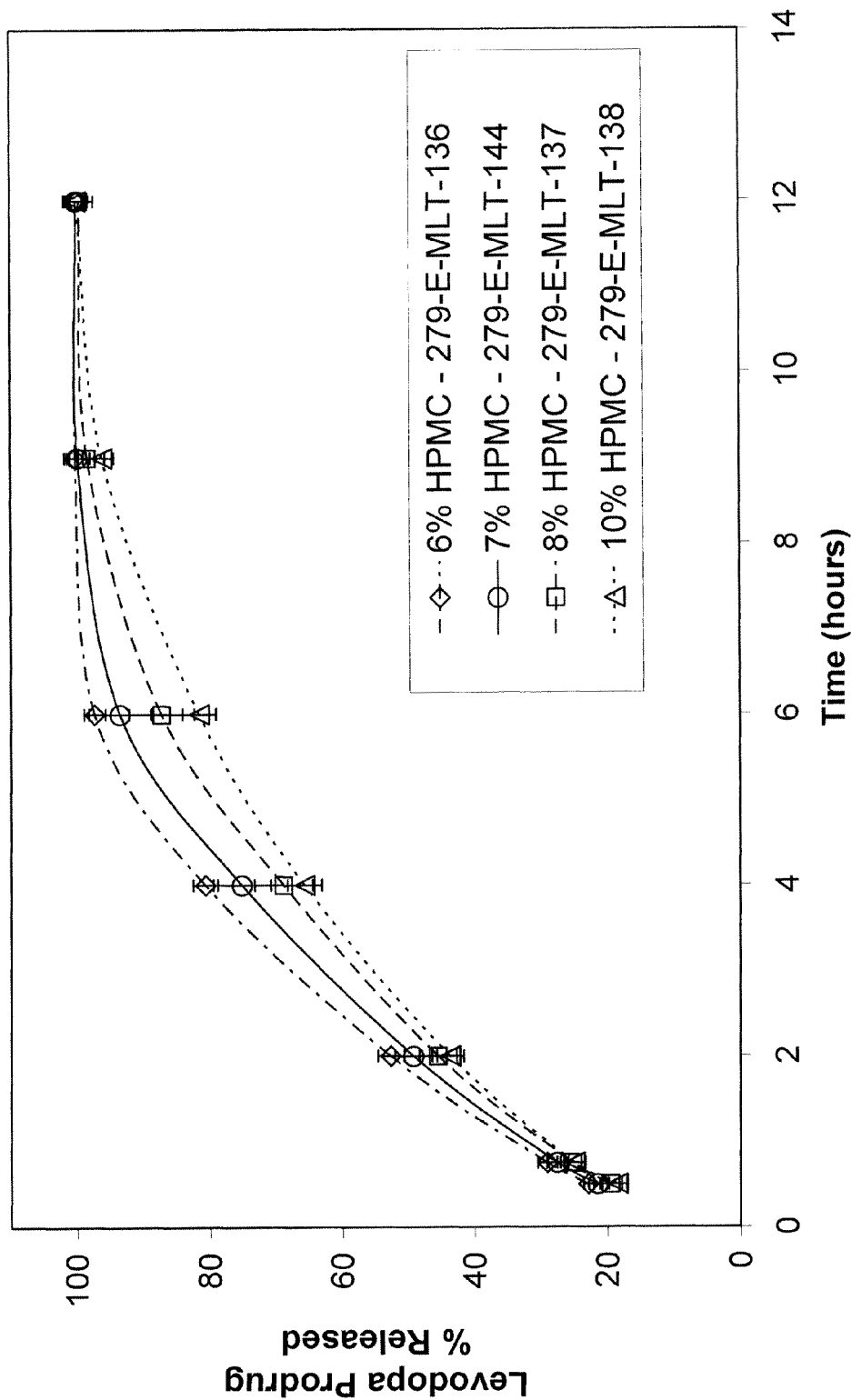
FIG. 7 shows levodopa prodrug dissolution profiles for bilayer tablets prepared according to Example 9 and having the composition of formulations e, f, g, and h as described in Table 7.

Representative levodopa prodrug dissolution profiles (mean±SD) at pH 1.2 (normalized to 100% release at 12 hours) for uncoated bilayer tablets prepared according to Example 9, compressed at 15 kN and having the composition described for formulations −136, −137, −138, −144 in Table 7 are shown in FIG. 7.

Figure 8:
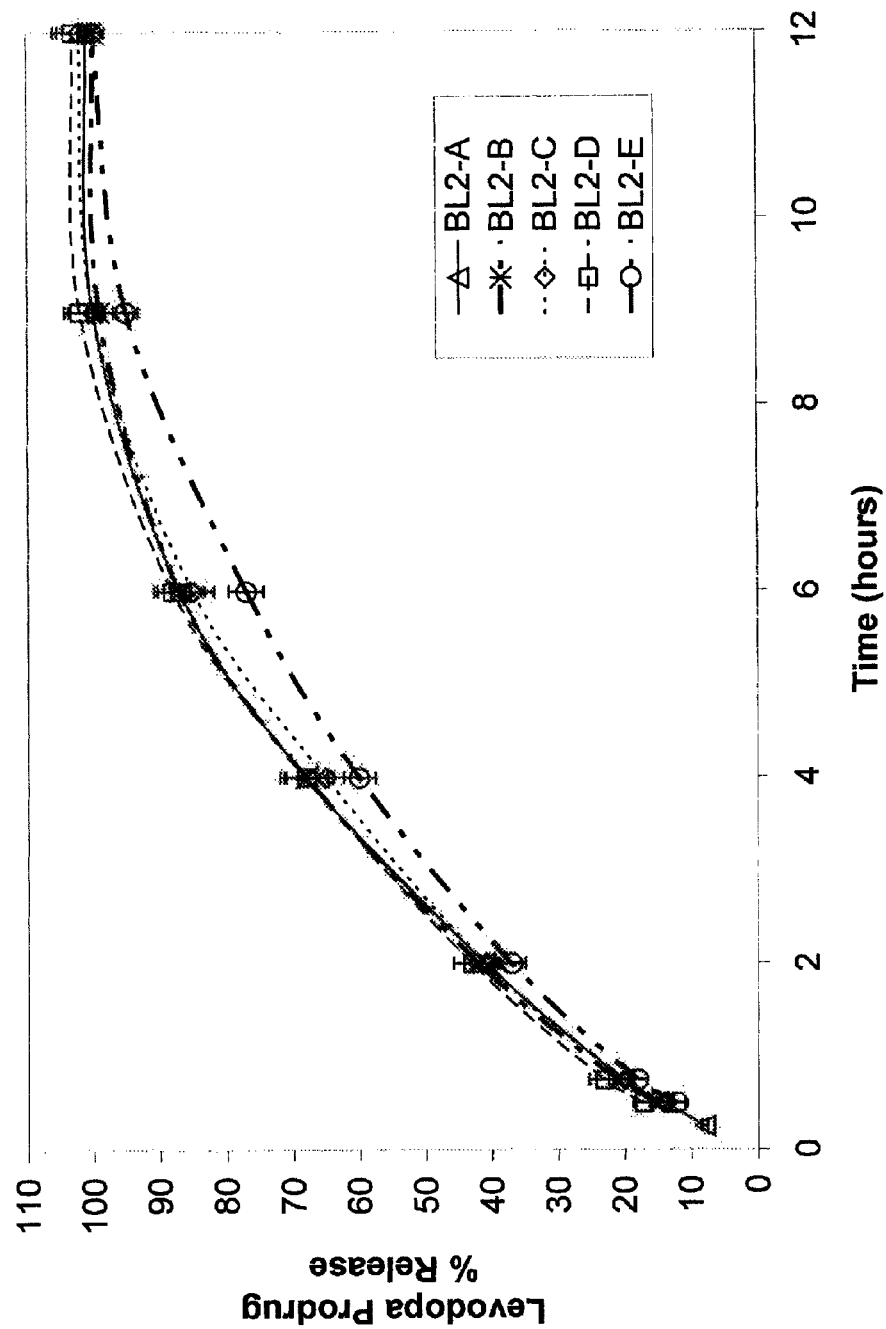
FIG. 8 shows levodopa prodrug dissolution profiles for bilayer tablets prepared according to Example 9 and having the compositions described in Tables 8-11.
Figure 9:
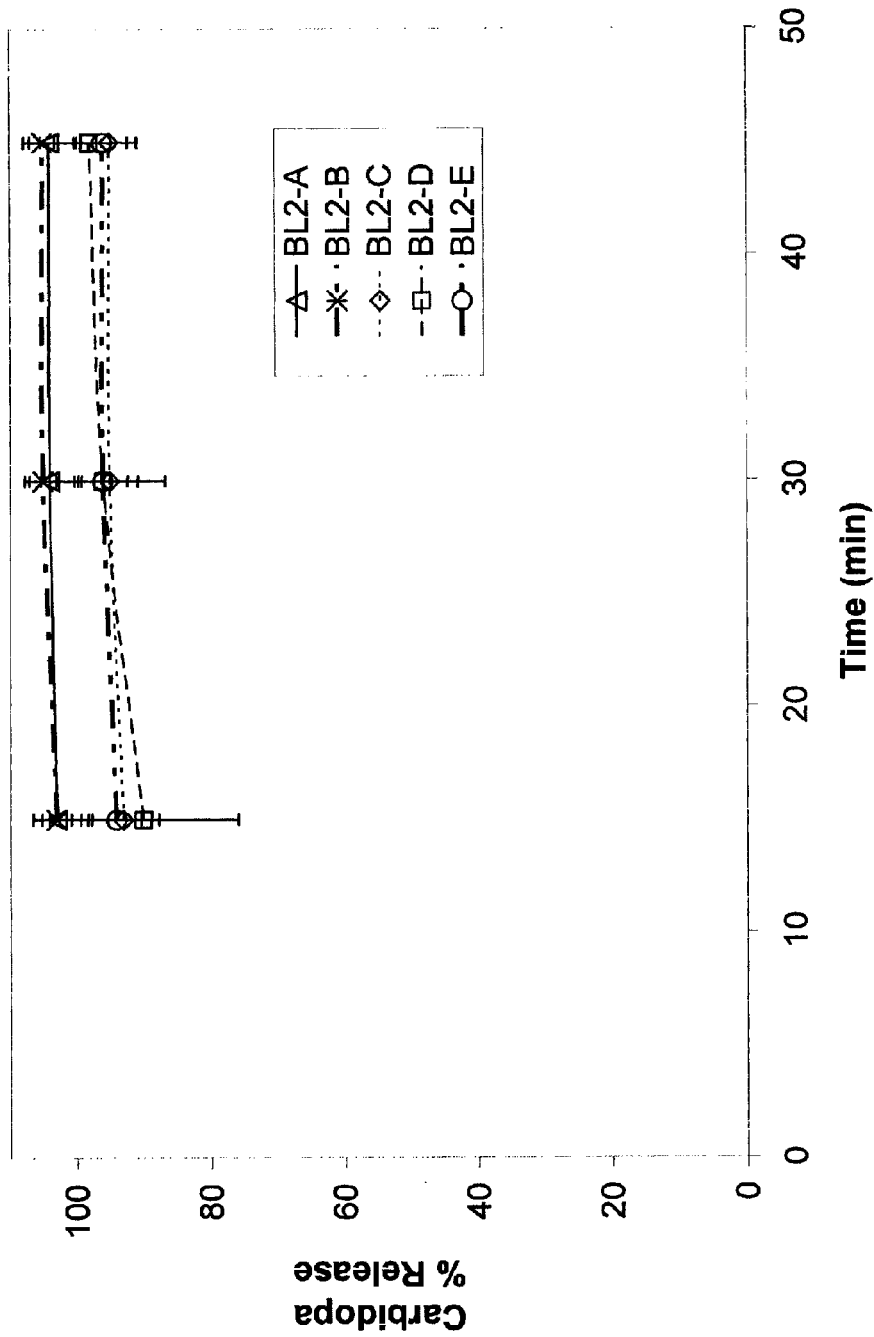
FIG. 9 shows carbidopa dissolution profiles for bilayer tablets prepared according to Example 9 and having the compositions described in Tables 8-11.

Representative levodopa prodrug and carbidopa dissolution profiles (mean±SD) at pH 1.2 for coated bilayer tablets prepared according to Example 9 and having the compositions described in Tables 8-11 are shown in FIG. 8 and FIG. 9, respectively.

Example 11

Clinical Trial in Subjects with Parkinson's Disease

The efficacy of levodopa prodrug administered as BL2 bilayer tablets comprising carbidopa is currently being evaluated in a Phase 2 randomized, double-blind, double-dummy, crossover study in subjects with Parkinson's disease. The study treatment utilizes BL2 tablets (190 mg levodopa prodrug (free form)/25 mg carbidopa bilayer tablets), over-encapsulated (O/E) Sinemet® (100 mg levodopa/25 mg carbidipa tablets), and matching placebos for each treatment. Subjects are randomized in a 1:1:1:1 allocation ratio to 1 of 4 sequences of treatment.

Efficacy is assessed using the Unified Parkinson's Disease Rating Scale (UPDRS) at intervals during the study. An on/off diary maintained by the subjects is used to capture wearing off effects on various motor conditions including: "off"—when medication has worn off and is no longer providing benefit to mobility, slowness and stiffness; "on without dyskinesia"—when medication is providing benefit with regard to mobility, slowness and stiffness, and the subject is not experiencing dyskinesia (involuntary twisting, turning movements); "on with non-troublesome dyskinesia"—when medication is providing benefit with regard to mobility, slowness and stiffness. The subject is experiencing dyskinesia (involuntary twisting, turning movements), but it does not interfere with function or cause meaningful discomfort; and "on with troublesome dyskinesia"—when medication is providing benefit with regard to mobility, slowness and stiffness. The subject is experiencing dyskinesia (involuntary twisting, turning movements) that interferes with function or cause meaningful discomfort. The overall change from baseline in Parkinson's disease symptoms is assessed using both investigator-rated and patient-rated Clinical Global Impression of Improvement (CGI-I).

The change from baseline in mean daily "off" time at end of double blind treatment periods is determined. Changes in mean daily "on" time, mean daily "on" time without troublesome dyskinesia, mean daily "on" time with dyskinesia (troublesome or non-troublesome), mean daily "on" time with troublesome dyskinesia, percentage of awake time "off", percentage of awake time "on", UPDRS II (ADL) and III (Motor) subscale scores and PDQ-39 subscale scores are also assessed. The proportion of subjects achieving ≧30% reduction from baseline in mean daily "off" time, proportion of subjects achieving ≧30% increase from baseline in mean daily "on" time without troublesome dyskinesias and proportion of responders with "much improved" or "very much improved" on the investigator-rated and patient-rated CGI-I are also analyzed. Adverse events are recorded. Median number of days with dyskinesia and median duration of daily on time with dyskinesia are examined from on/off diary data by type (troublesome and non-troublesome) are determined by treatment within each phase.

In addition to the efficacy study, certain subjects are participating in a pharmacokinetic assessment. For subjects participating in the pharmacokinetic study, blood samples are collected in Vacutainers® or Monovette® tubes containing K2-EDTA at intervals following administration of BL2 or Sinemet® tablets. Blood samples are drawn within about 5 minutes of the specified post-dose nominal time point for sampling, e.g., 0, 0.5, 1, 1.5, 2, 3, 4, 5, 6, 7, 8, 9, 10, 12, 14, and 16 hours post-dose. Samples are quenched within 1 minute and centrifuged within 15 minutes). Plasma samples are analyzed by a sensitive and specific LC-MS/MS method for determination of concentrations of levodopa, 3-O-methyldopa, carbidopa, and other possible metabolites.

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

What is claimed is:

1. A pharmaceutical composition comprising granules, wherein the granules are prepared using high shear wet granulation and comprise:
   90 wt % to 99 wt % anhydrous crystalline (2R)-2-phenylcarbonyloxypropyl (2S)-2-amino-3-(3,4-dihydroxyphenyl)propanoate mesylate; and
   0.5 wt % to 2 wt % $C_{6-18}$ alkylsulfate or pharmaceutically acceptable salt thereof.

2. The pharmaceutical composition of claim 1, wherein the $C_{6-18}$ alkylsulfate or pharmaceutically acceptable salt thereof is sodium lauryl sulfate.

3. The pharmaceutical composition of claim 1, comprising one or more pharmaceutically acceptable excipients.

4. A pharmaceutical composition comprising:
   about 50 wt-% to about 90 wt-% anhydrous crystalline (2R)-2-phenylcarbonyloxypropyl (2S)-2-amino-3-(3,4-dihydroxyphenyl)propanoate mesylate;
   about 0.5 wt-% to about 2.0 wt-% $C_{6-18}$ alkylsulfate or pharmaceutically acceptable salt thereof;
   about 6 wt-% to about 20 wt-% hydroxypropylmethylcellulose; and
   about 0.5 wt-% to about 2.0 wt-% magnesium stearate;
   wherein wt-% is based on the total dry weight of the composition.

5. The pharmaceutical composition of claim 1, comprising an L-aromatic amino acid decarboxylase inhibitor, a catechol-O-methyltransferase inhibitor, or a combination of an L-aromatic amino acid decarboxylase inhibitor and a catechol-O-methyltransferase inhibitor.

6. An oral tablet dosage form comprising granules prepared using high shear wet granulation, wherein the granules comprise:
   anhydrous crystalline (2R)-2-phenylcarbonyloxypropyl (2S)-2-amino-3-(3,4-dihydroxyphenyl)propanoate mesylate; and
   a $C_{6-18}$ alkylsulfate or pharmaceutically acceptable salt thereof.

7. The dosage form of claim 6, wherein the $C_{6-18}$ alkylsulfate or pharmaceutically acceptable salt thereof is sodium lauryl sulfate.

8. The dosage form of claim 6, comprising one or more pharmaceutically acceptable excipients.

9. An oral tablet dosage form comprising:
   about 50 wt-% to about 90 wt-% anhydrous crystalline (2R)-2-phenylcarbonyloxypropyl (2S)-2-amino-3-(3,4-dihydroxyphenyl)propanoate mesylate;
   about 0.5 wt-% to about 2.0 wt-% $C_{6-18}$ alkylsulfate or pharmaceutically acceptable salt thereof;
   about 6 wt-% to about 20 wt-% hydroxypropylmethylcellulose; and
   about 0.5 wt-% to about 2 wt-% magnesium stearate;
   wherein wt-% is based on the total dry weight of the dosage form.

10. The dosage form of claim 7, comprising an L-aromatic amino acid decarboxylase inhibitor, a catechol-O-methyltransferase inhibitor, or a combination of an L-aromatic amino acid decarboxylase inhibitor and a catechol-O-methyltransferase inhibitor.

11. The dosage form of claim 6, which when placed in 0.1 N HCl, pH 1.2 at 37° C. and agitated at 50 rpm, releases about 28% to about 58% of the anhydrous crystalline (2R)-2-phenylcarbonyloxypropyl (2S)-2-amino-3-(3,4-dihydroxyphenyl)propanoate mesylate within about 2 hours, about 40% to about 70% within about 4 hours, about 67% to about 97% within about 9 hours, and greater than about 80% within about 18 hours.

12. The dosage form of claim 6, which is a bilayer tablet dosage form comprising:
    a first layer comprising granules comprising anhydrous crystalline (2R)-2-phenylcarbonyloxypropyl (2S)-2-amino-3-(3,4-dihydroxyphenyl)propanoate mesylate and a $C_{6-18}$ alkylsulfate or pharmaceutically acceptable salt thereof; and
    a second layer comprising an L-aromatic amino acid decarboxylase inhibitor.

13. The dosage form of claim 12, wherein the $C_{6-18}$ alkylsulfate or pharmaceutically acceptable salt thereof is sodium lauryl sulfate, and the L-aromatic amino acid decarboxylase inhibitor is carbidopa.

14. An oral tablet dosage form, which a is bilayer tablet dosage form, wherein:
    the first layer comprises the granules comprising about 70 wt-% to about 95 wt-% anhydrous crystalline (2R)-2-phenylcarbonyloxypropyl (2S)-2-amino-3-(3,4-dihydroxyphenyl)propanoate mesylate and about 0.5 wt-% to about 3 wt-% $C_{6-18}$ alkylsulfate or pharmaceutically acceptable salt thereof; and
    the second layer comprises about 15 wt-% to about 30 wt-% of an L-aromatic amino acid decarboxylase inhibitor.

15. The dosage form of claim 12, which when placed in 0.1 N HCl, pH 1.2 or pH 5.0 at 37° C. and agitated at 50 rpm, releases about 28% to about 58% of the anhydrous crystalline (2R)-2-phenylcarbonyloxypropyl (2S)-2-amino-3-(3,4-dihydroxyphenyl)propanoate mesylate within about 2 hours, about 50% to about 80% within about 4 hours, and greater than about 80% within about 12 hours.

16. A method of treating a disease in a patient comprising administering to a patient in need of such treatment a therapeutically effective amount of the pharmaceutical composition of claim 1, wherein the disease is chosen from schizophrenia, a cognitive impairment disorder, restless legs syndrome, a periodic limb movement disorder, tardive dyskinesia, Huntington's disease, hypertension, and excessive daytime sleepiness.

17. A method of treating Parkinson's disease in a patient comprising administering to a patient in need of such treatment a therapeutically effective amount of the pharmaceutical composition of claim 1.

18. A method of treating a disease in a patient comprising administering to a patient in need of such treatment the tablet dosage form of any one of claim 6 and 12, wherein the disease is chosen from schizophrenia, a cognitive impairment disorder, restless legs syndrome, a periodic limb movement disorder, tardive dyskinesia, Huntington's disease, hypertension, and excessive daytime sleepiness.

19. A method of treating Parkinson's disease in a patient comprising administering to a patient in need of such treatment the tablet dosage form of any one of claim 6 and 12.

20. The pharmaceutical composition of claim 1, wherein the granules are substantially free of crystalline (2R)-2-phenylcarbonyloxypropyl (2S)-2-amino-3-(3,4-dihydroxyphenyl)propanoate mesylate, hydrate.

21. The oral dosage form of claim 6, wherein the granules are substantially free of crystalline (2R)-2-phenylcarbonyloxypropyl (2S)-2-amino-3-(3,4-dihydroxyphenyl)propanoate mesylate, hydrate.

* * * * *